(12) United States Patent
Kamen et al.

(10) Patent No.: US 10,792,419 B2
(45) Date of Patent: Oct. 6, 2020

(54) INFUSION SET AND INSERTER ASSEMBLY

(71) Applicant: DEKA Products Limited Partnership, Manchester, NH (US)

(72) Inventors: Dean Kamen, Bedford, NH (US); Jason A. Demers, Manchester, NH (US); Richard J. Lanigan, Concord, NH (US); Timothy D. Moreau, Manchester, NH (US); Brian D. Tracey, Litchfield, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 29 days.

(21) Appl. No.: 15/434,906

(22) Filed: Feb. 16, 2017

(65) Prior Publication Data

US 2017/0281863 A1  Oct. 5, 2017

Related U.S. Application Data

(60) Provisional application No. 62/295,805, filed on Feb. 16, 2016.

(51) Int. Cl.
| | |
|---|---|
| *A61M 5/162* | (2006.01) |
| *A61M 5/168* | (2006.01) |
| *A61M 5/142* | (2006.01) |
| *A61M 39/10* | (2006.01) |
| *A61M 5/158* | (2006.01) |

(Continued)

(52) U.S. Cl.
CPC ........ *A61M 5/162* (2013.01); *A61M 5/14248* (2013.01); *A61M 5/168* (2013.01); *A61M 5/142* (2013.01); *A61M 5/425* (2013.01); *A61M 39/1011* (2013.01); *A61M 2005/14252* (2013.01); *A61M 2005/14268* (2013.01); *A61M 2005/14506* (2013.01);

(Continued)

(58) Field of Classification Search
CPC ......... A61M 2005/14252; A61M 2005/14268; A61M 2005/1583; A61M 2005/1585; A61M 5/14248; A61M 5/162
See application file for complete search history.

(56) References Cited

U.S. PATENT DOCUMENTS

| | | | |
|---|---|---|---|
| 6,520,938 B1 * | 2/2003 | Funderburk | A61M 25/0097 604/162 |
| 6,949,084 B2 * | 9/2005 | Marggi | A61M 25/0097 604/174 |

(Continued)

*Primary Examiner* — Quynh-Nhu H. Vu
(74) *Attorney, Agent, or Firm* — Reid Knott Cunningham

(57) ABSTRACT

A two-stage infusion set inserter system is disclosed. The inserter system includes an inserter assembly including a housing including a rotatable button assembly comprising ramps and and tab indents and a non-rotatable portion of housing, a sliding component comprising sliding component tabs, a needle carrier connected to an introduction needle, the needle carrier slidably movable from a starting position to an injection position and then to a second ending position, a sliding component spring, and a needle spring, wherein the rotatable button assembly rotates from a locked to an unlocked position, wherein when force is applied onto the rotatable button assembly, the sliding component and needle carrier are forced downward by the sliding component spring, and wherein when the needle carrier reaches the injection position, the needle spring forces the needle carrier upward towards the second ending position.

21 Claims, 76 Drawing Sheets

(51) Int. Cl.
*A61M 5/42* (2006.01)
*A61M 5/145* (2006.01)

(52) U.S. Cl.
CPC ............... *A61M 2005/1581* (2013.01); *A61M 2005/1583* (2013.01); *A61M 2005/1585* (2013.01)

(56) References Cited

U.S. PATENT DOCUMENTS

| | | | | |
|---|---|---|---|---|
| 9,039,654 | B2* | 5/2015 | Gravesen | A61M 5/1413 604/65 |
| 9,782,536 | B2* | 10/2017 | Skutnik | A61M 5/14248 |
| 10,130,761 | B2* | 11/2018 | Searle | A61M 5/14248 |
| 2009/0143763 | A1* | 6/2009 | Wyss | A61M 5/158 604/506 |
| 2009/0198215 | A1* | 8/2009 | Chong | A61M 5/1413 604/506 |
| 2010/0198187 | A1* | 8/2010 | Yodfat | A61M 5/16822 604/500 |
| 2013/0310800 | A1* | 11/2013 | Yodfat | A61B 5/14532 604/500 |

\* cited by examiner

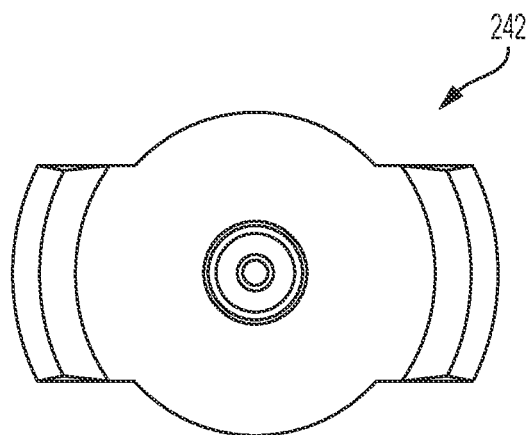
FIG. 53A
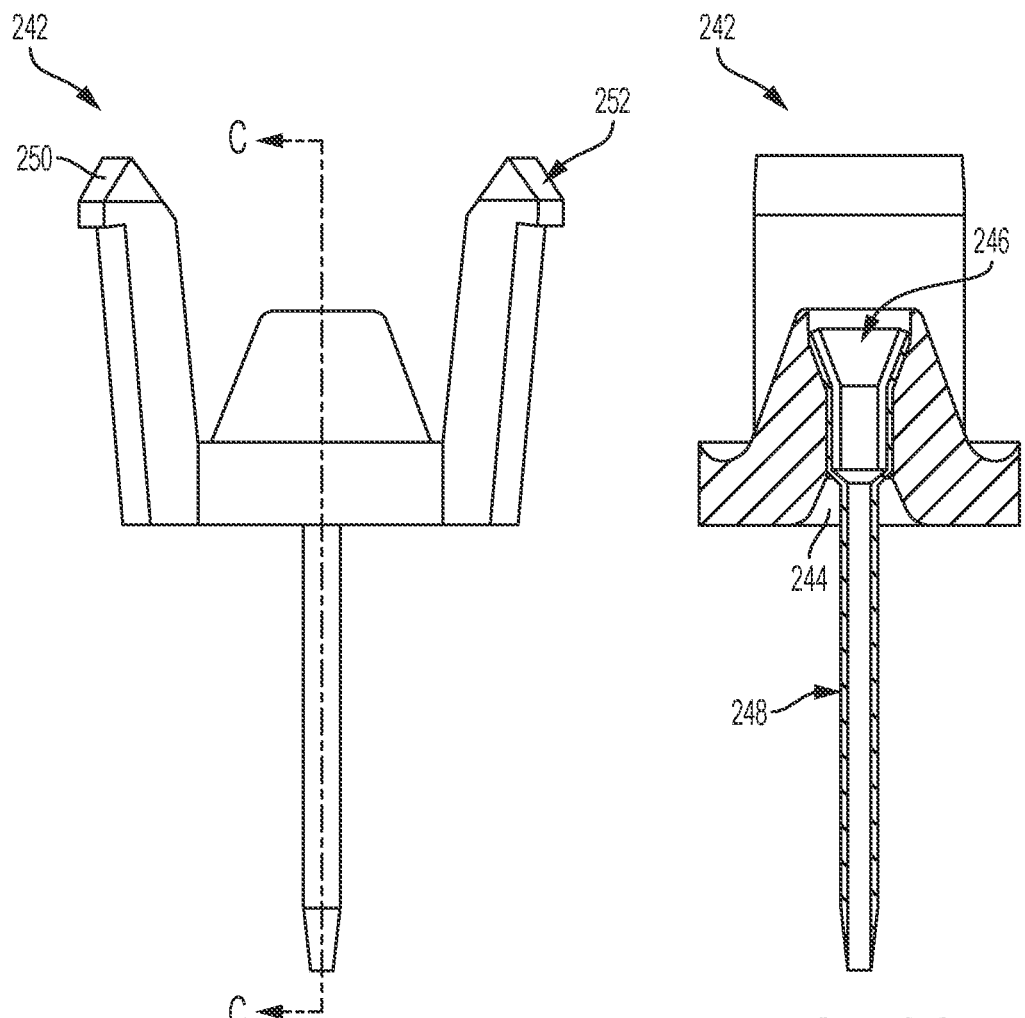
FIG. 53B
FIG. 53C

INFUSION SET AND INSERTER ASSEMBLY

CROSS-RELATED APPLICATION(S)

This application claims the benefit of U.S. Provisional Application Ser. No. 62/295,805 filed Feb. 16, 2016 and entitled Infusion Set and Inserter Assembly and Methods of Using Thereof, which is hereby incorporated herein by reference in its entirety.

FIELD OF THE INVENTION

This application relates generally to infusion sets and inserter assemblies for infusion sets, and more particularly to infusion sets and inserter assemblies and method of using thereof.

BACKGROUND

Many potentially valuable medicines or compounds, including biologicals, are not orally active due to poor absorption, hepatic metabolism or other pharmacokinetic factors. Additionally, some therapeutic compounds, although they can be orally absorbed, are sometimes required to be administered so often it is difficult for a patient to maintain the desired schedule. In these cases, parenteral delivery is often employed or could be employed.

Effective parenteral routes of drug delivery, as well as other fluids and compounds, such as subcutaneous injection, intramuscular injection, and intravenous (IV) administration include puncture of the skin with a needle or stylet. Insulin is an example of a therapeutic fluid that is self-injected by millions of diabetic patients. Users of parenterally delivered drugs may benefit from a wearable device that would automatically deliver needed drugs/compounds over a period of time.

To this end, there have been efforts to design portable and wearable devices for the controlled release of therapeutics. Such devices are known to have a reservoir such as a cartridge, syringe, or bag, and to be electronically controlled. These devices suffer from a number of drawbacks including the malfunction rate. Reducing the size, weight and cost of these devices is also an ongoing challenge. Additionally, these devices often apply to the skin and pose the challenge of frequent re-location for application.

SUMMARY OF THE INVENTION

In accordance with one implementation, a two-stage infusion set inserter system is disclosed. The inserter system includes an inserter assembly including a housing including a rotatable button assembly comprising ramps and and tab indents and a non-rotatable portion of housing, a sliding component comprising sliding component tabs, a needle carrier connected to an introduction needle, the needle carrier slidably movable from a starting position to an injection position and then to a second ending position, a sliding component spring, and a needle spring, wherein the rotatable button assembly rotates from a locked to an unlocked position, wherein when force is applied onto the rotatable button assembly, the sliding component and needle carrier are forced downward by the sliding component spring, and wherein when the needle carrier reaches the injection position, the needle spring forces the needle carrier upward towards the second ending position.

Some embodiments of this implementation may include one or more of the following. Wherein the rotatable button assembly comprising ramps and and tab indents. Wherein the sliding component comprising sliding component tabs. Wherein when the rotatable button assembly is in the locked position, the sliding component tabs are in the tab indents. Wherein when the rotatable button assembly is in the unlocked position, the ramps are in contact with the sliding component tabs. Wherein the system further comprising an infusion set attached to the housing. Wherein the infusion set comprising a base and wherein the base comprising an adhesive layer. Wherein the adhesive layer comprising an adhesive liner. Wherein the system further comprising a slider stop, wherein when the sliding component reaches the slider stop, the slider stop forces the sliding component to stop downward movement. Wherein the needle carrier comprising spring fingers and wherein when the needle carrier interacts with the slide stop, the slide stop forces the spring fingers inward and the needle carrier moves from the injection position to the ending position.

Wherein the system further comprising an introduction needle connected to the needle carrier, wherein when the needle carrier moves to the ending position, the introduction needle moves to the ending position and wherein the introduction needle is inside the housing portion. Wherein the rotatable button assembly comprising a first alignment indicia and the non-rotatable portion of housing comprising a second alignment indicia, wherein when the rotatable button assembly rotates from a locked position to an unlocked position, the first alignment indicia and the second alignment indicia line up to indicate the system is in the unlocked position.

In accordance with another implementation, an infusion device is disclosed. The infusion device includes a base portion including a cannula and a septum retainer comprising a retainer cutout, wherein the cannula is located within the retainer cutout, and a connector comprising a connector needle, the connector removably attached to the base portion, wherein the cannula may pivot within the retainer cutout with respect to the base.

Some embodiments of this implementation may include one or more of the following. Wherein the base portion further including a cutout area configured for receiving a length of tubing. Wherein the connector including connector fingers comprising ribbing. Wherein the connector comprising a connector needle protector located above the connector needle. Wherein the retainer cutout comprising a topically introduced ointment. Wherein the device further includes a predetermined length of tubing connector to the connector. Wherein the base further includes a finger grip area configured for finger grip stability while connecting the base and the connector. Wherein the retainer cutout is conical.

The details of one or more embodiments are set forth in the accompanying drawings and the description below. Other features and advantages will become apparent from the description, the drawings, and the claims.

BRIEF DESCRIPTION OF THE DRAWINGS

FIGS. 53A-53C are various views of one embodiment of a septum retainer;

Like reference symbols in the various drawings indicate like elements.

DETAILED DESCRIPTION

In various embodiments, an infusion set may may be used in conjunction with an infusion device and system and methods thereof as well as used in conjunction with an inserter assembly. In various embodiments, the infusion set is configured to be inserted into the subcutaneous layer of a user's skin and be fluidly connected to a fluid source. In various embodiments, the infusion set may be fluidly connected to a length of tubing and/or to an infusion pump. Infusion pumps include any infusion pump which may include, but is not limited to, the various infusion pumps shown and described in any one or more of the following: U.S. patent application Ser. No. 13/788,260, filed Mar. 7, 2013 and entitled Infusion Pump Assembly, now U.S. Publication No. US-2014-0107579, published Apr. 17, 201; U.S. Pat. No. 8,491,570, issued Jul. 23, 2013 and entitled Infusion Pump Assembly; U.S. Pat. No. 8,414,522, issued Apr. 9, 2013 and entitled Fluid Delivery Systems and Methods; U.S. Pat. No. 8,262,616, issued Sep. 11, 2012 and entitled Infusion Pump Assembly; and U.S. Pat. No. 7,306,578, issued Dec. 11, 2007 and entitled Loading Mechanism for Infusion Pump; all of which are attached hereto, and are hereby incorporated herein by reference in their entireties. In various embodiments, the various embodiments of the infusion devices described herein may be used alone or in conjunction with an infusion set.

Various embodiments are described and shown herein. Each embodiment of each element may be used in any other embodiment of any device. Each embodiment of the inserter device may be used with any embodiment of the infusion set devices.

A system is disclosed which includes an infusion set and an inserter device. In various embodiments, the inserter device includes one or more disposable portions.

Infusion Set

Figure 5:
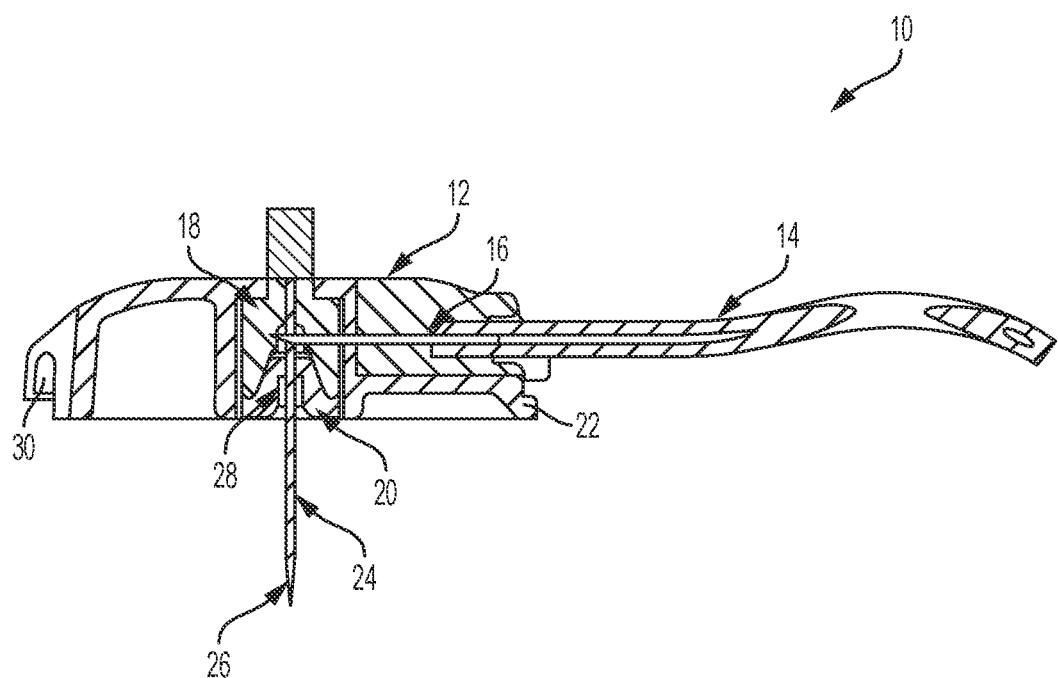
Figure 6:
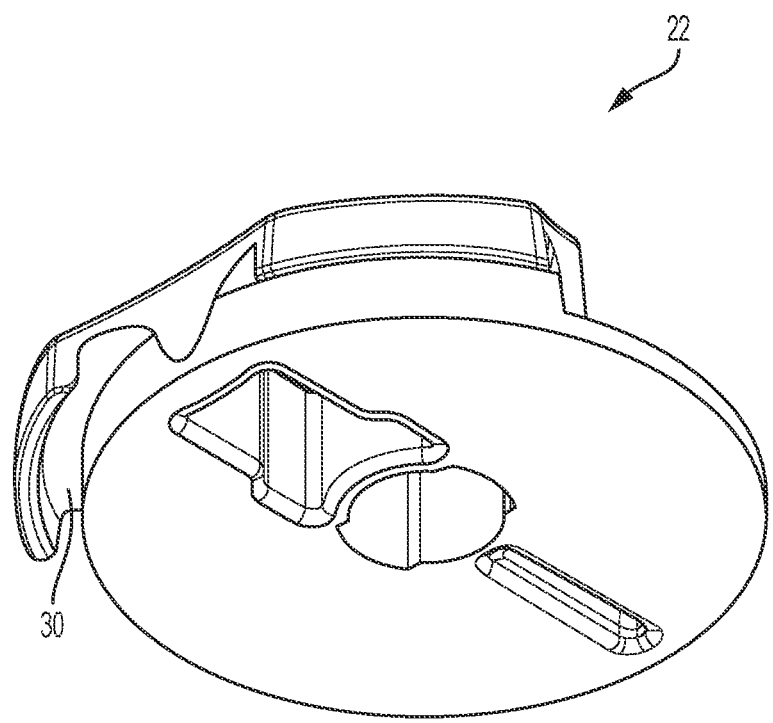
FIGS. 6-13 are various views of one embodiment of an infusion set.
Figure 7:
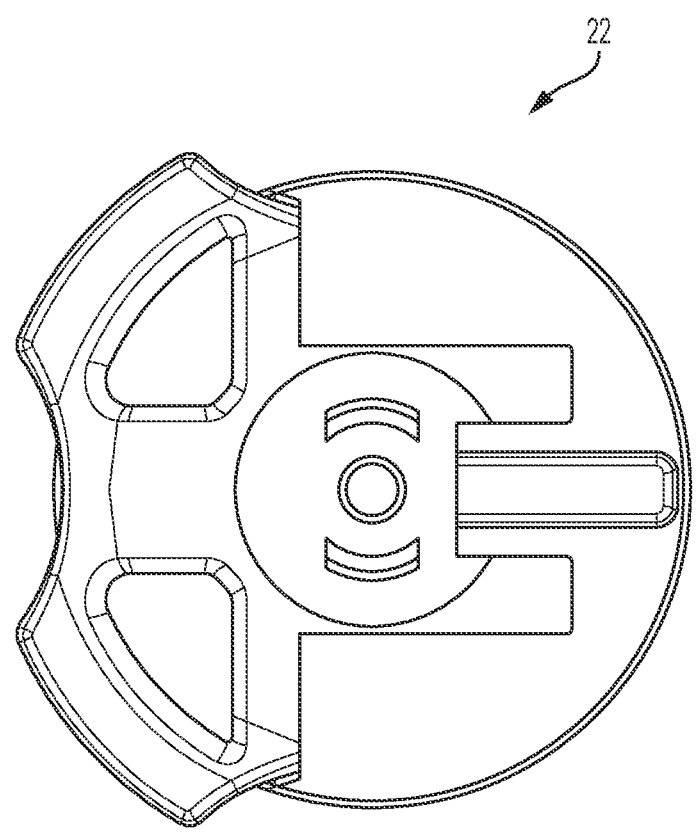
Figure 8:
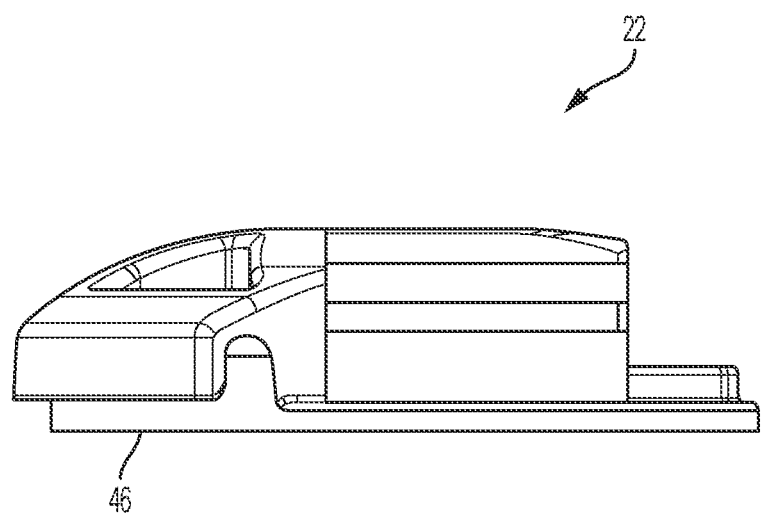
Figure 9:
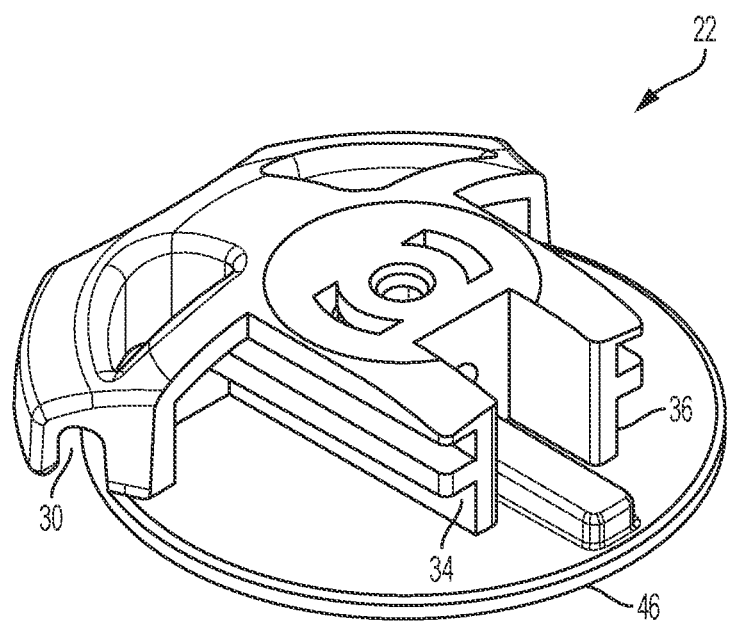
Figure 10:
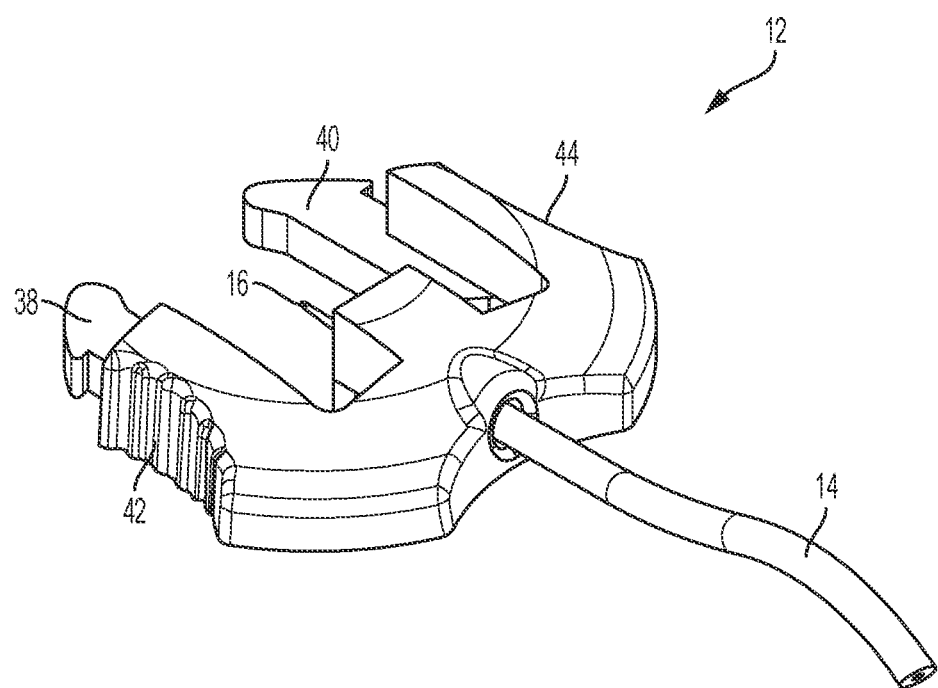
Figure 11:
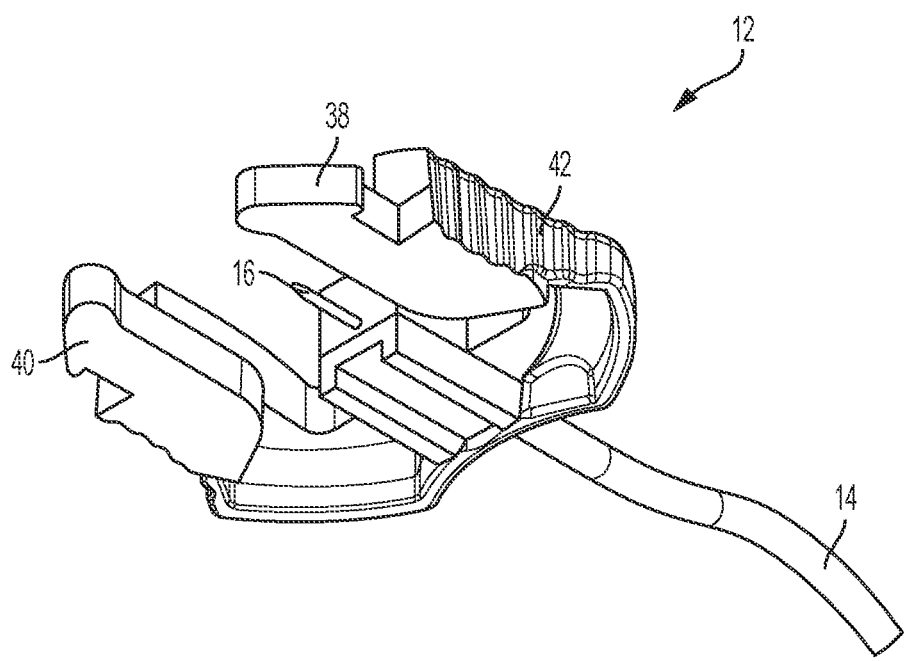
Figure 12:
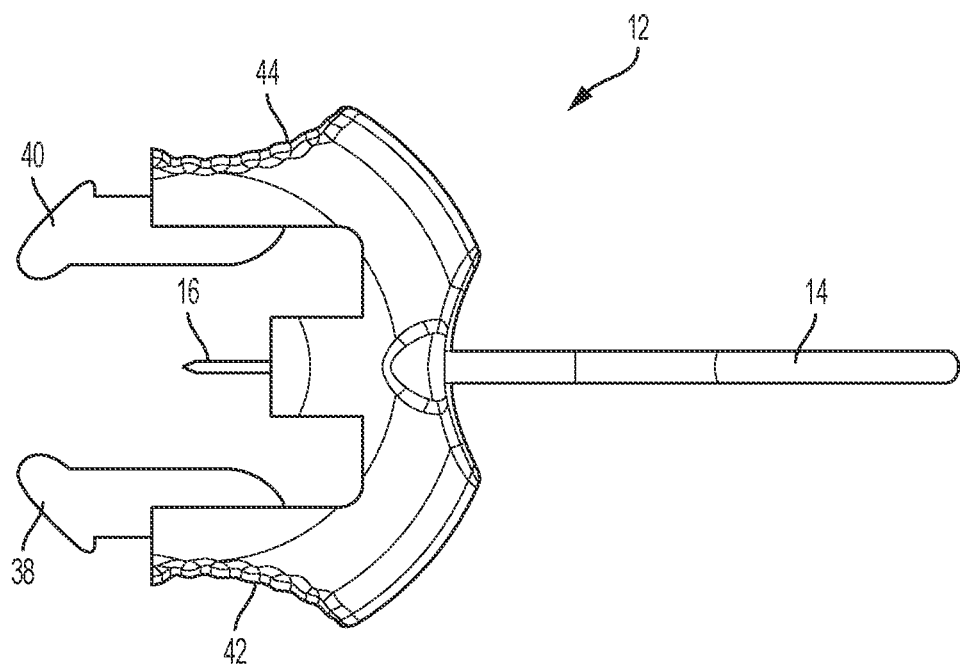
Figure 13:
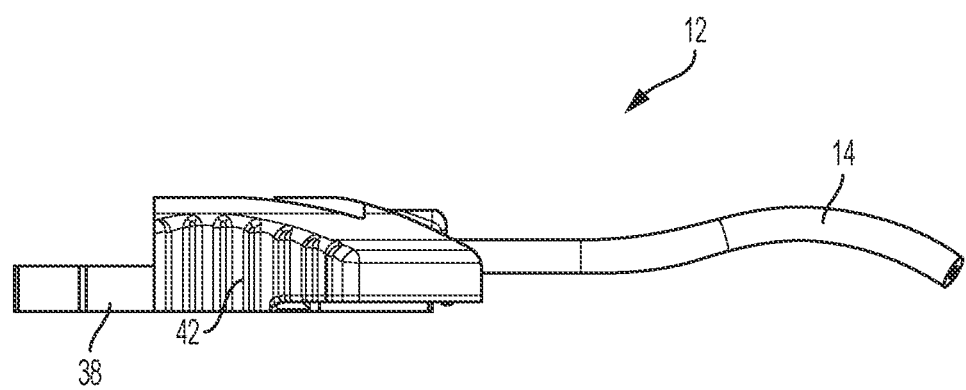

In various embodiments, an infusion set is disclosed. Referring now to FIGS. 1-5, an embodiment of an infusion set 10 is shown. In various embodiments, the infusion set 10 includes a connector 12, tubing 14, a connector needle 16, a septum 18, a septum retainer 20, a base 22, a cannula 24 and an introduction needle 26. The connector 12 includes a connector needle 16 which, when brought into contact with the base 22 is inserted through the septum 18 such that it is in fluid communication with the cannula 24. In addition, in some embodiments, one which is shown in FIG. 5, the infusion set may additionally include a funnel 28 which, in various embodiments, may be desirable/beneficial for it functions as a needle guide to guide the introduction needle 26.

Still referring to FIGS. 1-6 and FIG. 49, In various embodiments, the septum 18 is press fit into the base 22 and the septum retainer 20, introduction needle 26, and funnel 28 are also press fit into the base 22. In various embodiments, the base 22 includes a cutout area 30. The cutout area 30 is configured to accommodate a length of tubing 14 as it is wrapped around the infusion set 10. This may be beneficial/desirable for many reasons, including, but not limited to, preventing kinking of the tubing 14, as once the tubing 14 is wrapped around the infusion set 10, when pulled in various directions or at an angle, the tubing may have less chances of kinking, and kinking may cause occlusions. In various embodiments, the cutout area 30 functions as a tubing organizer.

In various embodiments, the tubing 14 may wrap around the infusion set 10 and may be clipped or otherwise secured in place. The clipping or securing may be done in any direction. Thus, in various embodiments, the wrapping the tubing around the infusion set 10 may allow changing the direction of the tubing. In some embodiments, the tubing 14 may be routing underneath the infusion set 10 to change the direction.

In various embodiments, the base 22 includes an adhesive layer on the bottom. However, in various other embodiments, the base may not include an adhesive layer on the bottom. In some embodiments, the adhesive layer may be covered with a paper or other to prevent exposure of the adhesive prior to adhering to a user/patient's skin. Prior to adhering to the skin, the paper or other may be removed and the base 22 may be pressed against the user/patient's skin. The adhesive maintains the base 22 on the skin.

In some embodiments, an adhesive layer may be included on an inserter device such as one of the various embodiments described herein. In some embodiments of these embodiments, as the infusion set is pushed towards the user, the infusion set comes into contact with an adhesive layer. In some embodiments, however, an adhesive layer may be located on both the inserter and the infusion set.

Figure 1:
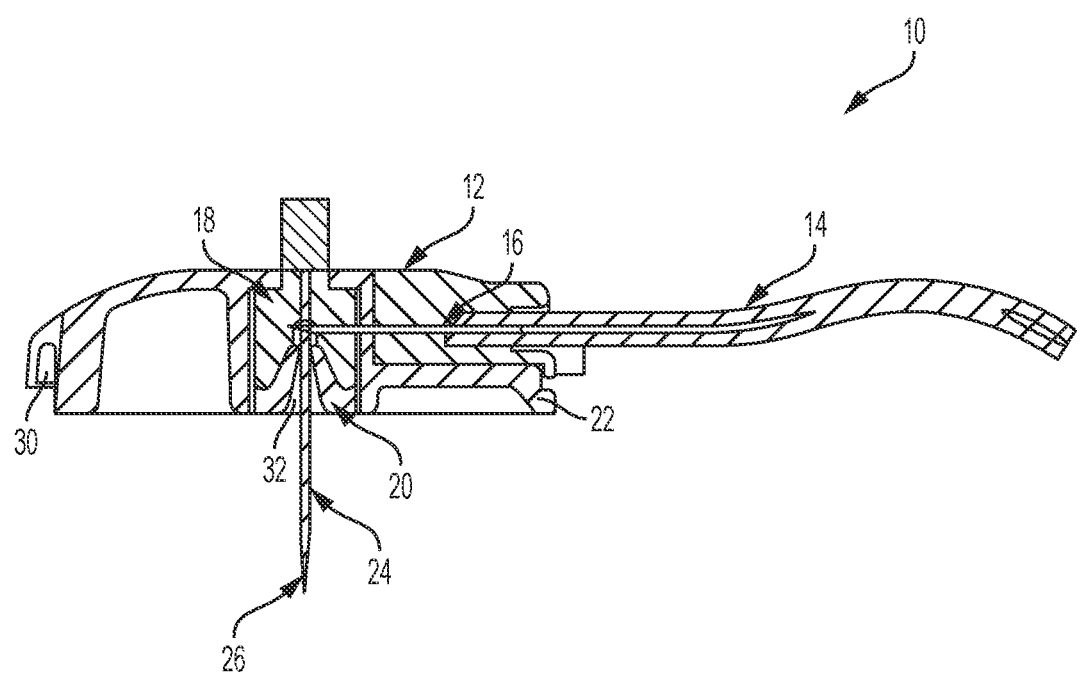
FIGS. 1-5 are various views of one embodiment of an infusion set.
Figure 2:
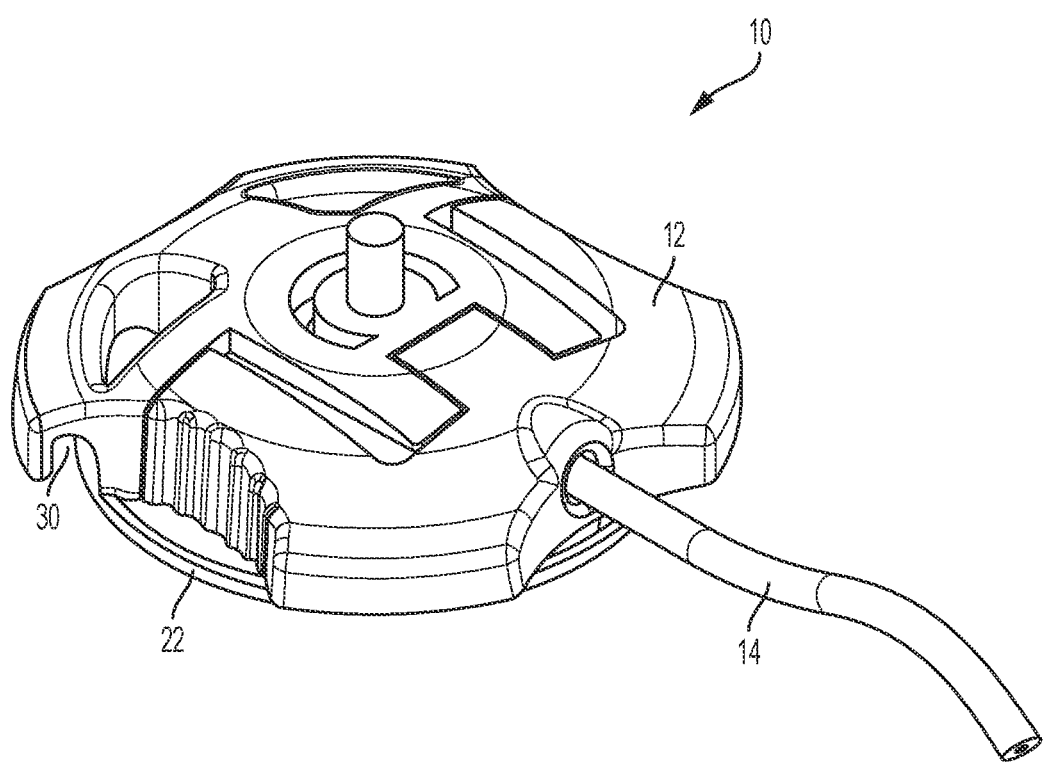
Figure 3:
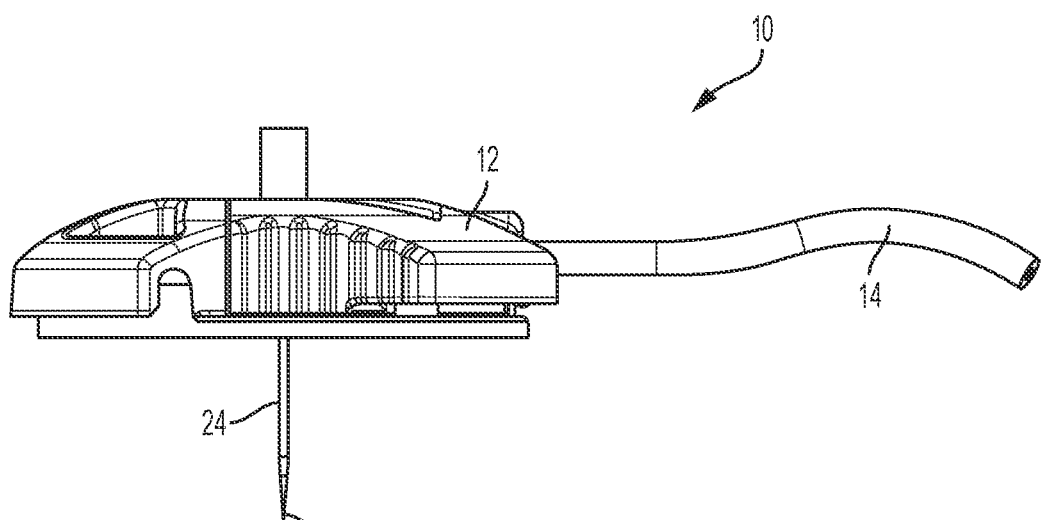
Figure 4:
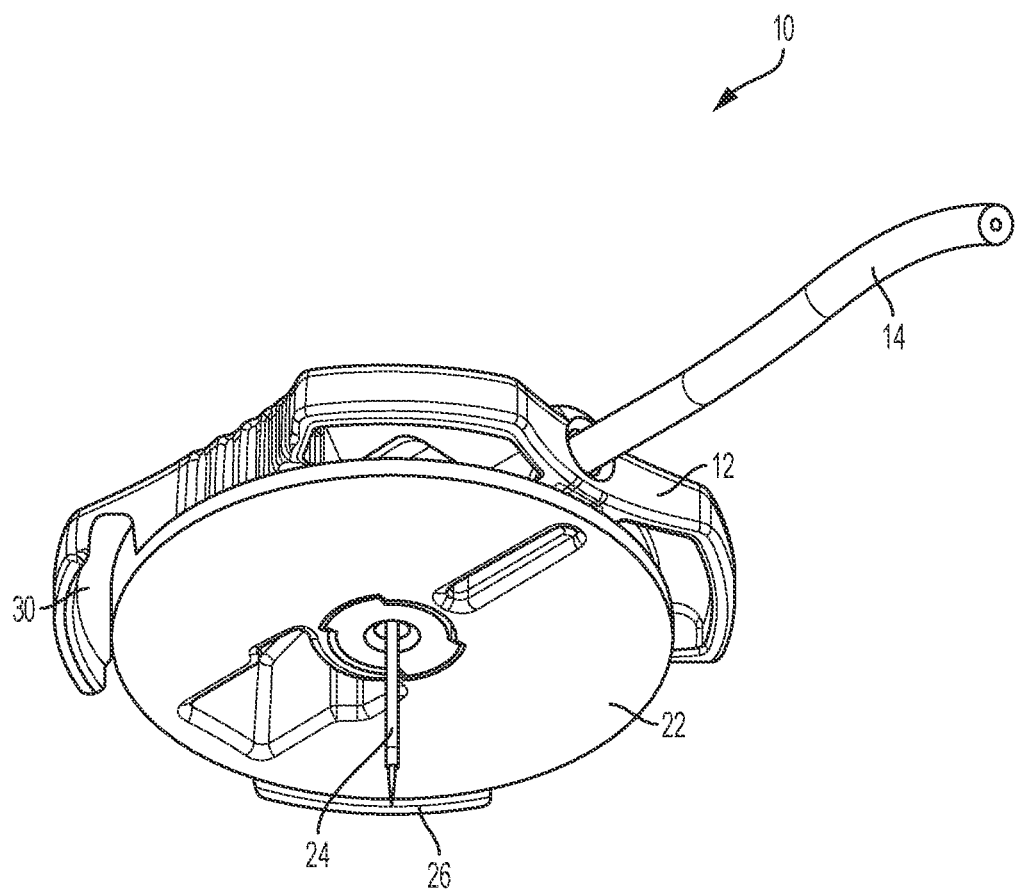

Referring now to FIG. 1, in various embodiments of the infusion set 10, the base 22 may include a retainer cutout 32. In various embodiments, the retainer cutout 32 may be conical in shape and may provide ample room for the cannula 24 to move about with respect to the base 22 when the base 22 moves due to the location on a user/patient's skin. In various embodiments, a retainer cutout 32 may be any shape or size including the shape and size shown in FIG. 1. In various embodiments, the retainer cutout 32 may be beneficial/desirable for many reasons, including but not limited to, while the infusion set 10 may be attached to the user, when the user's skin moves, the retainer cutout 32 provides ample room such that the cannula 24 is not sheared. Thus, the retainer cutout 32 essentially moves the pivot point of the cannula 24 further away from the skin than it would be if the retainer cutout 32 were not included.

Still referring to FIGS. 1-6, in various embodiments, the cannula 24 may be tapered and in some embodiments, the cannula 24 may not be tapered.

Referring now also to FIGS. 6-13, an embodiment of the base 22 and connector 12 are shown. The base includes an adhesive layer 46, which, as discussed above, may also include a liner/paper or other to protect the adhesive layer 46. The base 22 includes connector receivers 34, 36 that are configured to receive connector fingers 38, 40. The connector fingers 38, 40 slide into the connector receivers 34, 36 and snap or lock into place such that once snapped or locked into place, the connector 12 and the base 22 are joined or mated and will not become unjoined or unmated until or unless the connector releases 42, 44 are pressed towards each other. Pressing the connecting releases 42, 44 towards each other releases the connector fingers 38, 40 such that they may be removed from the connector receivers 34, 36.

By sliding the connector fingers 38, 40 of the connector 12 into the connector receivers 34, 36 on the base 22, the connector 12 is removably attached to the base 22. This action additionally causes the connector needle 16 to pierce the septum 18 of the base 22 such that the connector needle 16 is fluidly connected to the cannula 24. Once the connector needle 16 is fluidly connected to the cannula 24, fluid flowing from, for example, an infusion pump or other supply of fluid and through the tubing 14 (which, in various embodiments, may be fluidly connected to a reservoir in an infusion pump), may flow through the cannula 24 and into the user/patient.

Figure 14:
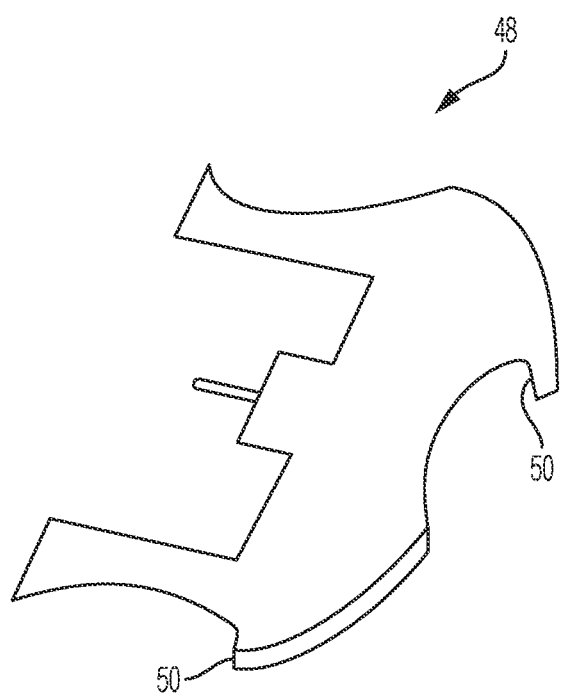
FIG. 14 is a view of one embodiment of a connector of an infusion set.
Figure 15:
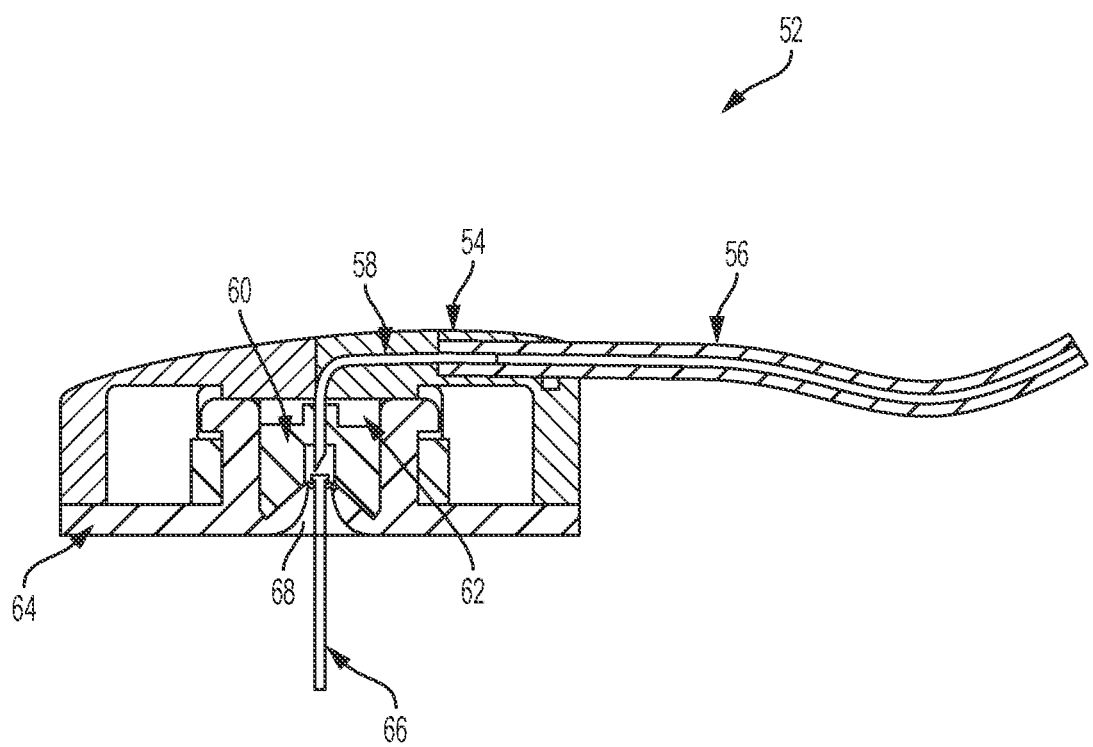
FIGS. 15-18 are various views of one embodiment of an infusion set.
Figure 16:
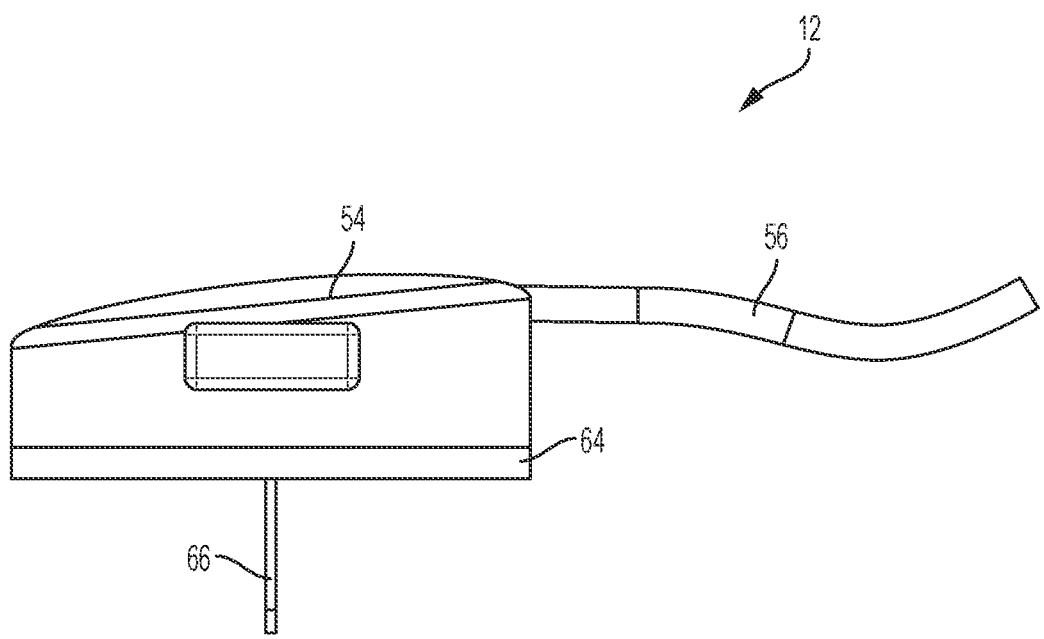
Figure 17:
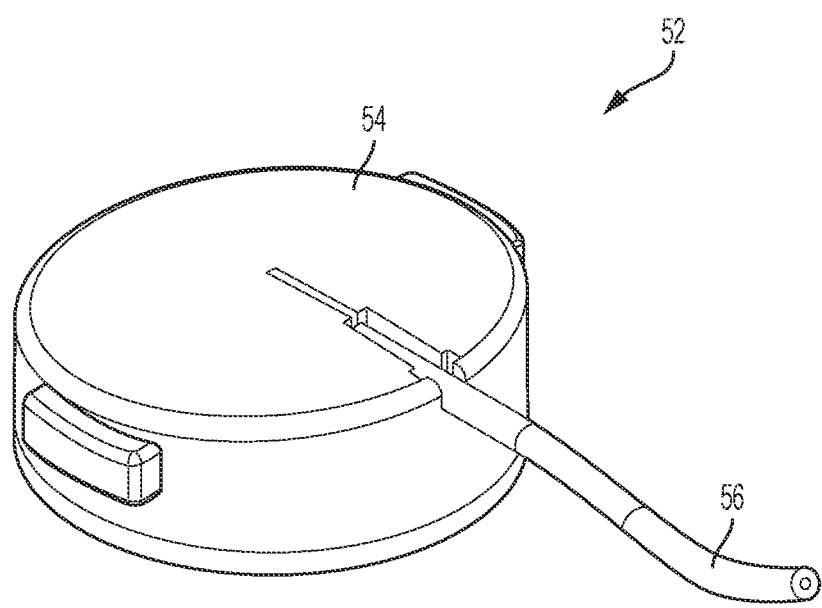
Figure 18:
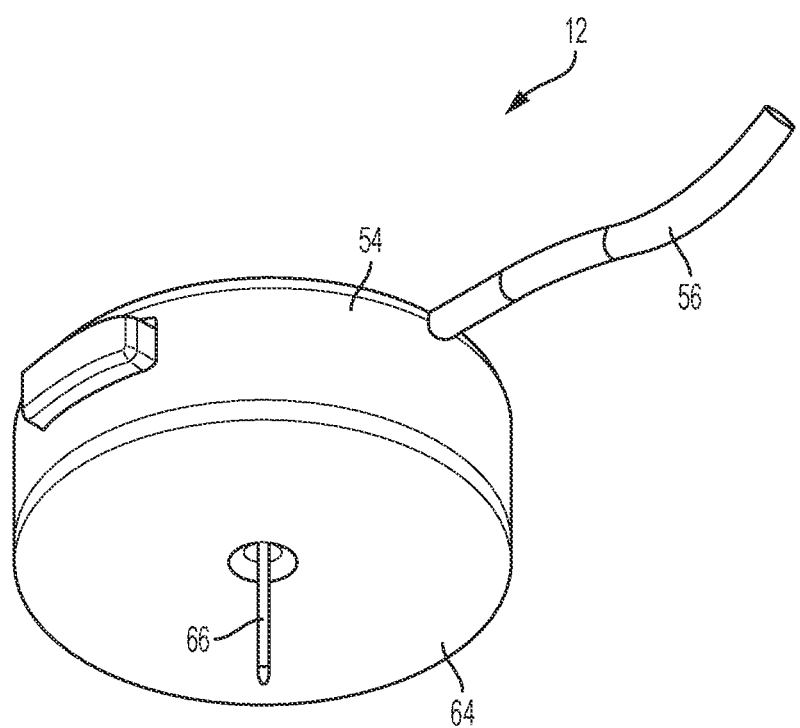
Figure 19:
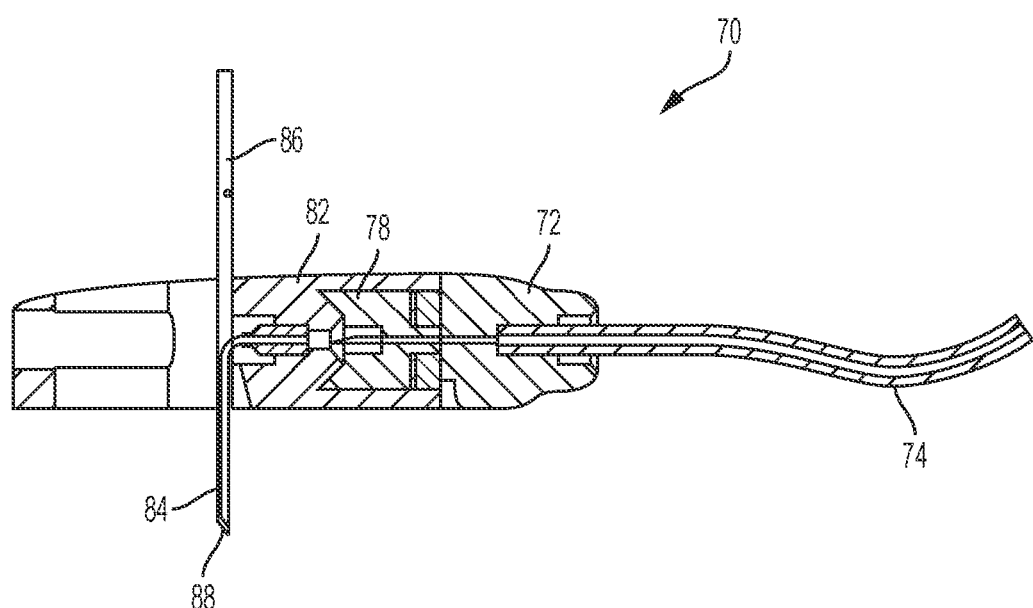
FIGS. 19-22 are various views of one embodiment of an infusion set.
Figure 20:
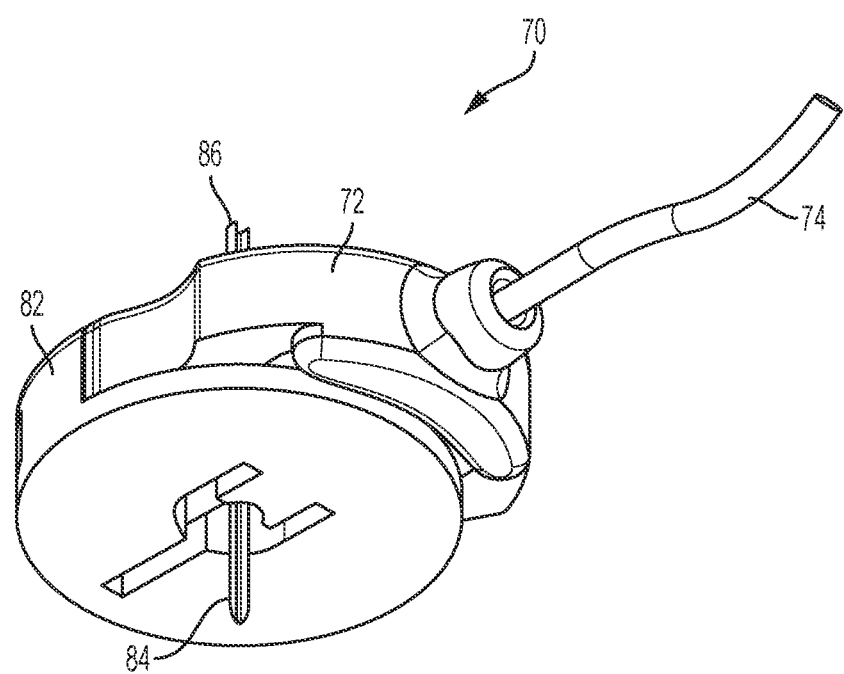
Figure 21:
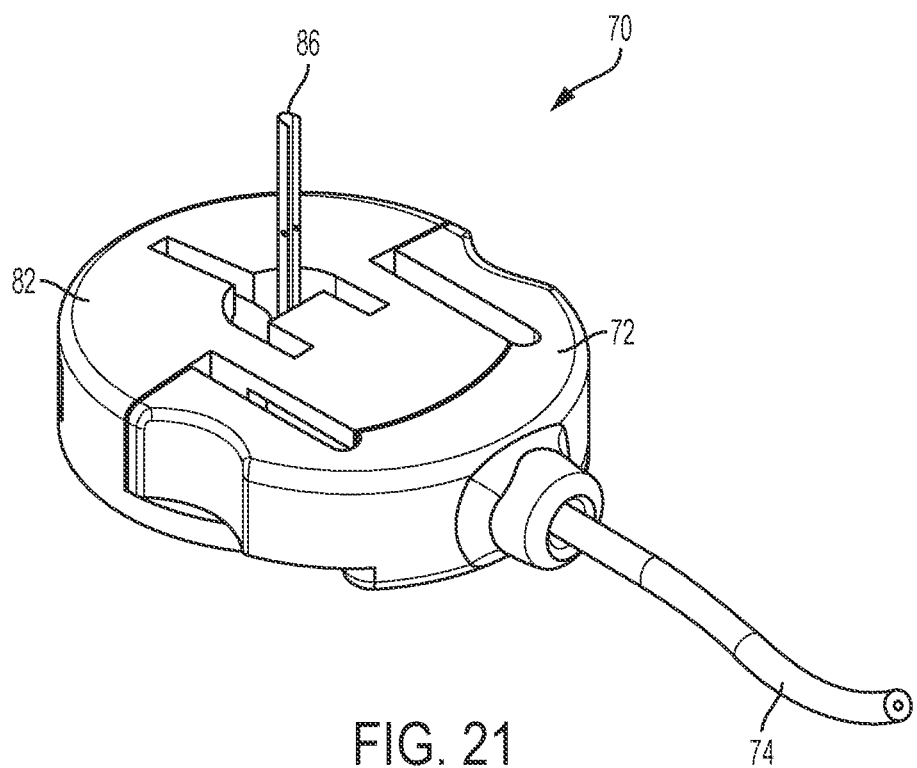
Figure 22:
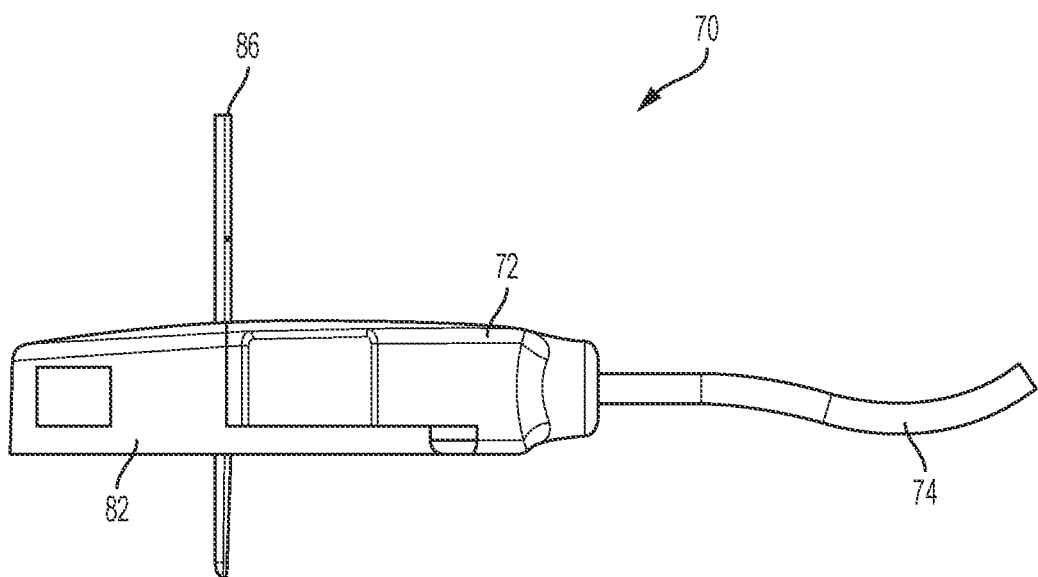
Figure 23:
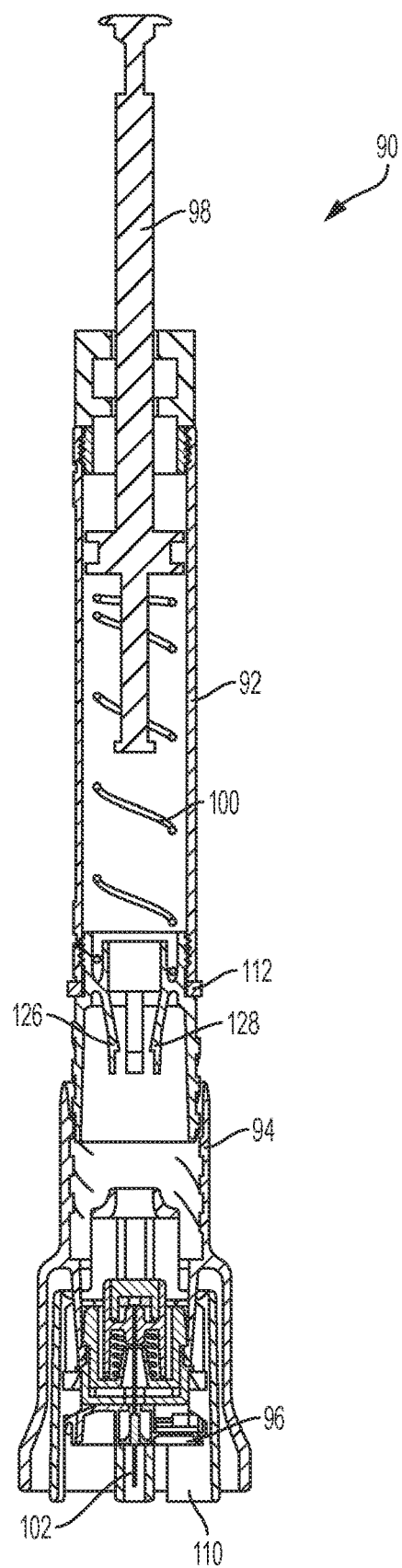
FIGS. 23-33 are various views of one embodiment of an infusion set inserter system.

Referring now to FIG. 14, in some embodiments, the connector 48 may include a cutout area 50, rather than the base including a cutout area. However, in various embodiments, both the base and the connector may include a cutout area and in some embodiments, either the base or connector may or may not include a cutout area.

Referring now also to FIGS. 15-18, another embodiment of an infusion set 52 is shown. In this embodiment, the connector 54 includes a bent connector needle 58, tubing 56, which, when the connector 54 is mated with or attached to the base 64, is in fluid communication with the cannula 66. This embodiments of the infusion set 52 also includes a funnel 68 which acts as a retainer cutout, functioning similarly as discussed above. In this embodiments, the connector 54 mates with the base 64 by being set down on top of the base 64. The bent connector needle 58 is configured such that the connector needle 58 may spin 360 degrees. The connector needle 58, upon connecting to the base, is centered on the septum 60. In various embodiments, the bent connector needle 58 is aligned with the base 64 such that it is centered so that a seal is maintained once the bent connector needle 58 is attached to the base 64, such that upon rotation, the seal is maintained to prevent leaking.

Referring now also to FIGS. 19-22, another embodiment of the infusion set 70 is shown. In some embodiments of the infusion set 70, the introduction needle 86 may be "c"-shaped (or "v"-shaped or half-moon-shaped, etc.) and may wrap around the cannula 84, thus, the cannula 84 is internal to the introduction needle 86. Although in this embodiment, the introduction needle 86 is "c"-shaped, in other embodiments, the introduction needle 86 may be any shape which includes, but is not limited to, wrapping almost or essentially or approximately completely around the cannula 84 (in some embodiments, the needle may wrap completely around the cannula 84 but in other embodiments the needle may wrap less than completely around the cannula). The "c"-shaped introduction needle 86 may be desirable/beneficial for many reasons, including, but not limited to, after insertion of the cannula 84 into the user/patient, the introduction needle 86 is free to slide away from the cannula 84 without pulling the cannula 84 or otherwise dislodging it from inside the user/patient, which may be a risk where the introduction needle is inside the cannula. Additionally, in embodiments where the introduction needle is "c"-shaped or otherwise around the cannula 84, the introduction needle 86 protects the cannula. As shown in the figures, the introduction needle 86 extends passed the cannula 84 therefore, pushes through the skin, however, in various embodiments, the introduction needle 86 has an angled tip 88 which assists in the introduction needle 86 to pull away from the cannula 84 (i.e., assists in moving the cannula 84 out of the way so that the introduction needle 86 may pull away) once insertion of the cannula 84 is complete.

Additionally, the "c"-shaped introduction needle 86 around the cannula 84 allows for the cannula 84 to be a smaller diameter than, for example, infusion sets where the introduction needle is inside the cannula. A smaller diameter cannula may be desirable/beneficial for many reasons, including, but not limited to, the cannula may be bent 90 degrees without breaking or kinking and therefore, this may be desirable/beneficial for many reasons, including, but not limited to, flexibility leading to a more comfortable experience for the user/patient and/or the cannula may be less prone to occluding.

The infusion set 70 also includes a connector 72 which connector 72 including a tubing 74. The connector 72 connects to the base 82.

In the various embodiments of the infusion sets described above, the various embodiment exhibit many benefits and therefore, may be beneficial/desirable for many reasons including but not limited to the following. In various embodiments, the design of the infusion set prevents or reduces the chance of tubing kinking. Additionally, the infusion set designs allow for the tubing to extend from the cannula site at any angle which could, in various embodimens, allow for a short tubing, allow more comfortable and variable positioning, and allow such that there is no alignment with the infusion set required. Thus, the user may inser the infusion set at any angle or direction and still have the direction/position of the tubing desired.

In various embodiments, a retainer cutout is included, as described above. In some embodiments of these embodiments of the infusion set, an antiseptic or other topically introduced ointment, whether medicinal or nutritional or other, may be included. Thus, upon attachments of the infusion set to the user, and insertion of the cannula, an antiseptic or other topically introduced ointment, whether medicinal or nutritional or other may be introduced onto the user's skin. This may be beneficial/desirable for many reasons, including, but not limited to, preventing infection and/or introducing medicine or nutriceuticals or nutritional compounds to the user in a convenient manner.

Figure 50A:
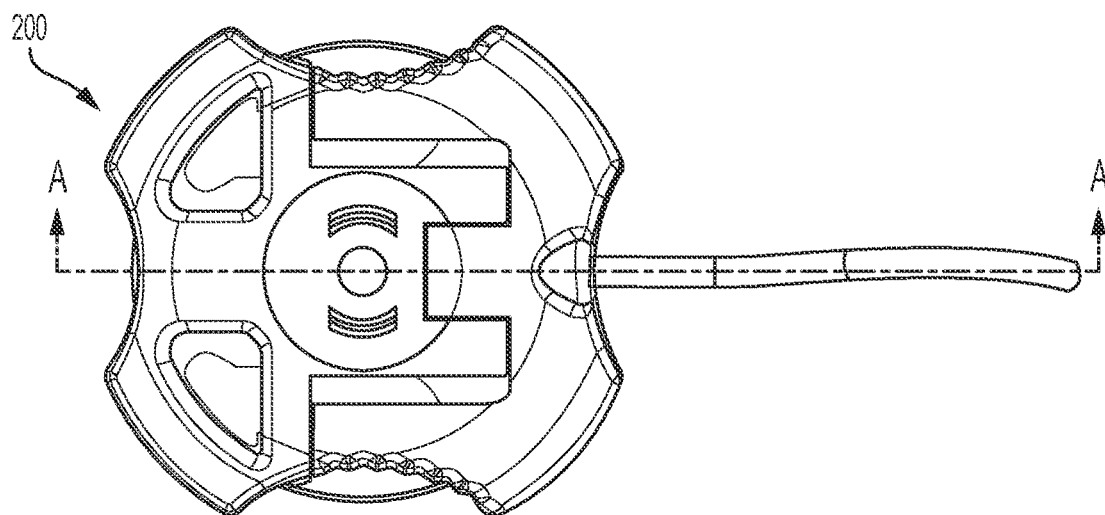
FIGS. 50A-50C are various views of one embodiment of an infusion set.
Figure 50B:
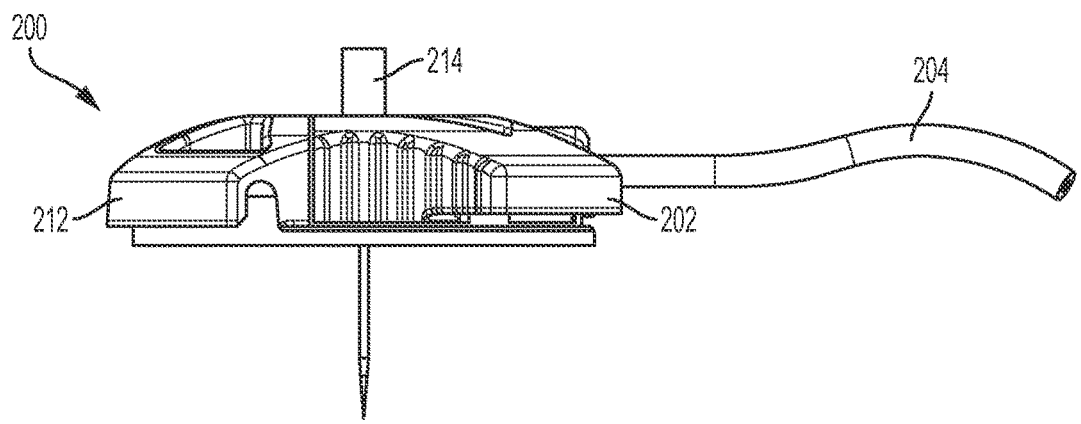
Figure 50C:
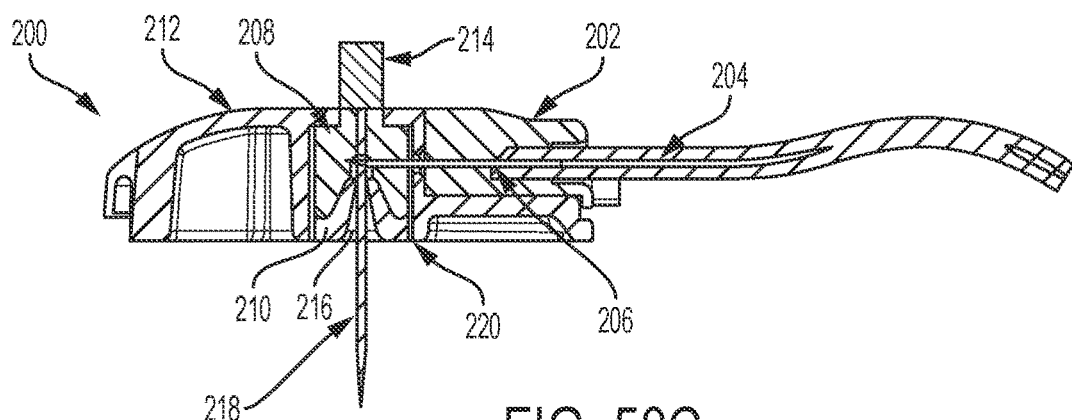

Referring now also to FIGS. 50A-50C, another embodiment of an infusion set 200 is shown. In various embodiments, the infusion set 200 includes a connector 202, tubing 204, a connector needle 206, a septum 208, a septum retainer 210, a base 212, a cannula 218 and an introduction needle 214. The connector 202 includes a connector needle 206 which, when brought into contact with the base 212 is inserted through the septum 208 such that it is in fluid communication with the cannula 218. In addition, in some embodiments, the infusion set may additionally include a funnel (not shown, See FIG. 5) which, in various embodiments, may be desirable/beneficial for it functions as a needle guide to guide the introduction needle 214.

Still referring to FIGS. 50A-50C, in various embodiments, the septum 208 is press fit into the base 212 and the septum retainer 210 and introduction needle 214 are also press fit into the base 212.

In various embodiments, the base 212 includes an adhesive layer 220 on the bottom. However, in various other embodiments, the base 212 may not include an adhesive layer 220 on the bottom. In some embodiments, the adhesive layer 220 may be covered with a paper or other to prevent exposure of the adhesive prior to adhering to a user/patient's skin. Prior to adhering to the skin, the paper or other may be removed and the base 212 may be pressed against the user/patient's skin. The adhesive maintains the base 212 on the skin.

In some embodiments, an adhesive layer 220 may be included on an inserter device such as one of the various embodiments described herein. In some embodiments of these embodiments, as the infusion set is pushed towards the user, the infusion set comes into contact with an adhesive layer. In some embodiments, however, an adhesive layer may be located on both the inserter and the infusion set.

Referring now also to FIGS. 51A-51D, in some embodiments, the septum retainer 210 may be shaped as shown in FIG. 50C. The septum retainer 210 is shown in more detail in FIGS. 51A-51D. In various embodiments, the septum retainer 210 is press fit into the base 212 of the infusion set 200. In various embodiments, the septum retainer 210 is retained in the base 212 by septum retainer fingers 224, 226. However, in various other embodiments, other mechanisms for retention may be used. In some embodiments, the septum retainer 210 may be ultrasonically or otherwise welded into the base 212.

In various embodiments, the cannula 218 may be manufactured from the same material as the septum retainer 210 and in some embodiment, the cannula 218 and septum retainer 210 may be ultrasonically welded, heat bonded or otherwise attached together.

In various embodiments of the infusion set 200, the base 212 may include the septum retainer 210 which may include a retainer cutout 216. In various embodiments, the retainer cutout 216 may be conical in shape and may provide ample room for the cannula 218 to move about with respect to the base 212 when the base 212 moves due to the location on a user/patient's skin. In various embodiments, a retainer cutout 216 may be any shape or size including the shape and size shown in FIG. 51B. In various embodiments, the retainer cutout 216 may be beneficial/desirable for many reasons, including but not limited to, while the infusion set 200 may be attached to the user, when the user's skin moves, the retainer cutout 216 provides ample room such that the cannula 218 is not sheared. Thus, the retainer cutout 216 essentially moves the pivot point of the cannula 218 further away from the skin than it would be if the retainer cutout 216 were not included.

In various embodiments, the cannula 218 may be tapered and in some embodiments, the cannula 218 may not be tapered.

In various embodiments, an antiseptic or other topically introduced ointment, whether medicinal or nutritional or other, may be included in the retainer cutout 216. Thus, upon attachments of the infusion set 200 to the user, and insertion of the cannula 218, an antiseptic or other topically introduced ointment, whether medicinal or nutritional or other may be introduced onto the user's skin. This may be beneficial/desirable for many reasons, including, but not limited to, preventing infection and/or introducing medicine or nutriceuticals or nutritional compounds to the user in a convenient manner.

Referring now also to FIGS. 52A-52D, in some embodiments, the septum retainer 228 may be shaped as shown. In various embodiments, the septum retainer 228 is press fit into the base 212 of the infusion set 200. In various embodiments, the septum retainer 228 is retained in the base 212 by septum retainer fingers 236, 238. However, in various other embodiments, other mechanisms for retention may be used. In some embodiments, the septum retainer 228 may be ultrasonically or otherwise welded into the base 212.

In various embodiments, the cannula 234 may be manufactured from the same material as the septum retainer 228 and in some embodiments, the cannula 234 and septum retainer 228 may be molded as a single part.

In various embodiments of the infusion set 200, the base 212 may include the septum retainer 228 which may include a retainer cutout 230. In various embodiments, the retainer cutout 230 may be round and/or conical in shape and may provide ample room for the cannula 234 to move about with respect to the base 212 when the base 212 moves due to the location on a user/patient's skin. In various embodiments, a retainer cutout 230 may be any shape or size including the shape and size shown in FIGS. 52B and 52D. In various embodiments, the retainer cutout 230 may be beneficial/desirable for many reasons, including but not limited to, while the infusion set 200 may be attached to the user, when the user's skin moves, the retainer cutout 230 provides ample room such that the cannula 234 is not sheared. Thus, the retainer cutout 230 essentially moves the pivot point of the cannula 234 further away from the skin than it would be if the retainer cutout 230 were not included.

In various embodiments, the cannula 234 may be tapered and in some embodiments, the cannula 234 may not be tapered.

In various embodiments, an antiseptic or other topically introduced ointment, whether medicinal or nutritional or other, may be included in the retainer cutout 230. Thus, upon attachments of the infusion set 200 to the user, and insertion of the cannula 234, an antiseptic or other topically introduced ointment, whether medicinal or nutritional or other may be introduced onto the user's skin. This may be beneficial/desirable for many reasons, including, but not limited to, preventing infection and/or introducing medicine or nutriceuticals or nutritional compounds to the user in a convenient manner.

In various embodiments, the septum retainer 228 may include a needle guide 240 which guides the introduction needle 214 through the septum 208 and into the cannula 234. In various embodiments, the needle guide 240 may be any shape or size, including, but not limited to, the shape and size shown in FIG. 52D.

Referring now also to FIGS. 53A-53C, in some embodiments, the septum retainer 242 may be shaped as shown. In various embodiments, the septum retainer 242 is press fit into the base 212 of the infusion set 200. In various embodiments, the septum retainer 242 is retained in the base 212 by septum retainer fingers 250, 252. However, in various other embodiments, other mechanisms for retention may be used. In some embodiments, the septum retainer 242 may be ultrasonically or otherwise welded into the base 212.

In various embodiments, the cannula 248 may be manufactured from the same material as the septum retainer 242 and in some embodiments, the cannula 248 and septum retainer 242 may be molded as a single part. In some embodiments, the cannula 248 may be funnel-shaped, as shown in FIG. 53C. In various embodiments, the cannula 248 may be attached to the septum retainer 242.

In various embodiments of the infusion set 200, the base 212 may include the septum retainer 242 which may include a retainer cutout 244. In various embodiments, the retainer cutout 244 may be round and/or conical in shape and may provide ample room for the cannula 248 to move about with respect to the base 212 when the base 212 moves due to the location on a user/patient's skin. In various embodiments, a retainer cutout 244 may be any shape or size including the shape and size shown in FIG. 53B. In various embodiments, the retainer cutout 244 may be beneficial/desirable for many reasons, including but not limited to, while the infusion set 200 may be attached to the user, when the user's skin moves, the retainer cutout 244 provides ample room such that the cannula 248 is not sheared. Thus, the retainer cutout 244 essentially moves the pivot point of the cannula 248 further away from the skin than it would be if the retainer cutout 244 were not included.

In various embodiments, the cannula 248 may be tapered and in some embodiments, the cannula 248 may not be tapered.

In various embodiments, an antiseptic or other topically introduced ointment, whether medicinal or nutritional or other, may be included in the retainer cutout 244. Thus, upon attachments of the infusion set 200 to the user, and insertion of the cannula 248, an antiseptic or other topically introduced ointment, whether medicinal or nutritional or other may be introduced onto the user's skin. This may be beneficial/desirable for many reasons, including, but not limited to, preventing infection and/or introducing medicine or nutriceuticals or nutritional compounds to the user in a convenient manner.

In various embodiments, the septum retainer 242 may include a needle guide 246 which guides the introduction needle 214 through the septum 208 and into the cannula 248. In various embodiments, the needle guide 246 may be any shape or size, including, but not limited to, the shape and size shown in FIG. 53B. In various embodiments, the needle guide 246 may be made from a different material from the septum retain 242. For example, in some embodiments, the needle guide 246 may be made from metal. In some embodiments, the cannula 248 may be press fit into the septum retainer 242 and then the metal needle guide 246 may be press fit into the septum retainer 242. In various embodiments, this method of manufacture provides an interference fit.

Figure 54A:
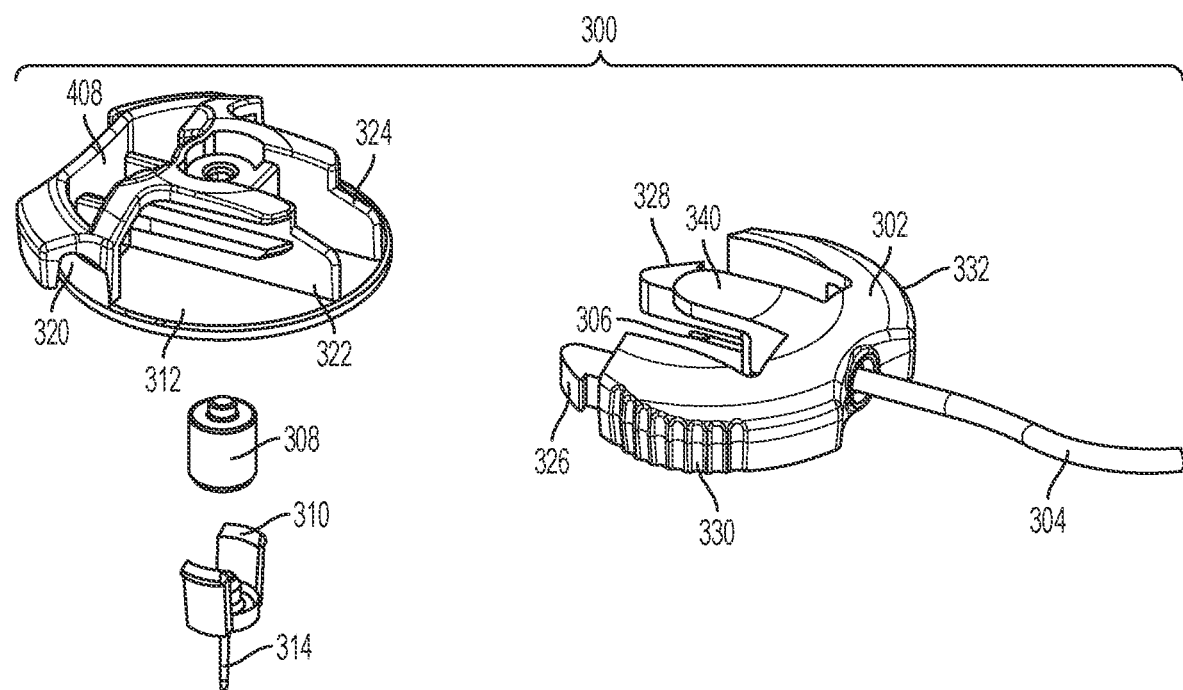
FIGS. 54A-54B are various views of one embodiment of an infusion set.
Figure 54B:
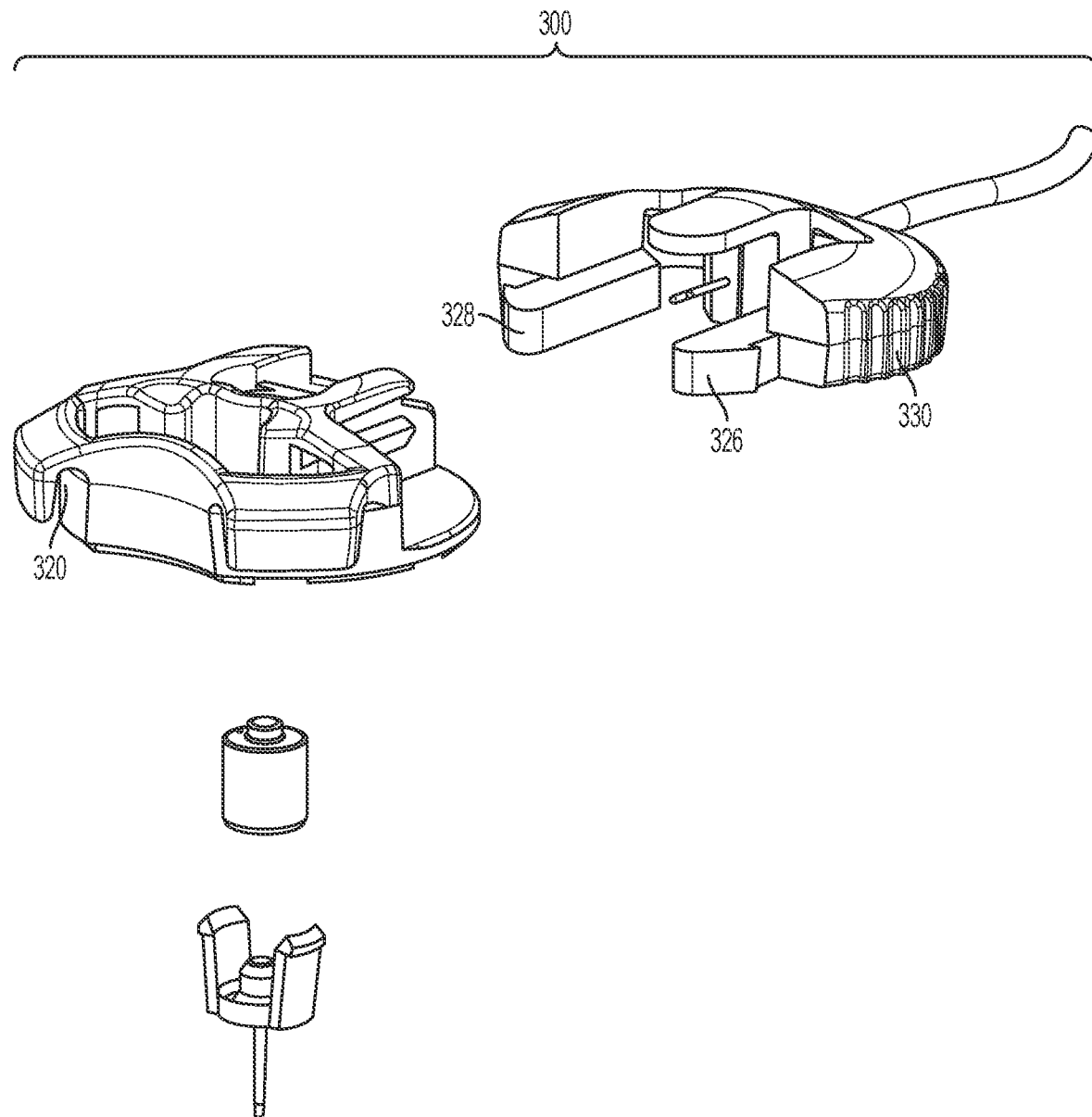
Figure 55A:
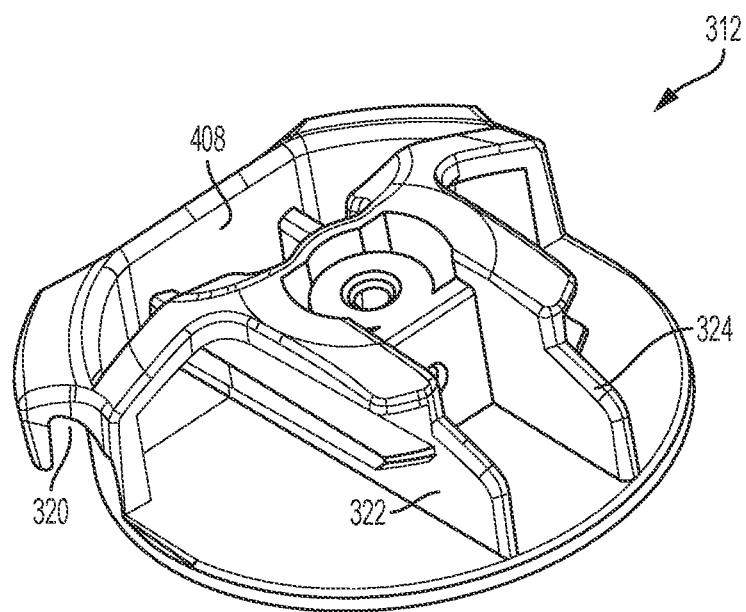
FIGS. 55A-55C are various views of one embodiment of a base for an infusion set.
Figure 55B:
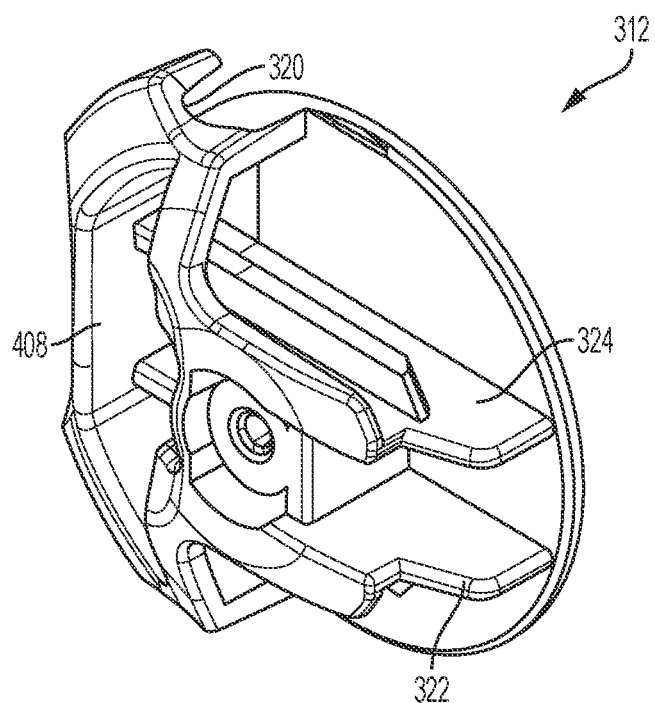
Figure 55C:
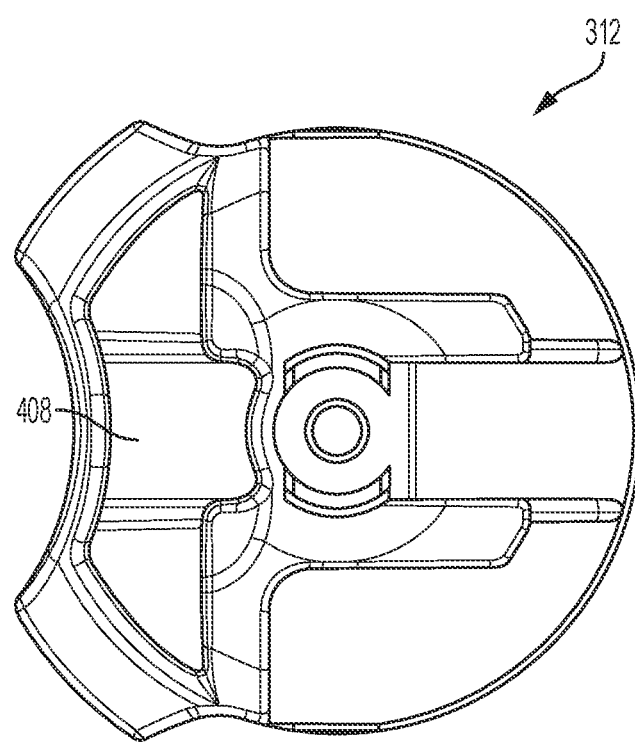

Referring now also to FIGS. 54A-54B, another embodiment of an infusion set 300 is shown. In various embodiments, the infusion set 300 includes a connector 302, tubing 304/a predetermined length of tubing 304, a connector needle 306, a septum 308, a septum retainer 310, a base 312, a cannula 314 and an introduction needle 306. The connector 302 includes a connector needle 306 which, when brought into contact with the base 312 is inserted through the septum 308 such that it is in fluid communication with the cannula 314. In addition, in some embodiments, one which is shown in FIG. 5, the infusion set may additionally include a funnel 28 which, in various embodiments, may be desirable/beneficial for it functions as a needle guide to guide the introduction needle 26.

Still referring to FIGS. 54A-54B and also to FIGS. 55A-55C and FIGS. 56A-56B, in various embodiments, the septum 308 is press fit into the base 312 and the septum retainer 310, introduction needle 26 (not shown see for example FIG. 5), and funnel 28 (not shown see for example FIG. 5) are also press fit into the base 312. In various embodiments, the base 312 includes a cutout area 320. The cutout area 320 is configured to accommodate a length of tubing 304 as it is wrapped around the infusion set 300. This may be beneficial/desirable for many reasons, including, but not limited to, preventing kinking of the tubing 304, as once the tubing 304 is wrapped around the infusion set 300, when pulled in various directions or at an angle, the tubing may have less chances of kinking, and kinking may cause occlusions. In various embodiments, the cutout area 320 functions as a tubing organizer.

In various embodiments, the tubing 304 may wrap around the infusion set 300 and may be clipped or otherwise secured in place. The clipping or securing may be done in any direction. Thus, in various embodiments, the wrapping the tubing around the infusion set 300 may allow changing the direction of the tubing 304. In some embodiments, the tubing 304 may be routed underneath the infusion set 300 to change the direction.

In various embodiments, the base 312 includes a finger grip area 408, which, in some embodiments, is a concave area in the base 312 that is configured for finger grip stability while connecting of disconnecting the base 312 from the connector 302. In various embodiments, the back edge of the base 312 is curved inwards and a portion of the base is carved out to form a concave slot or area that may be used as a finger grip or finger hold. This may be beneficial/desirable for many reasons including but not limited to allowing for more stable finger force to be exerted onto the base which is beneficial/desirable during connection and disconnection from the connector 302.

In various embodiments, the base 312 includes an adhesive layer on the bottom. However, in various other embodiments, the base 312 may not include an adhesive layer on the bottom. In some embodiments, the adhesive layer may be covered with a paper or other to prevent exposure of the adhesive prior to adhering to a user/patient's skin. Prior to adhering to the skin, the paper or other may be removed and the base 312 may be pressed against the user/patient's skin. The adhesive maintains the base 312 on the skin.

In some embodiments, an adhesive layer may be included on an inserter device such as one of the various embodiments described herein. In some embodiments of these embodiments, as the infusion set is pushed towards the user, the infusion set comes into contact with an adhesive layer. In some embodiments, however, an adhesive layer may be located on both the inserter and the infusion set or on only the inserter or only the inserter device.

Referring also now to FIG. 1, in various embodiments of the infusion set 300 shown in, for example, FIGS. 54A-54B, the base 312 may include a retainer cutout 32. In various embodiments, the retainer cutout 32 may be conical in shape and may provide ample room for the cannula 314 to move about with respect to the base 312 when the base 312 moves due to the location on a user/patient's skin. In various embodiments, a retainer cutout 32 may be any shape or size including the shape and size shown in FIG. 1. In various embodiments, the retainer cutout 32 may be beneficial/desirable for many reasons, including but not limited to, while the infusion set 300 may be attached to the user, when the user's skin moves, the retainer cutout 32 provides ample room such that the cannula 314 is not sheared. Thus, the retainer cutout 32 essentially moves the pivot point of the cannula 24 further away from the skin than it would be if the retainer cutout 32 were not included.

Still referring to FIGS. 54A-54B, in various embodiments, the cannula 314 may be tapered and in some embodiments, the cannula 24 may not be tapered. An embodiment of the base 312 and connector 302 are shown. The base 312, in some embodiments, includes an adhesive layer (not shown, shown as 46 in FIG. 8), which, as discussed above, may also include a liner/paper or other to protect the adhesive layer 46. The base 312 includes connector receivers 322, 324 that are configured to receive connector fingers 326, 328. The connector fingers 326, 328 slide into the connector receivers 322, 324 and snap or lock into place such that once snapped or locked into place, the connector 302 and the base 312 are joined or mated and will not become unjoined or unmated until or unless the connector releases 330, 332 are pressed towards each other. Pressing the connecting releases 330, 332 towards each other releases the connector fingers 326, 328 such that they may be removed from the connector receivers 322, 324.

Figure 58:
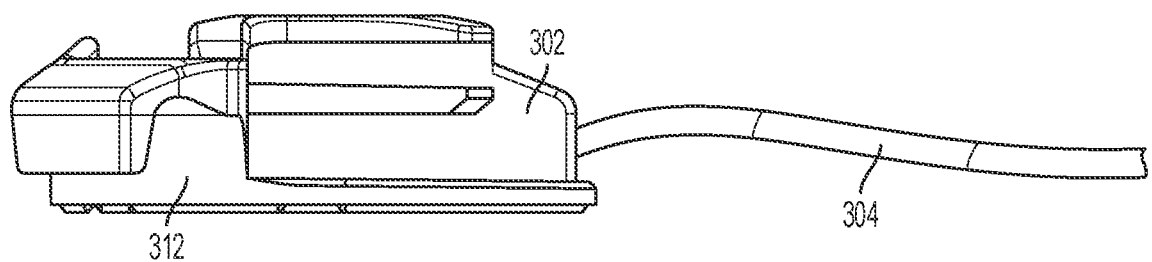
FIG. 58 is a view of one embodiment of an infusion set.

Referring now also to FIG. 58, by sliding the connector fingers 326, 328 of the connector 302 into the connector receivers 322, 324 on the base 312, the connector 302 is removably attached to the base 312. This action additionally causes the connector needle 306 to pierce the septum 308 of the base 312 such that the connector needle 306 is fluidly connected to the cannula 314. Once the connector needle 306 is fluidly connected to the cannula 314, fluid flowing from, for example, an infusion pump or other supply of fluid and through the tubing 304 (which, in various embodiments, may be fluidly connected to a reservoir in an infusion pump), may flow through the cannula 314 and into the user/patient.

Still referring to FIGS. 54A-54B and FIGS. 57A-57B, in various embodiments the connector 302 may include a connector needle protector 340. The embodiment of the connector 302 shown in FIGS. 57A-57B do not include a connector needle, however, an embodiment of the connector 302 with a connector needle 306 is shown in FIGS. 54A-54B. In various embodiments, the embodiments of the connector 302 shown in FIGS. 57A-57B may include a connector needle, for example, such as shown in FIGS. 54A-54B.

The connector needle protector 340, in various embodiments, is made from the same material as the connector 302, but in some embodiments may be made from a different material as the connector 302. In various embodiments, the connector needle protector 340 is shaped and sized as shown, however, the connector needle protector 340 may, in various embodiments, be any size or shape desired. The connector needle protector 340 may be beneficial/desirable for many reasons, including but not limited to, the connector needle protector 340 may prevent or diminish the risk of undesired needle sticks by user's or user caregivers and/or may prevent connector needle sticks that lead to contamination of the connector needle and therefore risk of contamination of user's and/or fluid delivered through the connector needle.

In various embodiments, the connector 302 includes ribbing or grip-related features on one or more areas of the connector 302. In various embodiments the connector 302 includes ribbing or grip-related features on the connector releases 330, 332. In some embodiments, the ribbing may include more or less pronounced ribs than shown and or more of less ribs than shown. In various embodiments, grip-related features may include nubs, textured surface and any other grip-related feature. In various embodiments, the ribbing and/or any grip-related feature may be convex or concave with respect to the connector 302 surface. For example, in the embodiment shown in FIGS. 54A-54B, the ribbing is convex. However, in other embodiments, the ribbing may be concave and in some embodiments the grip-related features and/or the ribbing may include section of concave and convex features.

Figure 56A:
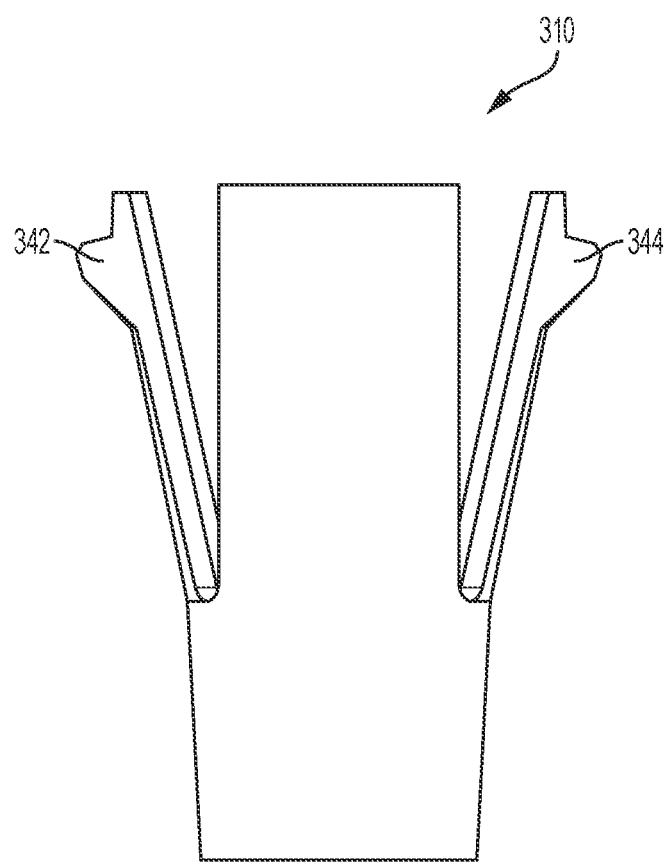
FIGS. 56A-56B are various views of one embodiment of a septum retainer.
Figure 56B:
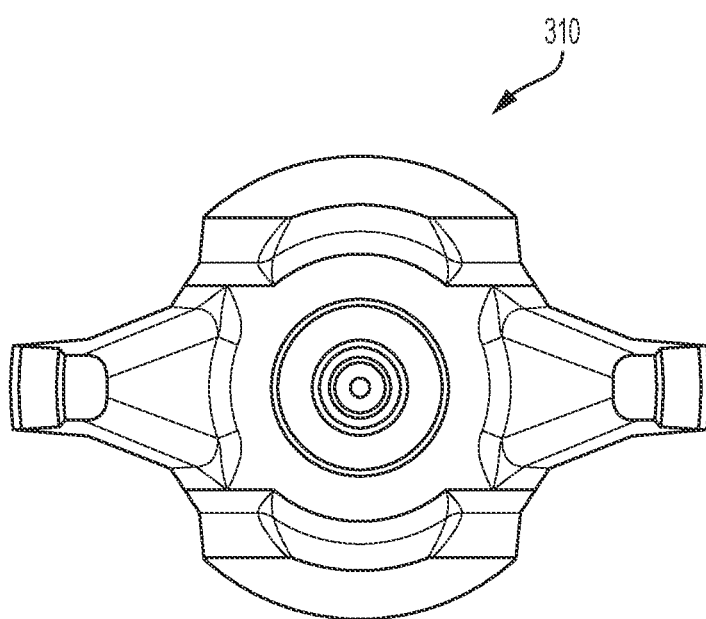
Figure 57A:
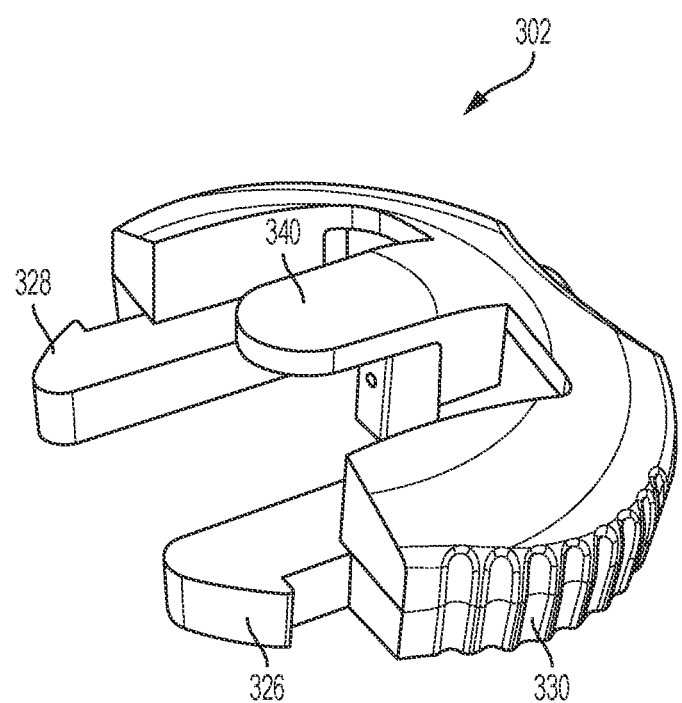
FIGS. 57A-57B are various views of one embodiment of a connector for an infusion set.
Figure 57B:
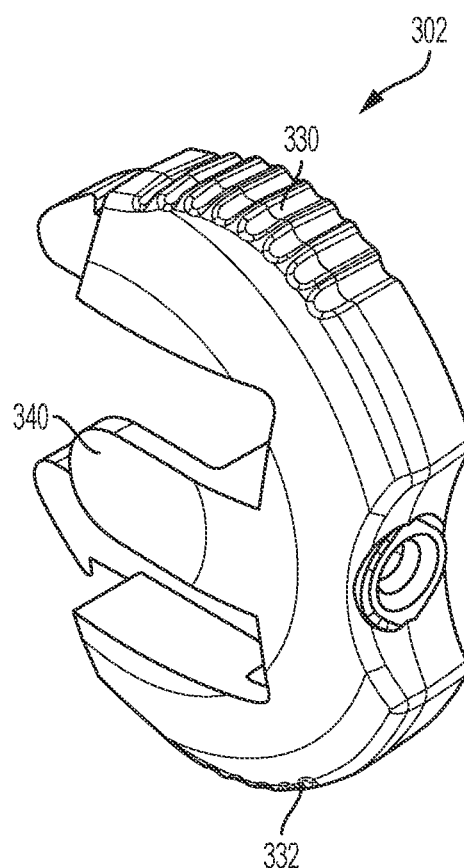

Referring now also to FIGS. 56A-56B, in some embodiments, the septum retainer 310 may be shaped as shown in FIGS. 56A-56B, but in some embodiments, the septum retainer 310 may be shaped as otherwise disclosed herein. In various embodiments, the septum retainer 310 is press fit into the base 312 of the infusion set 300. In various embodiments, the septum retainer 310 is retained in the base 312 by septum retainer fingers 342, 344. However, in various other embodiments, other mechanisms for retention may be used. In some embodiments, the septum retainer 310 may be ultrasonically or otherwise welded into the base 312.

Referring now also to FIGS. 54A-54B and FIGS. 56A-56B, in various embodiments, the cannula 314 may be manufactured from the same material as the septum retainer 310 and in some embodiments, the cannula 314 and septum retainer 310 may be ultrasonically welded, heat bonded or otherwise attached together.

Figure 51A:
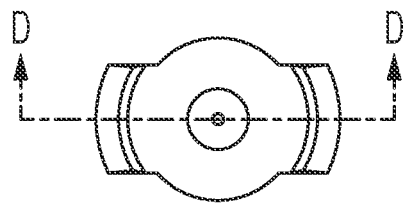
FIGS. 51A-51D are various views of one embodiment of a septum retainer.
Figure 51B:
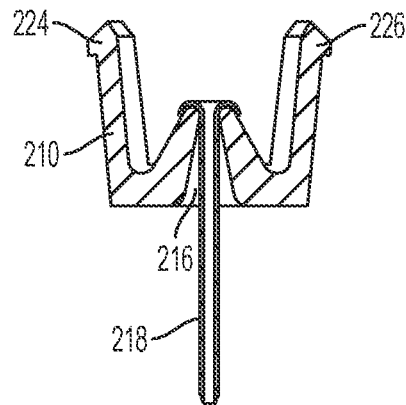
Figure 51C:
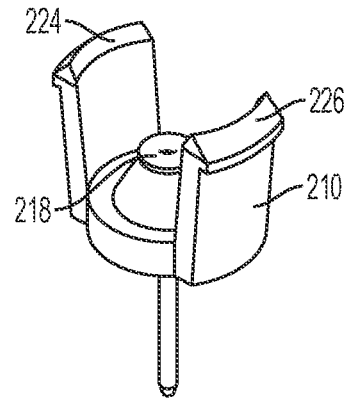
Figure 51D:
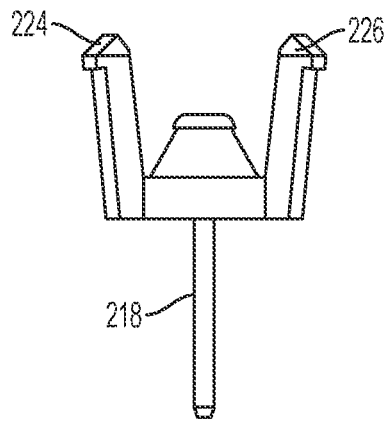
Figure 52A:
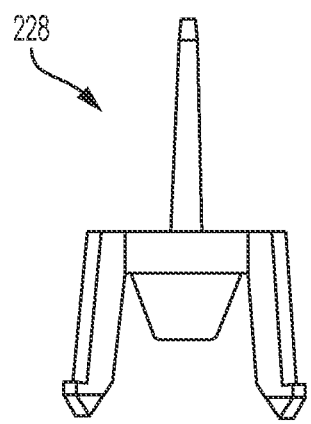
FIGS. 52A-52D are various views of one embodiment of a septum retainer.
Figure 52C:
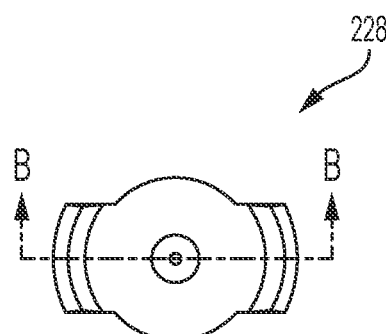
Figure 52B:
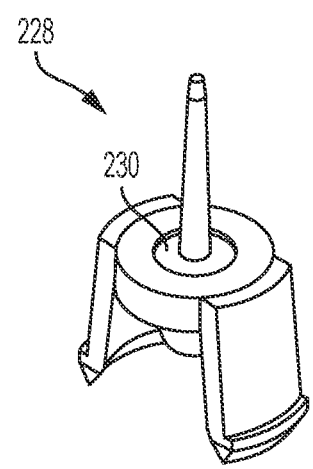
Figure 52D:
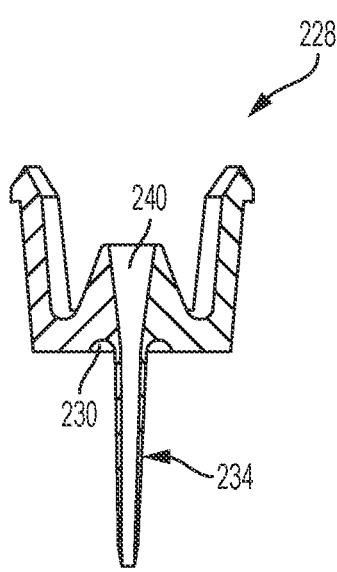

In various embodiments of the infusion set 300, the base 312 may include the septum retainer 310 which may include a retainer cutout (not shown, shown in FIG. 51B as 216). In various embodiments, the retainer cutout may be conical in shape and may provide ample room for the cannula 314 to move about with respect to the base 312 when the base 312 moves due to the location on a user/patient's skin. In various embodiments, a retainer cutout may be any shape or size including the shape and size shown in FIG. 51B. In various embodiments, the retainer cutout may be beneficial/desirable for many reasons, including but not limited to, while the infusion set 300 may be attached to the user, when the user's skin moves, the retainer cutout provides ample room such that the cannula 314 is not sheared. Thus, the retainer cutout essentially moves the pivot point of the cannula 314 further away from the skin than it would be if the retainer cutout were not included.

In the various embodiments of the infusion sets described above, the various embodiments exhibit many benefits and therefore, may be beneficial/desirable for many reasons including but not limited to the following. In various embodiments, the design of the infusion set prevents or reduces the chance of tubing kinking. Additionally, the infusion set designs allow for the tubing to extend from the cannula site at any angle which could, in various embodimens, allow for a short tubing, allow more comfortable and variable positioning, and allow such that there is no alignment with the infusion set required. Thus, the user may inser the infusion set at any angle or direction and still have the direction/position of the tubing desired.

In various embodiments, a retainer cutout is included, as described above. In some embodiments of these embodiments of the infusion set, an antiseptic or other topically introduced ointment, whether medicinal or nutritional or other, may be included. Thus, upon attachments of the infusion set to the user, and insertion of the cannula, an antiseptic or other topically introduced ointment, whether medicinal or nutritional or other may be introduced onto the user's skin. This may be beneficial/desirable for many reasons, including, but not limited to, preventing infection and/or introducing medicine or nutriceuticals or nutritional compounds to the user in a convenient manner.

Inserter Assembly

In various embodiments, an inserter assembly may be used to insert one or more embodiments of an infusion set, which includes embodiments of infusion sets described above/herein. The inserter assembly, in various embodiments, enables the introduction needle and cannula to be introduced into a user/patient through their skin such that the cannula is inserted through the skin and into the subcutaneous region of the user/patient.

In various embodiments, the inserter assembly, in practice, produces a vacuum such that the skin is pulled into the inserter assembly/towards the inserter assembly and towards the introduction needle/cannula assembly. The result is the introduction needle/cannula assembly piercing the user/patient's skin and the base of the infusion set being pressed onto the user/patient's skin.

This method of insertion of a cannula may be beneficial/desirable for many reasons. These include, but are not limited to, decreasing the amount of pain experienced by the user/patient during insertion of the introduction needle/cannula.

In various embodiments the inserter assembly does not produce a vacuum.

Figure 24:
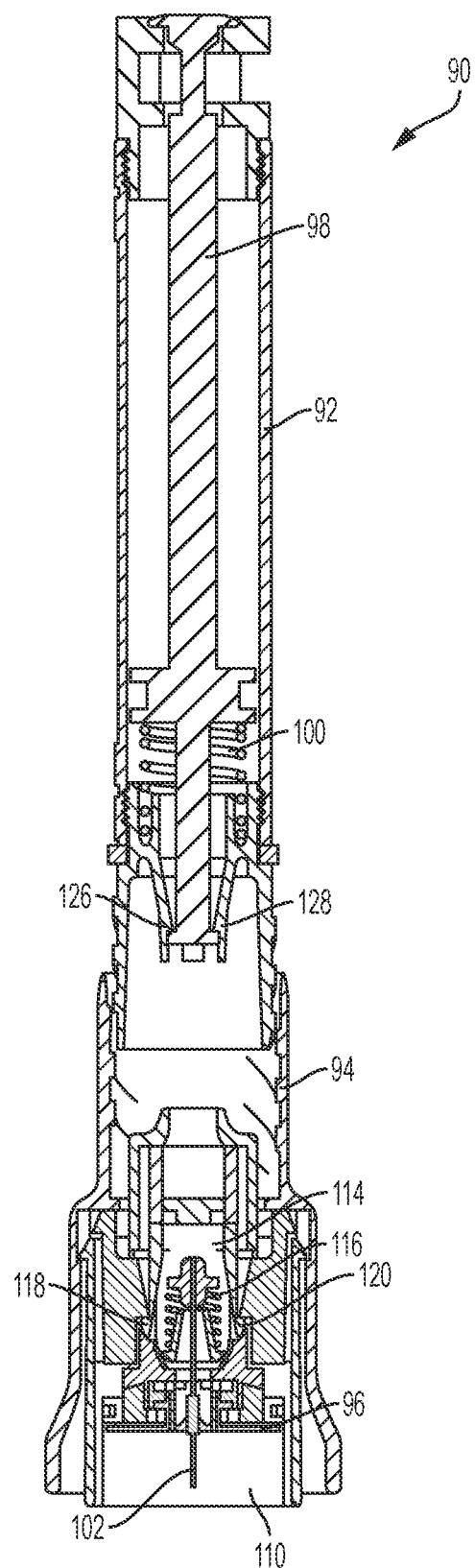

Referring now to FIGS. 23-33, one embodiment of an inserter assembly 90 shown. The inserter assembly includes a reusable inserter assembly portion 92, a disposable inserter assembly portion 94, and an infusion set 104 including an infusion set base 96. The reusable inserter assembly portion 92 includes a plunger 98 and a plunger spring 100. In a first position of the reusable inserter assembly portion 92, which may be seen in FIG. 23, the plunger 98 is in a first position. The reusable housing assembly portion 92 and disposable housing assembly portion 94 are not connected. Referring now also to FIG. 24, to begin the insertion of an introduction needle/cannula assembly 102, the plunger 98 is depressed to the second position. Depressing the plunger 98 also compresses the plunger spring 100 and the end of the plunger is locked in place by at least one, but in this embodiment at least four plunger locking fingers (see 126, 128, the other two are not visible in these views). The depressed plunger 98 is held in place by plunger locking fingers 126, 128. In various embodiments, the plunger locking fingers 126, 128 are spring-like fingers that are made from plastic. However, in other embodiments, various designs may be used to hold the depressed plunger 98 in the second position.

Figure 25:
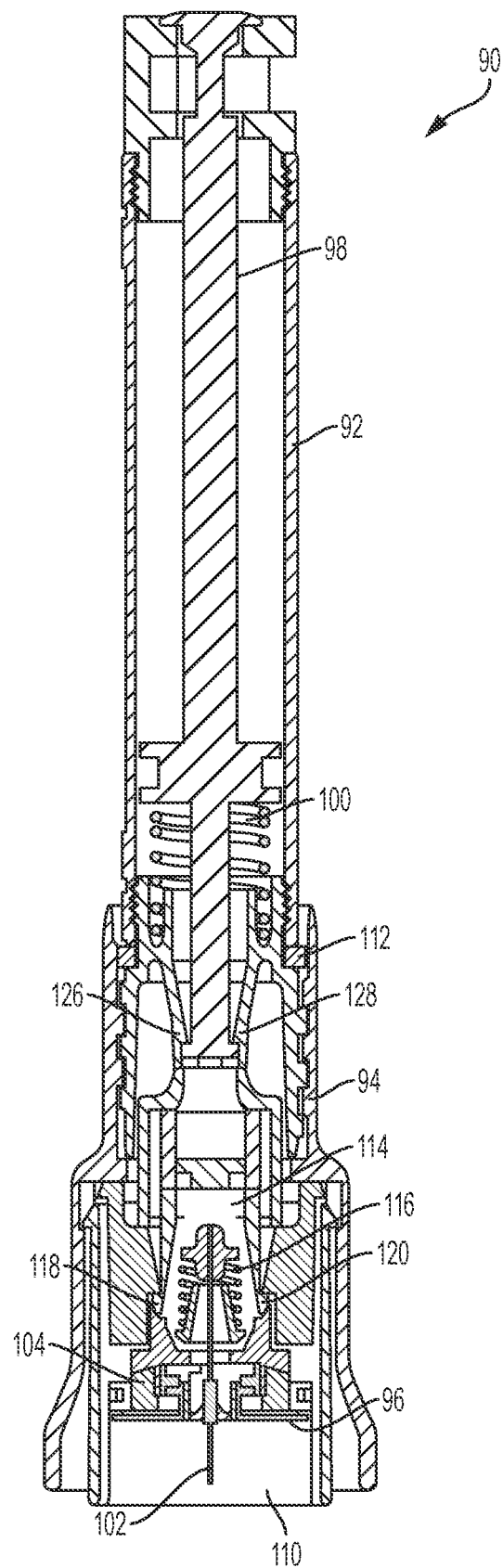
Figure 26:
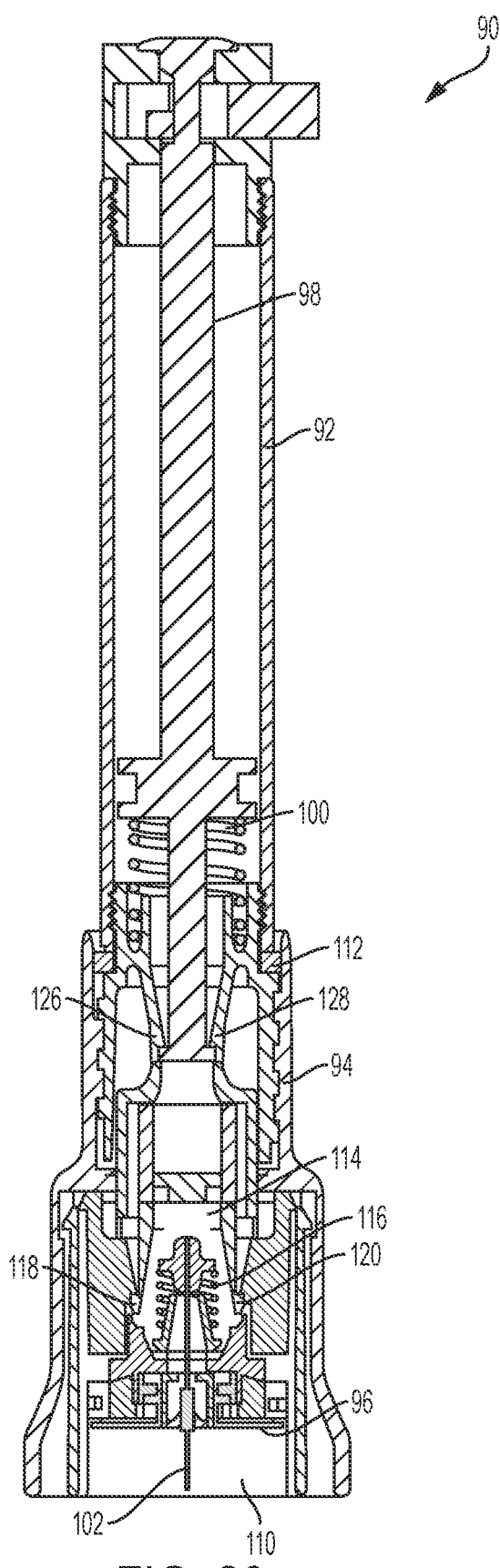
Figure 27:
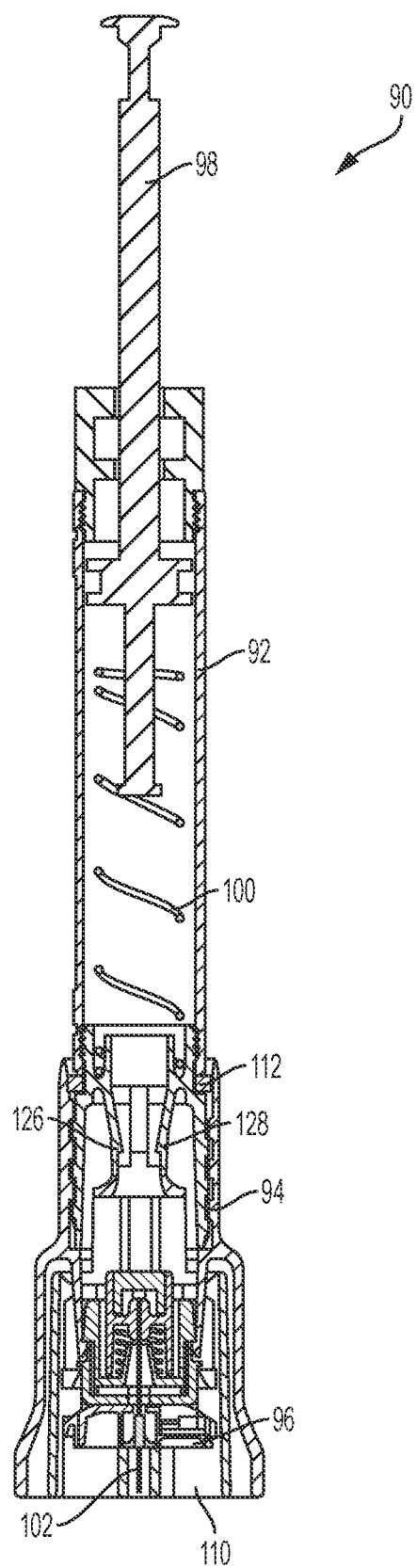
Figure 28:
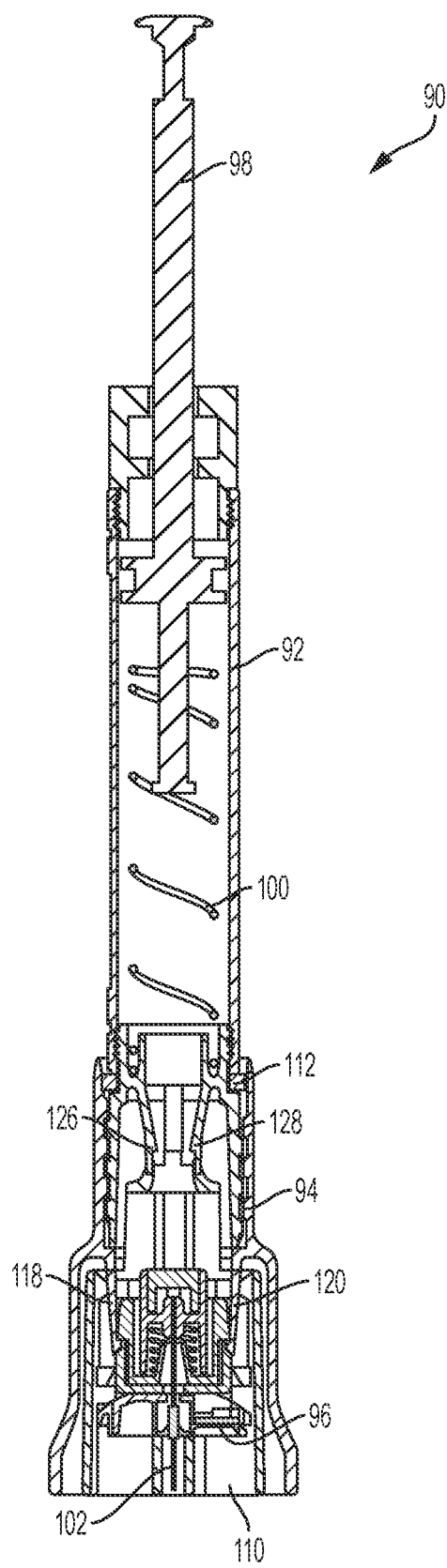
Figure 29:
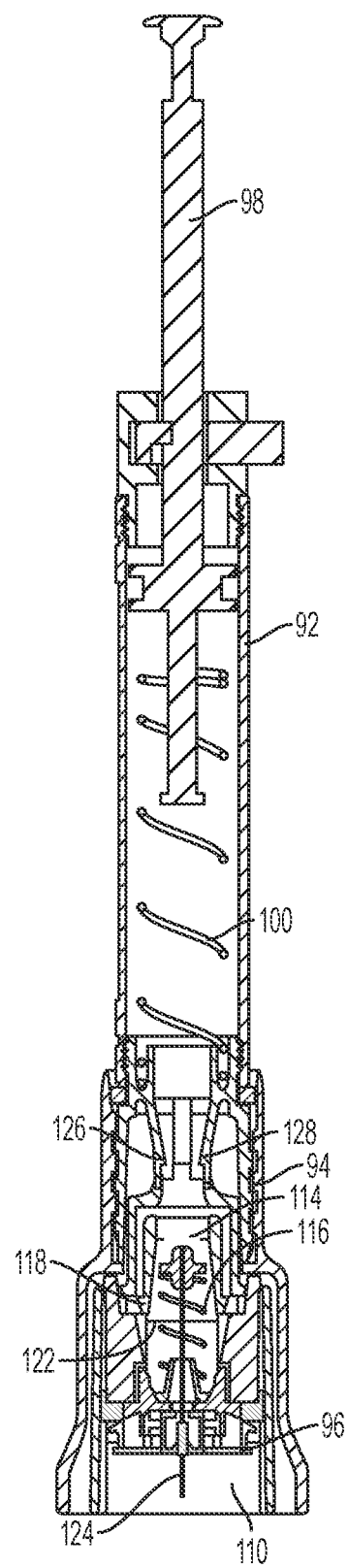
Figure 30:
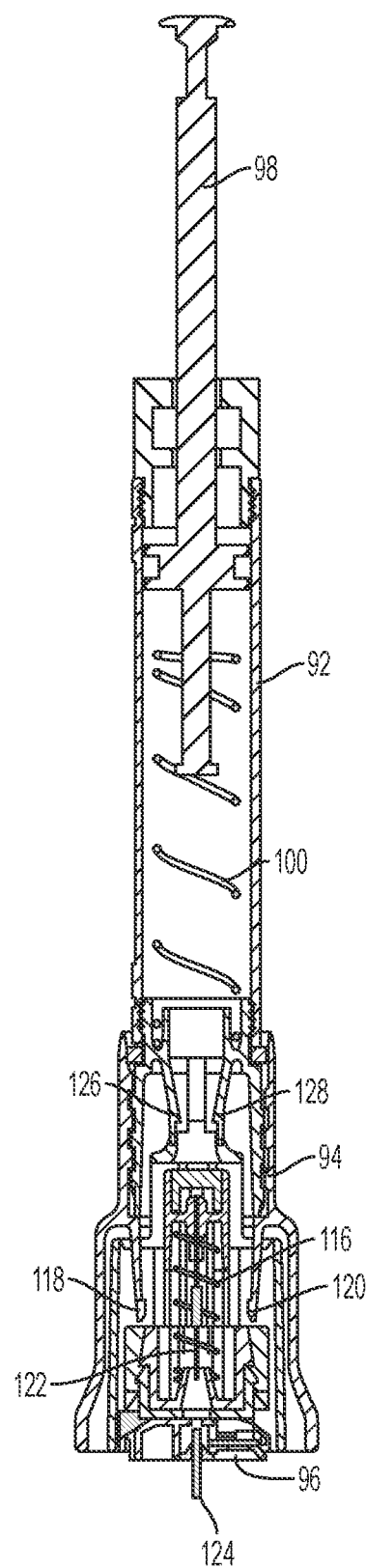

Referring now also to FIG. 25, the reusable housing assembly portion 92 and disposable housing assembly portion 94 are attached. In various embodiments, the attachment may be made by screwing the reusable housing assembly portion 92 onto the disposable housing assembly portion 94. In various embodiments, the connection between the reusable housing assembly portion 92 and the disposable housing assembly portion 94 is a removable connection, however, in other embodiments, the connection between these two portions 92, 94 may not be removable. Also, although described and shown as the reusable housing portion assembly 92 plunger 98 being depressed and in the second position before the reusable housing assembly portion 92 and the disposable housing assembly portion 94 are attached, in various embodiments, the reusable housing assembly portion 92 and the disposable housing assembly portion 94 may be attached prior to the plunger 98 being depressed into the second position.

In various embodiments, attaching the disposable inserter assembly portion 94 onto the reusable inserter assembly portion 92 creates a seal for a vacuum to create a suction on the user's/patient's skin. This is discussed in greater detail below.

Referring now also to FIG. 25, when the user/patient and/or caregiver desires to insert the introduction needle/cannula assembly 102 into the user/patient's skin, to begin the insertion, the insertion assembly 90 is held against and pressed towards the user's/patient's skin. This pushes the plunger release assembly 110 towards the plunger 98 which triggers the plunger's 98 release from the plunger locking fingers 126, 128. As the plunger spring 100 was compressed, the releasing the plunger 98 also allows the plunger spring 100 to be decompressed which propels the plunger 98 from the second position to the first position. The action of the plunger 98 moving quickly from the second position to the first position produces a vacuum within the disposable inserter assembly portion 94. An o-ring seal assembly 112 seals the disposable inserter assembly portion 94 to create a strong vacuum and also, creates a seal on the user's skin. The seals are all vacuum tight. In various embodiments, there may also be additional sealing assemblies, including, but not limited to, an o-ring/sealing assembly around the plunger 98. Although the seal assembly 112 is an o-ring in some embodiments, in other embodiments any seal assembly may be used, including, but not limited to, one or more o-rings, lip seals, or other sealing mechanisms.

The vacuum pulls the user's/patient's skin towards the introduction needle/cannula assembly 102 inside the disposable inserter assembly portion 94 and the introduction needle/cannula assembly 102 pierces the skin of the user/patient.

Still referring to FIGS. 23-33, the disposable inserter assembly portion 94 also includes a needle carrier 114, a needle carrier spring 116 and spring fingers 118, 120. The needle carrier 114 is connected to the introduction needle 122 portion of the introduction needle/cannula assembly 102. The needle carrier spring 116 is maintained in the compressed state by spring fingers 118, 120. When the spring fingers 118, 120 are released by the action of pressing the plunger release assembly 110 against the user/patient (i.e., the user's skin moves the infusion set and causes the spring fingers 118, 120 to release) the needle carrier spring 116 is decompressed which causes the needle carrier 114 to move away from the user/patient and towards the plunger 98, and the infusion set base 96 to move toward the user/patient and away from the plunger 98. This action causes the removal of the introduction needle 122 from the introduction needle/cannula assembly 102. The cannula 124 remains in the user/patient's skin and the action of the decompressing needle carrier spring 116 provides force onto the infusion set base 96 which, in some embodiments, includes adhesive on thus, the force aids the adhesive to adhering to the user/patient's skin.

Figure 31:
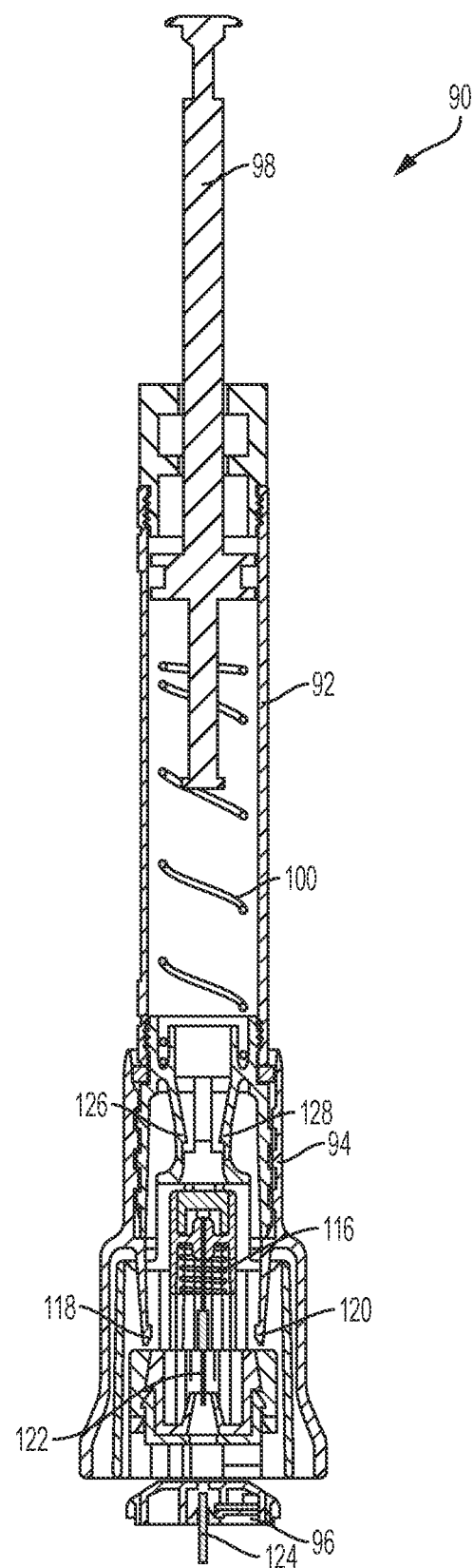
Figure 32:
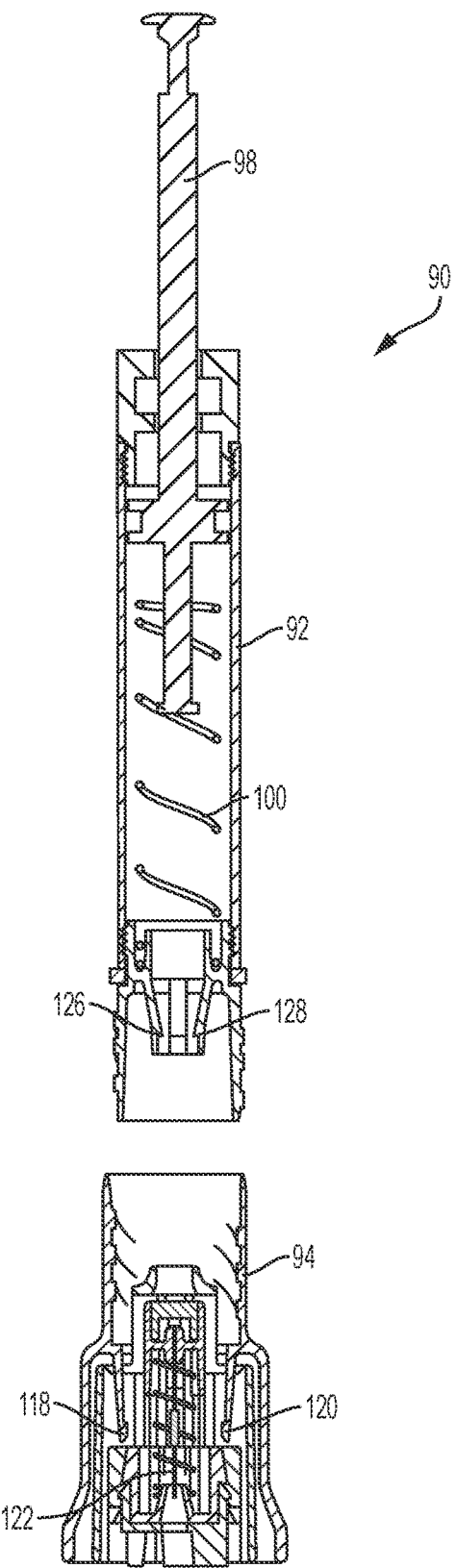
Figure 33:
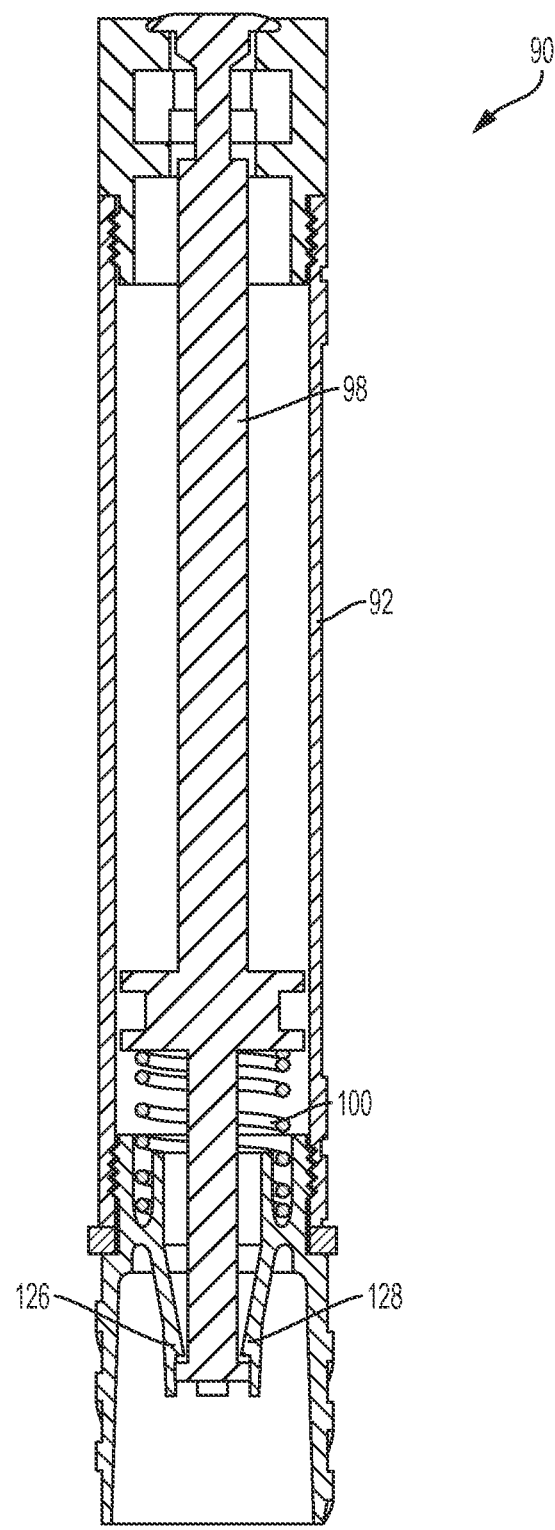
Figure 34:
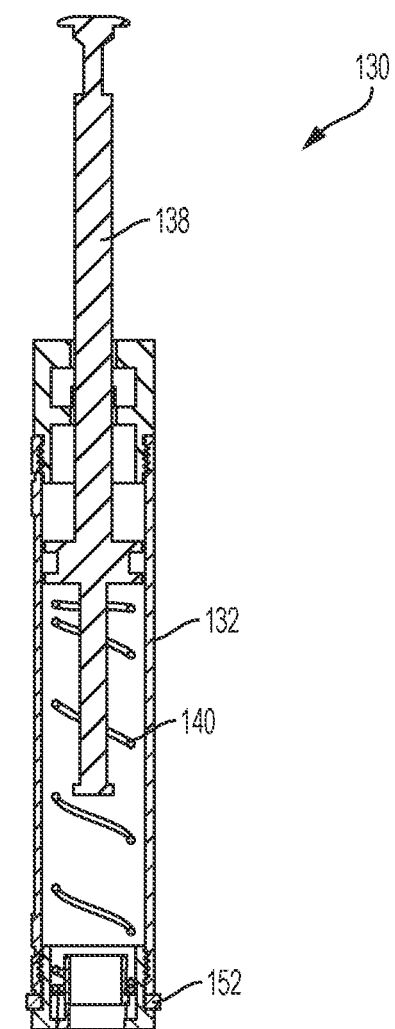
FIGS. 34-43 are various views of one embodiment of an infusion set inserter system.
Figure 34:
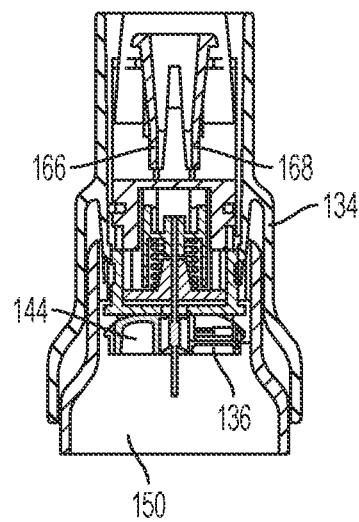

Referring now also to FIG. 31, once the infusion set base 96 is adhered to the user/patient, the infusion set base 96 is disassociated with the disposable inserter assembly portion 94 (See also, FIG. 32), and the reusable inserter assembly portion 92 may be removed from attachment to the disposable inserter assembly portion 94 by, for example, unscrewing the disposable inserter assembly portion 94 from the reusable inserter assembly portion 92.

The overall design of the inserter assembly 90 may be beneficial/desirable for many reasons, including but not limited to, the ability to reuse a large portion of the inserter assembly 90 while disposing only the portion that comes in contact with the user/patient's skin. Additionally, the disposable inserter assembly portion 94 retains the introduction needle 122 inside which therefore provides a sharps disposal to safely maintain the introduction needle 122 inside a plastic housing, preventing unintentional pricks.

Figure 35:
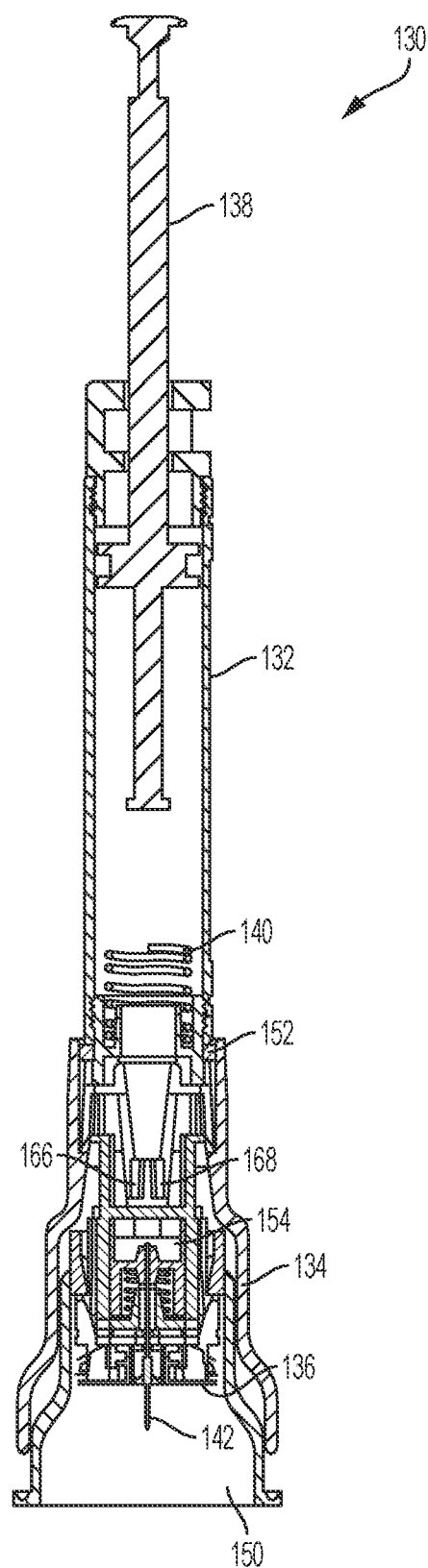
Figure 36:
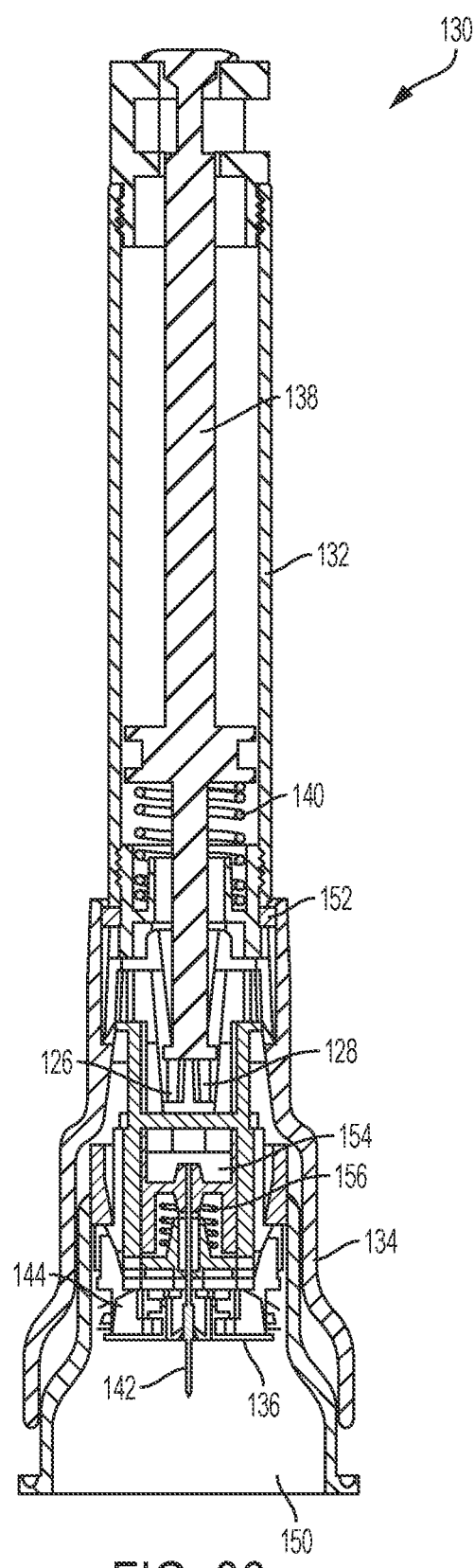
Figure 37:
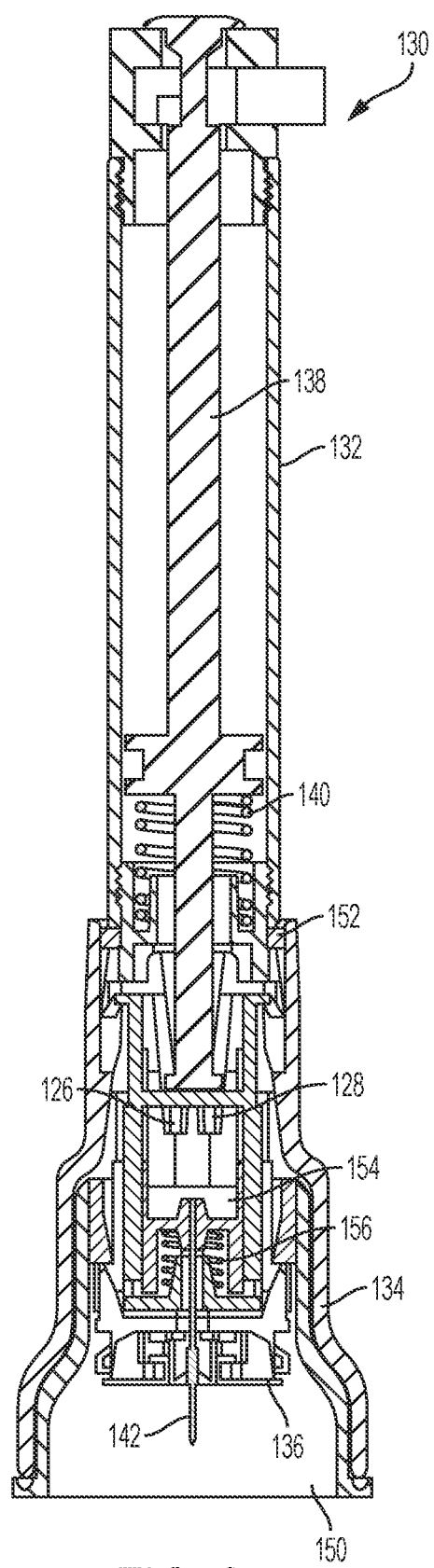
Figure 38:
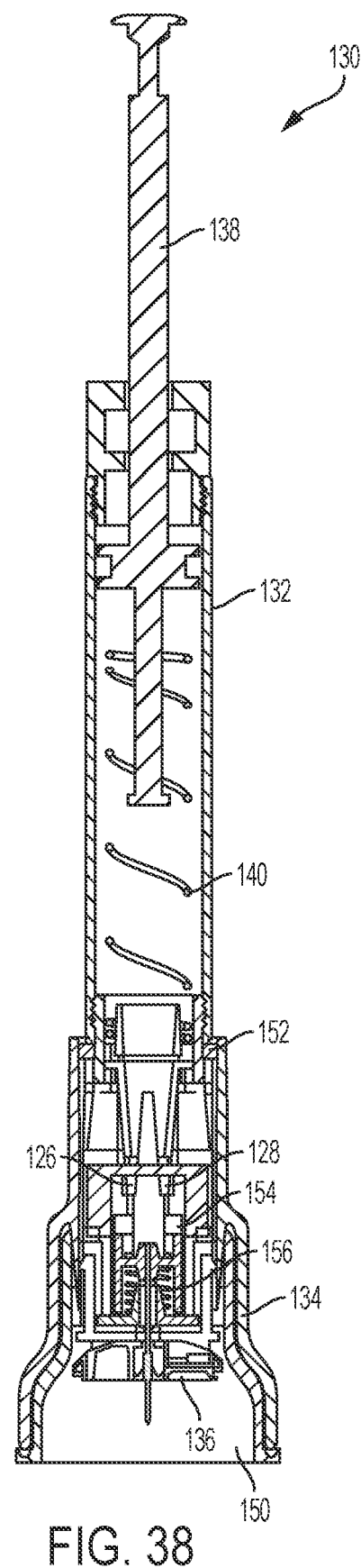
Figure 39:
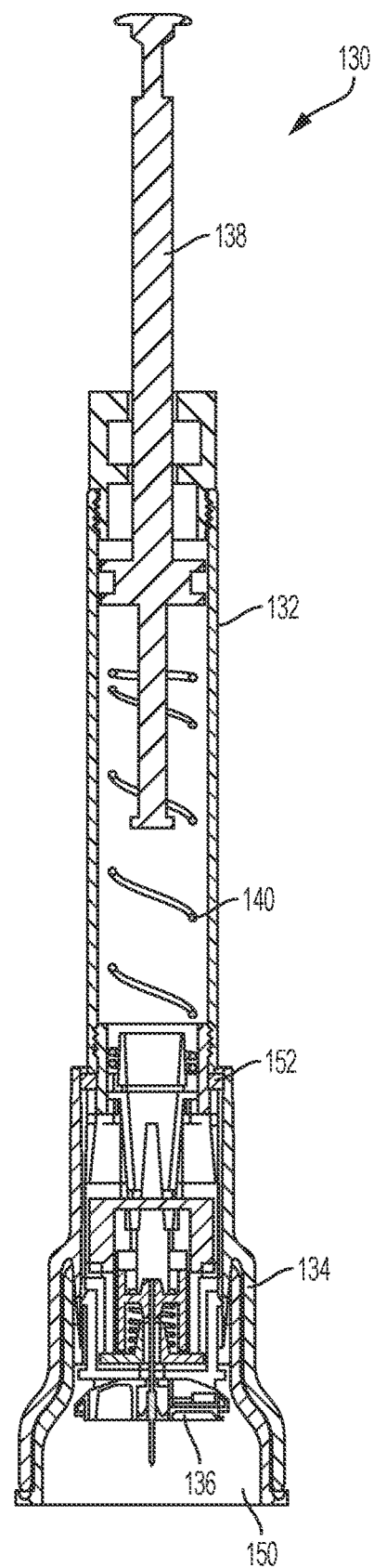
Figure 40:
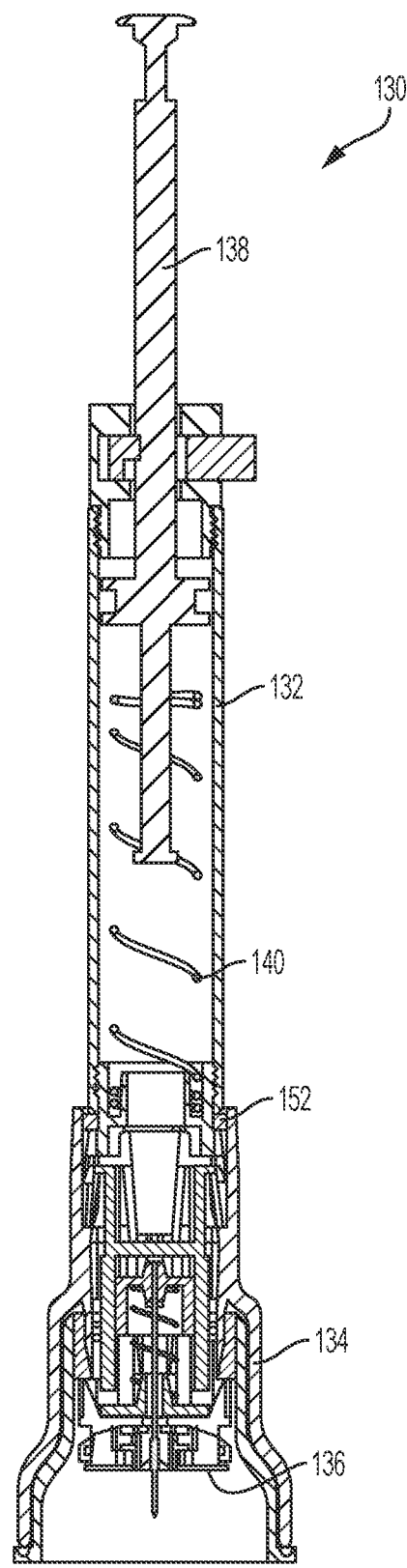
Figure 41:
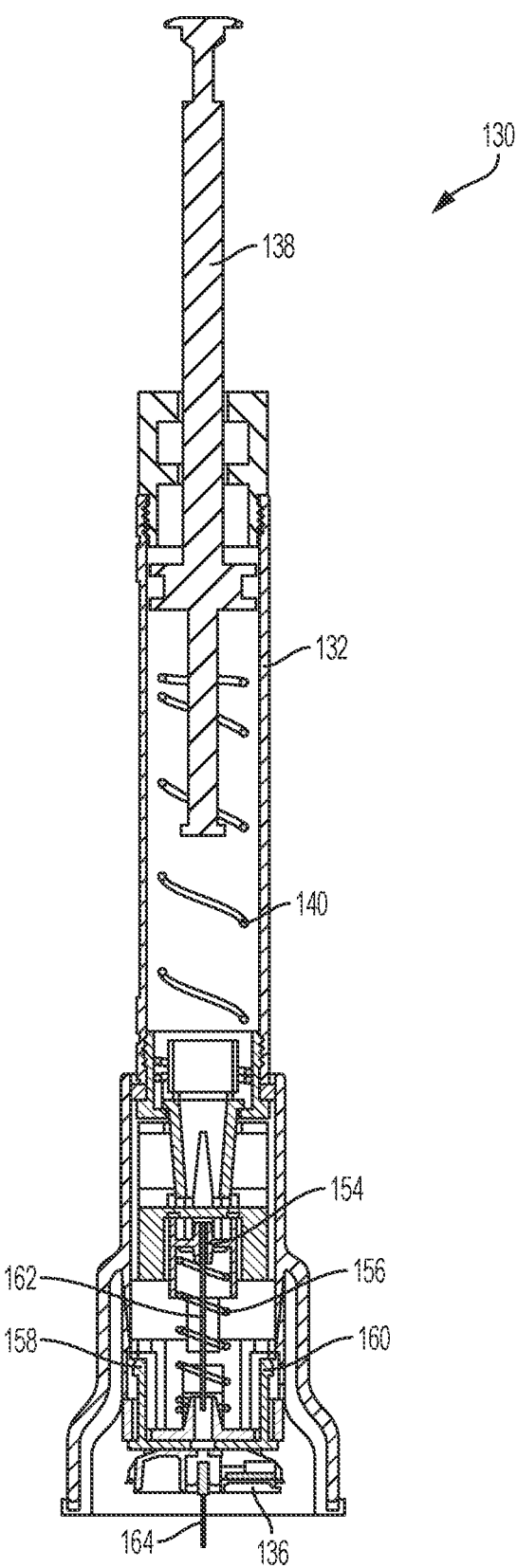

Referring now to FIGS. 34-43, another embodiment of an inserter assembly 130 shown. The inserter assembly includes a reusable inserter assembly portion 132, a disposable inserter assembly portion 134, and an infusion set 144 including an infusion set base 136. The reusable inserter assembly portion 132 includes a plunger 138 and a plunger spring 140. In a first position of the reusable inserter assembly portion 132, which may be seen in FIG. 34, the plunger 138 is in a first position. The reusable housing assembly portion 132 and disposable housing assembly portion 134 are not connected. Referring now also to FIG. 36, to begin the insertion of an introduction needle/cannula assembly 142, the plunger 138 is depressed to the second position. Depressing the plunger 138 also compresses the plunger spring 140 and the end of the plunger 138 is locked in place by at least one, but in this embodiment at least two plunger locking fingers 166, 168. The depressed plunger 138 is held in place by plunger locking fingers 166, 168. In various embodiments, the plunger locking fingers 166, 168 are spring-like fingers that are made from plastic. However, in other embodiments, various designs may be used to hold the depressed plunger 138 in the second position.

Referring now also to FIG. 35, the reusable housing assembly portion 132 and disposable housing assembly portion 134 are attached. In various embodiments, the attachment may be made by screwing the reusable housing assembly portion 132 onto the disposable housing assembly portion 134. In various embodiments, the connection between the reusable housing assembly portion 132 and the disposable housing assembly portion 134 is a removable connection, however, in other embodiments, the connection between these two portions 132, 134 may not be removable. Also, although described and shown as the reusable housing portion assembly 132 being attached to the disposable housing assembly 134 prior to the plunger 138 plunger 138 being depressed into the second position, in various embodiments, the embodiments shown in FIGS. 34-43 may be modified, in various embodiments, to allow for the plunger 138 to be depressed to the second position prior to the reusable housing portion assembly 132 being attached to the disposable housing assembly 134.

In various embodiments, attaching the disposable inserter assembly portion 134 onto the reusable inserter assembly portion 132 creates a seal for a vacuum to create a suction on the user's/patient's skin. This is discussed in greater detail below.

Referring now also to FIG. 35, when the user/patient and/or caregiver desires to insert the introduction needle/cannula assembly 142 into the user/patient's skin, to begin the insertion, the insertion assembly 130 is held against and pressed towards the user's/patient's skin. This pushes the plunger release assembly 150 towards the plunger 138 which triggers the plunger's 138 release from the plunger locking fingers 166, 168. As the plunger spring 140 was compressed, the releasing the plunger 138 also allows the plunger spring 140 to be decompressed which propels the plunger 138 from the second position to the first position. The action of the plunger 138 moving quickly from the second position to the first position produces a vacuum within the disposable inserter assembly portion 134. An o-ring seal assembly 152 seals the disposable inserter assembly portion 134 to create a strong vacuum. Although the seal assembly 152 is an o-ring in some embodiments, in other embodiments any seal assembly may be used, including, but not limited to, one or more o-rings, lip seals, or other sealing mechanisms.

The vacuum pulls the user's/patient's skin towards the introduction needle/cannula assembly 142 inside the disposable inserter assembly portion 134 and the introduction needle/cannula assembly 142 pierces the skin of the user/patient.

Still referring to FIGS. 34-43, the disposable inserter assembly portion 134 also includes a needle carrier 154, a needle carrier spring 156 and spring fingers 158, 160. The needle carrier 154 is connected to the introduction needle 162 portion of the introduction needle/cannula assembly 142. The needle carrier spring 156 is maintained in the compressed state by spring fingers 158, 160. When the spring fingers 158, 160 are released by the action of pressing the plunger release assembly 150 against the user/patient the needle carrier spring 156 is decompressed which causes the needle carrier 154 to move away from the user/patient and towards the plunger 138, and the infusion set base 136 to move toward the user/patient and away from the plunger 138. This action causes the removal of the introduction needle 162 from the introduction needle/cannula assembly 142. The cannula 164 remains in the user/patient's skin and the action of the decompressing needle carrier spring 156 provides force onto the infusion set base 136 which, in some embodiments, includes adhesive on thus, the force aids the adhesive to adhering to the user/patient's skin.

Figure 42:
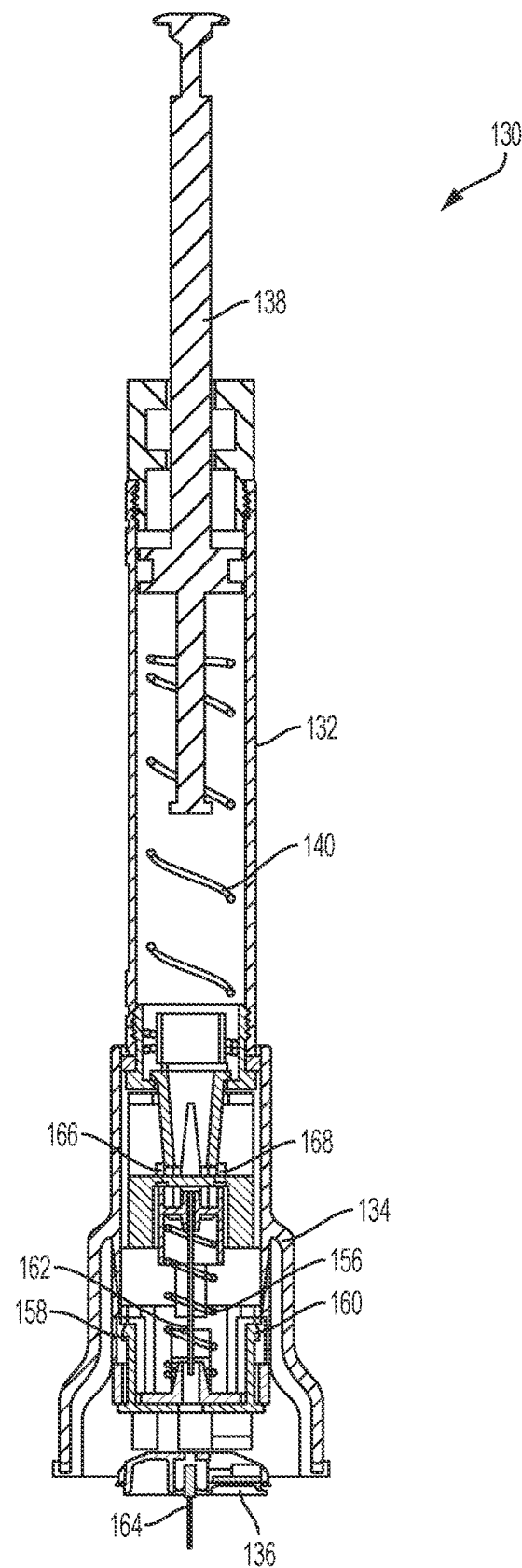
Figure 43:
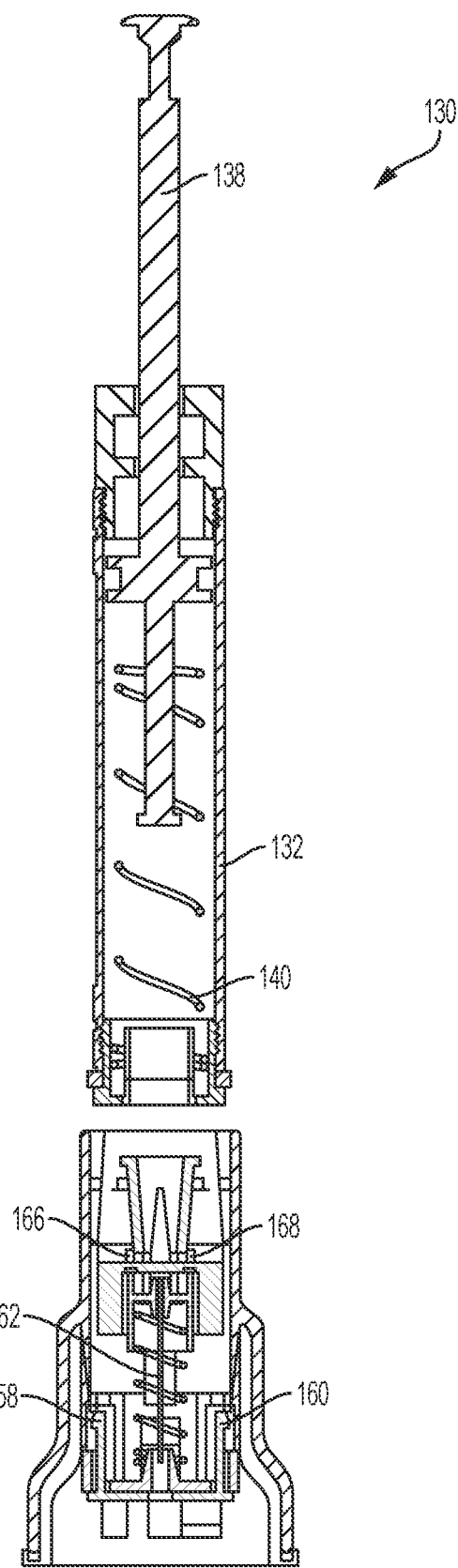
Figure 44:
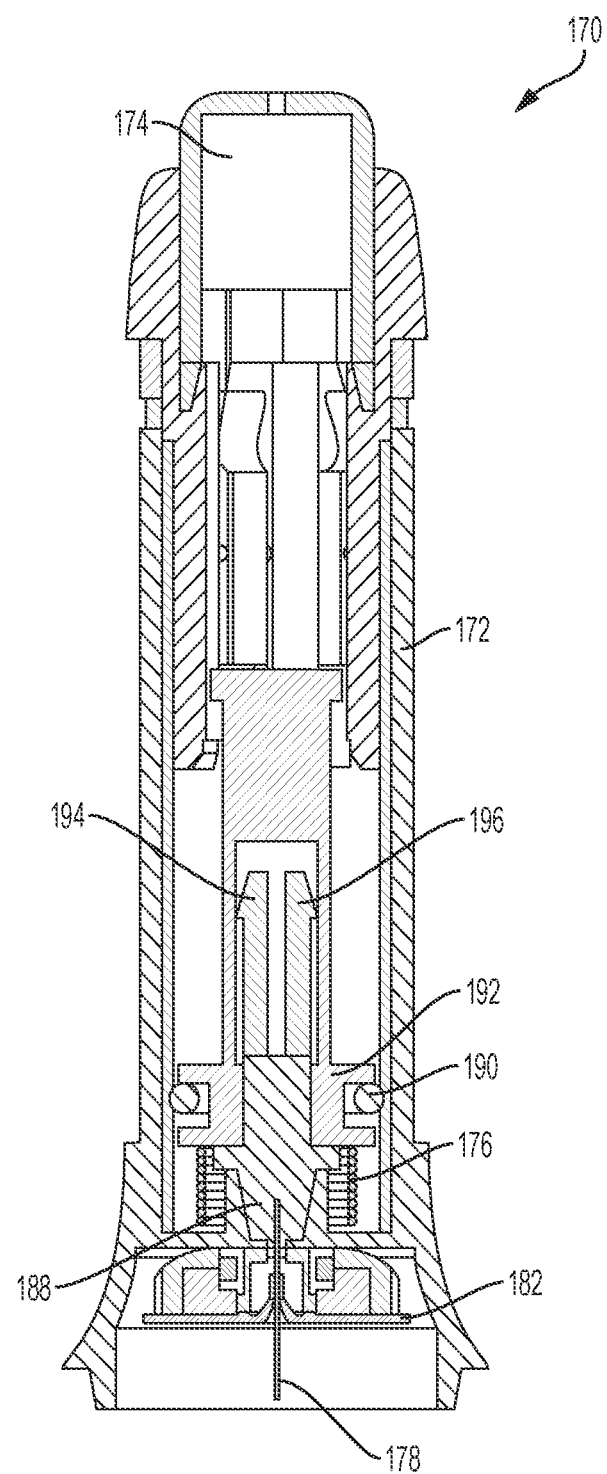
FIGS. 44-48 are various views of one embodiment of an infusion set inserter system.

Referring now also to FIGS. 42-43, once the infusion set base 136 is adhered to the user/patient, the infusion set base 136 is disassociated with the disposable inserter assembly portion 134 and the reusable inserter assembly portion 132 may be removed from attachment to the disposable inserter assembly portion 134 by, for example, unscrewing the disposable inserter assembly portion 134 from the reusable inserter assembly portion 132.

The overall design of the inserter assembly 130 may be beneficial/desirable for many reasons, including but not limited to, the ability to reuse a large portion of the inserter assembly 130 while disposing only the portion that comes in contact with the user/patient's skin. Additionally, the disposable inserter assembly portion 134 retains the introduction needle 162 inside which therefore provides a sharps disposal to safely maintain the introduction needle 162 inside a plastic housing, preventing unintentional pricks.

Referring now to FIGS. 44-48, another embodiment of an inserter assembly 170 shown. The inserter assembly 170 includes a housing portion 172, which is disposable after use and an infusion set 180 including an infusion set base 182. The housing portion 172 includes a plunger portion 192 and a plunger spring 176. In a first position of the housing portion 172, which may be seen in FIG. 44, the plunger portion 192 is in a first position.

Figure 45:
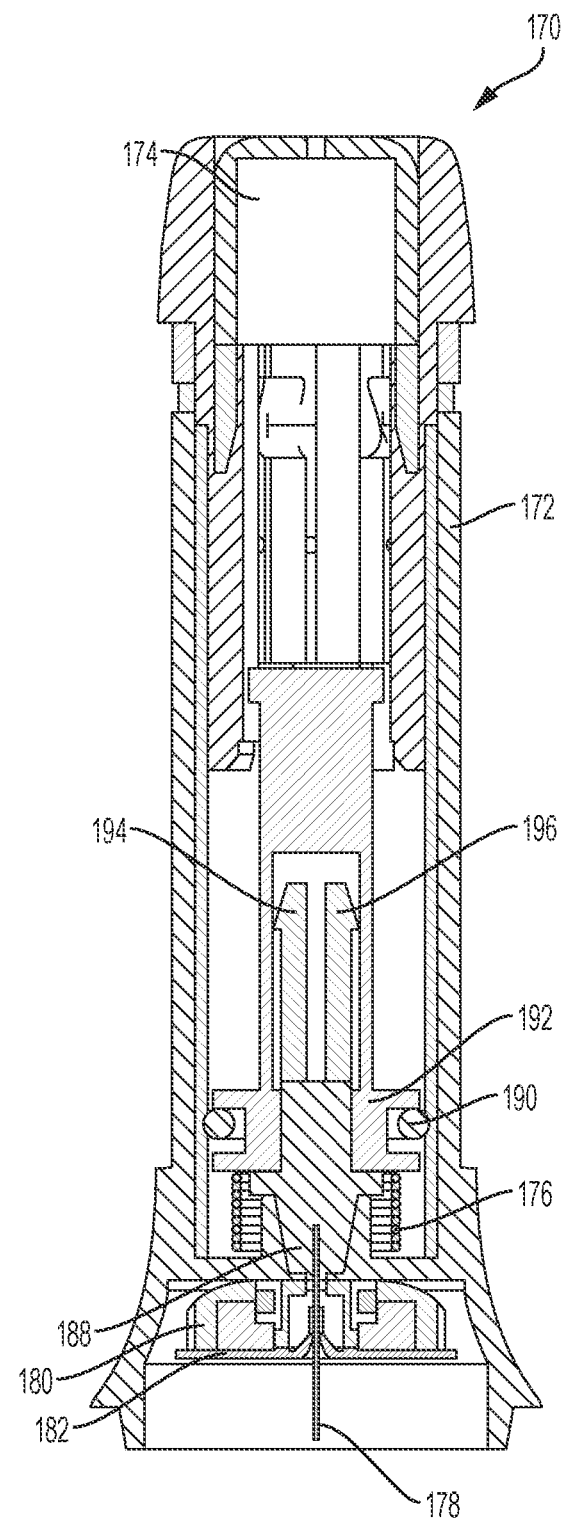

Referring now also to FIG. 45, when the user/patient and/or caregiver desires to insert the introduction needle/cannula assembly 142 into the user/patient's skin, to begin the insertion, the insertion assembly 130 is held against and pressed towards the user's/patient's skin. To begin the insertion of an introduction needle/cannula assembly 178, the button assembly 174 is depressed and the plunger portion 192 is released and begins to move to the second position.

Figure 46:
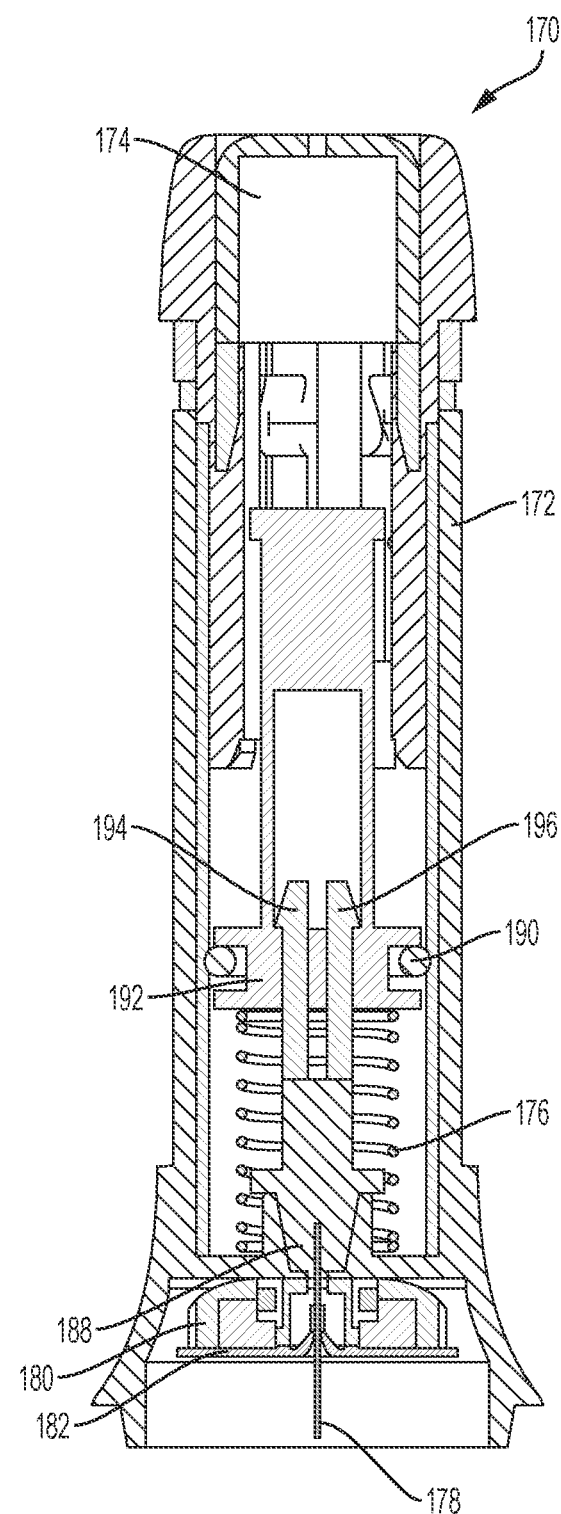
Figure 47:
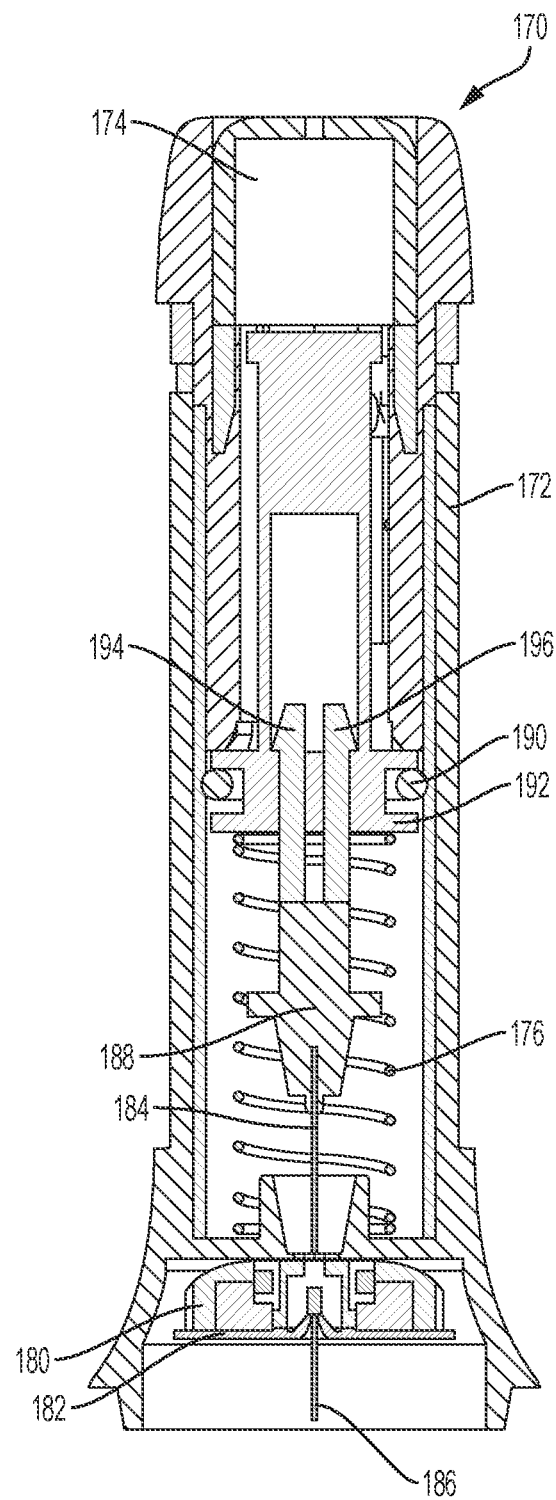
Figure 48:
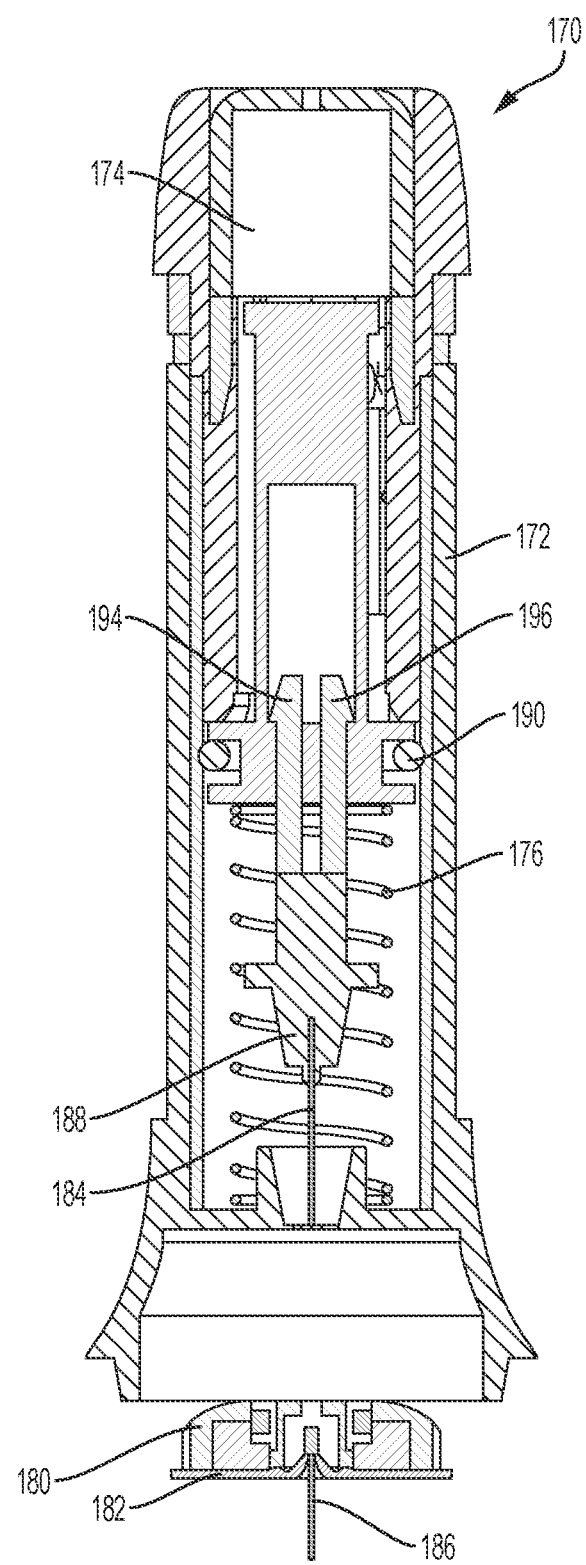
Figure 49:
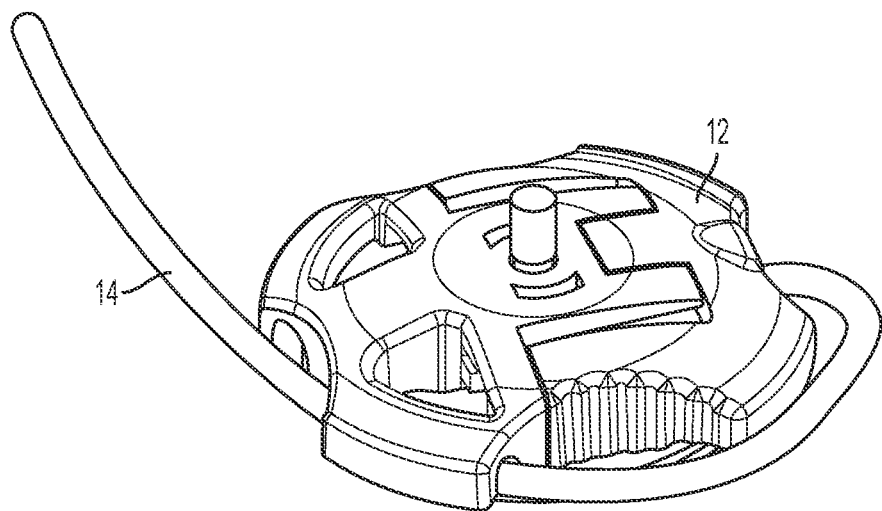
FIG. 49 is a view of one embodiment of an infusion set.
Figure 49:
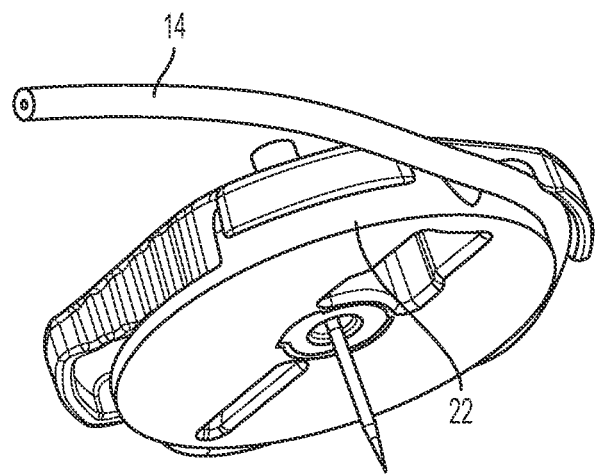

Referring now also to FIG. 46, the plunger portion 192 moves towards the button assembly 174 and away from the user/patient until the plunger portion 192 is stopped by locking fingers 194, 196. This is the second position of the plunger portion 192. The action of the plunger portion 192 moving quickly from the first position to the second position produces a vacuum within the housing portion 172. An o-ring seal assembly 190 seals the bottom part of the housing portion 172 to create a strong vacuum and also, creates a seal on the user's skin. The seals are all vacuum tight. In various embodiments, there may also be additional sealing assemblies, including, but not limited to, an o-ring/sealing assembly around the plunger portion 192. Although the seal assembly 190 is an o-ring in some embodiments, in other embodiments any seal assembly may be used, including, but not limited to, one or more o-rings, lip seals, or other sealing mechanisms.

The vacuum pulls the user's/patient's skin towards the introduction needle/cannula assembly 178 inside the housing portion 172 and the introduction needle/cannula assembly 178 pierces the skin of the user/patient.

Still referring to FIGS. 44-48, the housing portion 172 also includes a needle carrier 188. The needle carrier 188 is connected to the introduction needle 184 portion of the introduction needle/cannula assembly 178 and to the plunger spring 176. Once the plunger portion 192 is in the second position, the needle carrier 188 continues to move away from the user/patient and towards the plunger portion 192. The needle carrier 188 continues moving towards the bottom assembly 174 and away from the user/patient, removing the introduction needle 184 from the introduction needle/cannula assembly 178. The cannula 164 remains in the user/patient's skin and the infusion set base 182 of the infusion set 180 is adhered to the user/patient's skin.

Once the infusion set base 182 is adhered to the user/patient, the infusion set 180 is disassociated with the housing portion 174. The overall design of the inserter assembly 170 may be beneficial/desirable for many reasons, including but not limited to, the disposable housing portion 172 retains the introduction needle 184 inside which therefore provides a sharps disposal to safely maintain the introduction needle 184 inside a plastic housing, preventing unintentional pricks.

In various embodiments, the inserter may be a two-stage inserter that includes both the automated and/or mechanized insertion of the cannula and removal of the introduction needle, a sequence initiated by the single push of a single button or activation of a release mechanism. Thus, once the sequence is initiated, the inserter will insert the cannula and remove the introduction needle in consecutive stages, without any further interaction by the user with the inserter. Additionally, in various embodiments described herein, at the end of the second stage, i.e., removal of the introduction needle from the user's body, the introduction needle is nested inside the inserter device/inserter housing. This provides for an built in sharps container and also eliminated the user interaction and/or user exposure to the introduction needle. Single button or single release mechanism two-stage inserters may be desirable/beneficial for many reasons including but not limited to the improved ease, comfort and convenience of a user simply pushing a button or releasing a release mechanism and the cannula being inserted without any further interaction, including but not limited to, the manual removal of the introduction needle. This may be beneficial/desirable for many reasons, including, but not limited to, eliminating the manual removal of the introduction needle will decrease the opportunity of the user to visualize the introduction needle which may reduce user anxiety of insertion of the cannula and will reduce and/or eliminate the opportunity of unintended introduction needle sticks either by the user or a caregiver.

Figure 59:
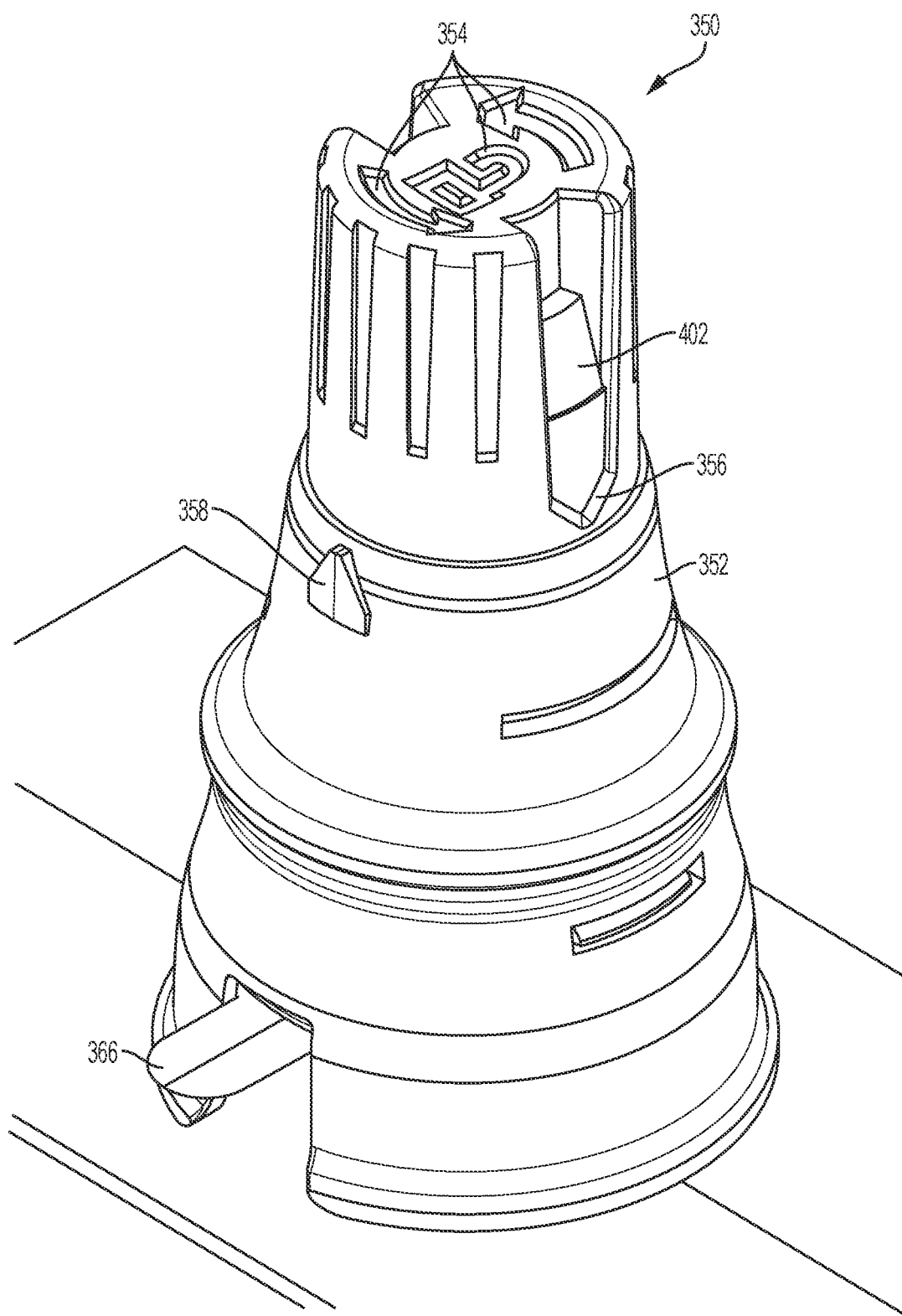
FIGS. 59-71 are various views and configurations of an inserter assembly/infusion set inserter system.
Figure 60:
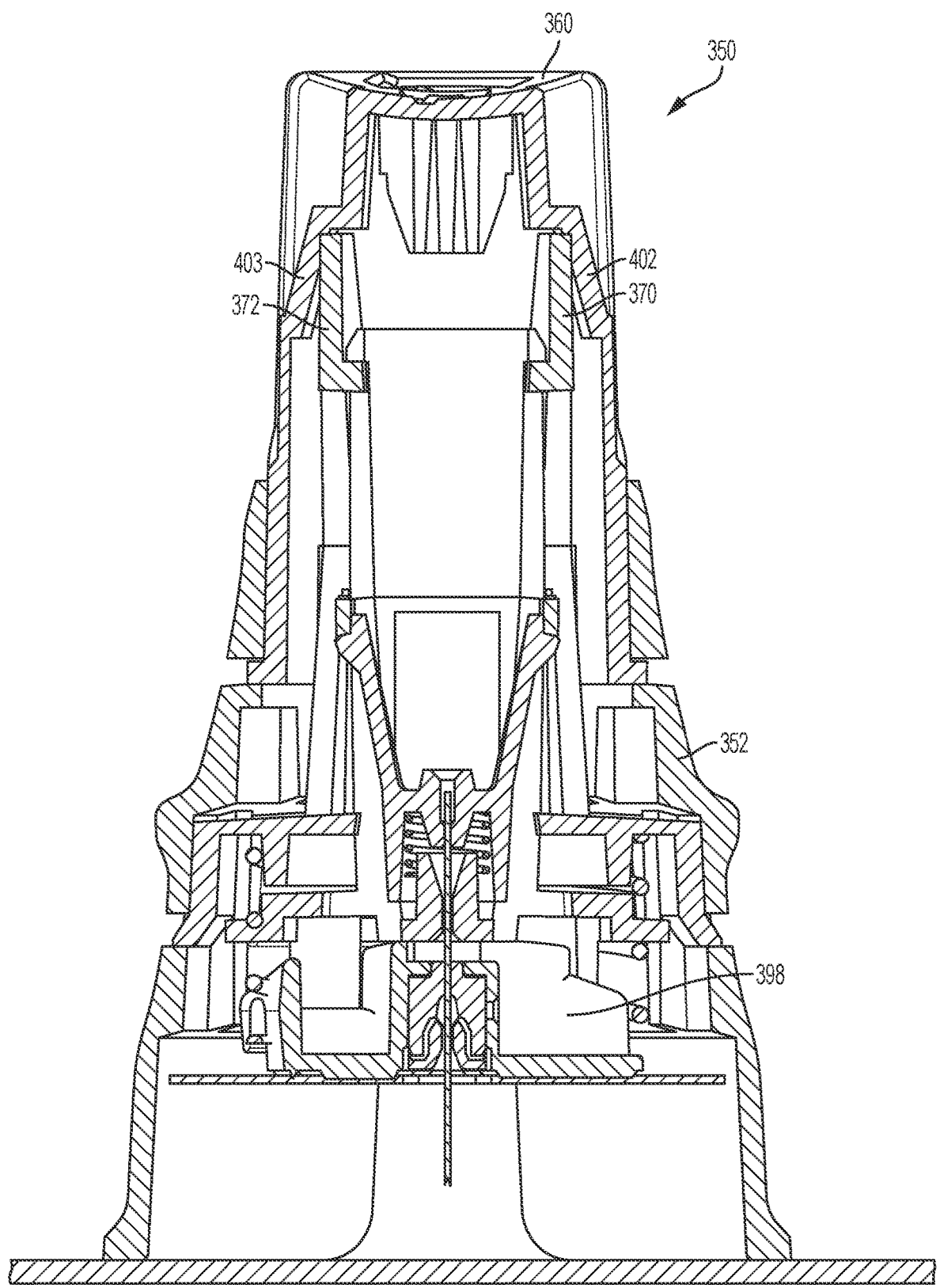
Figure 61:
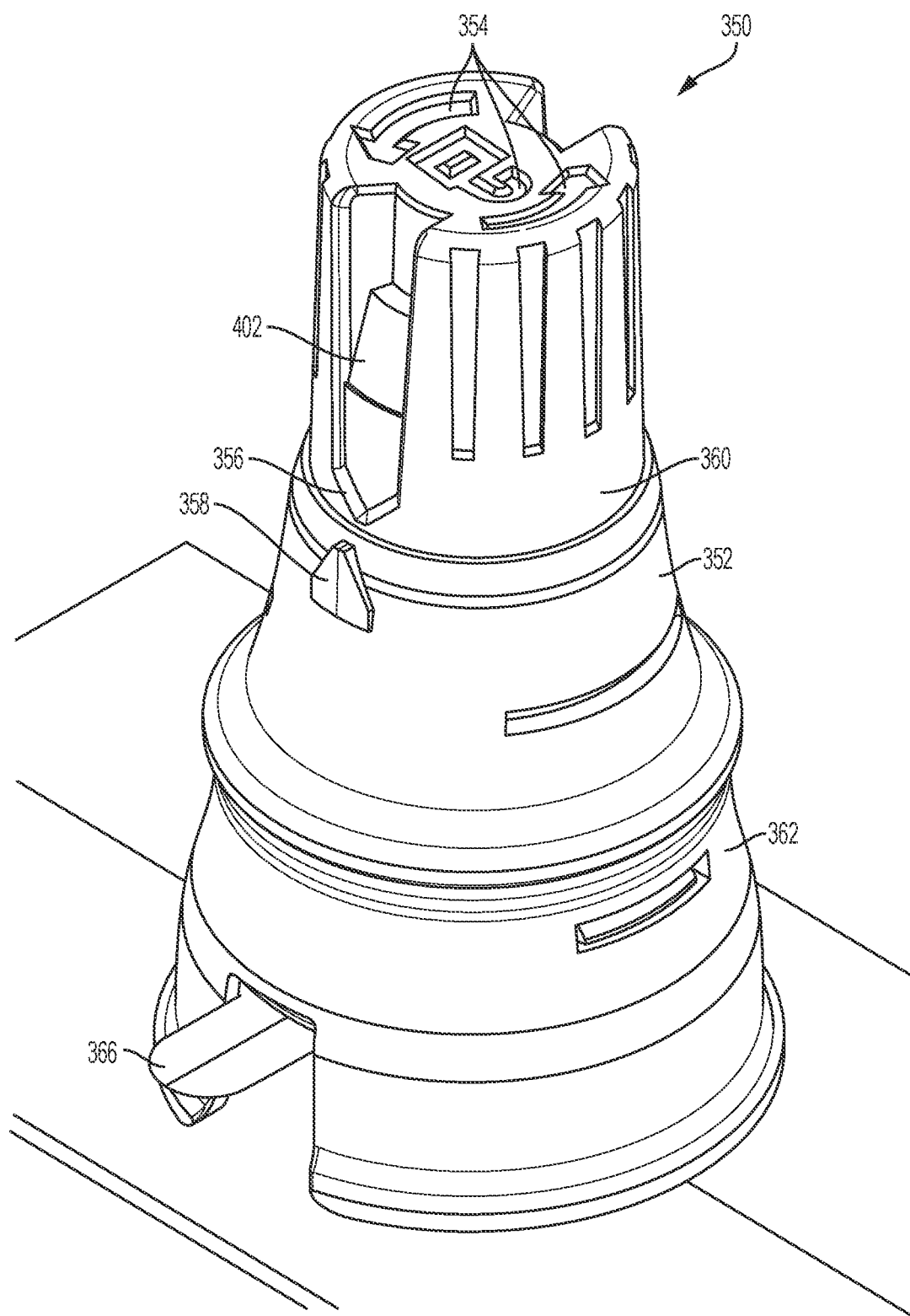
Figure 62:
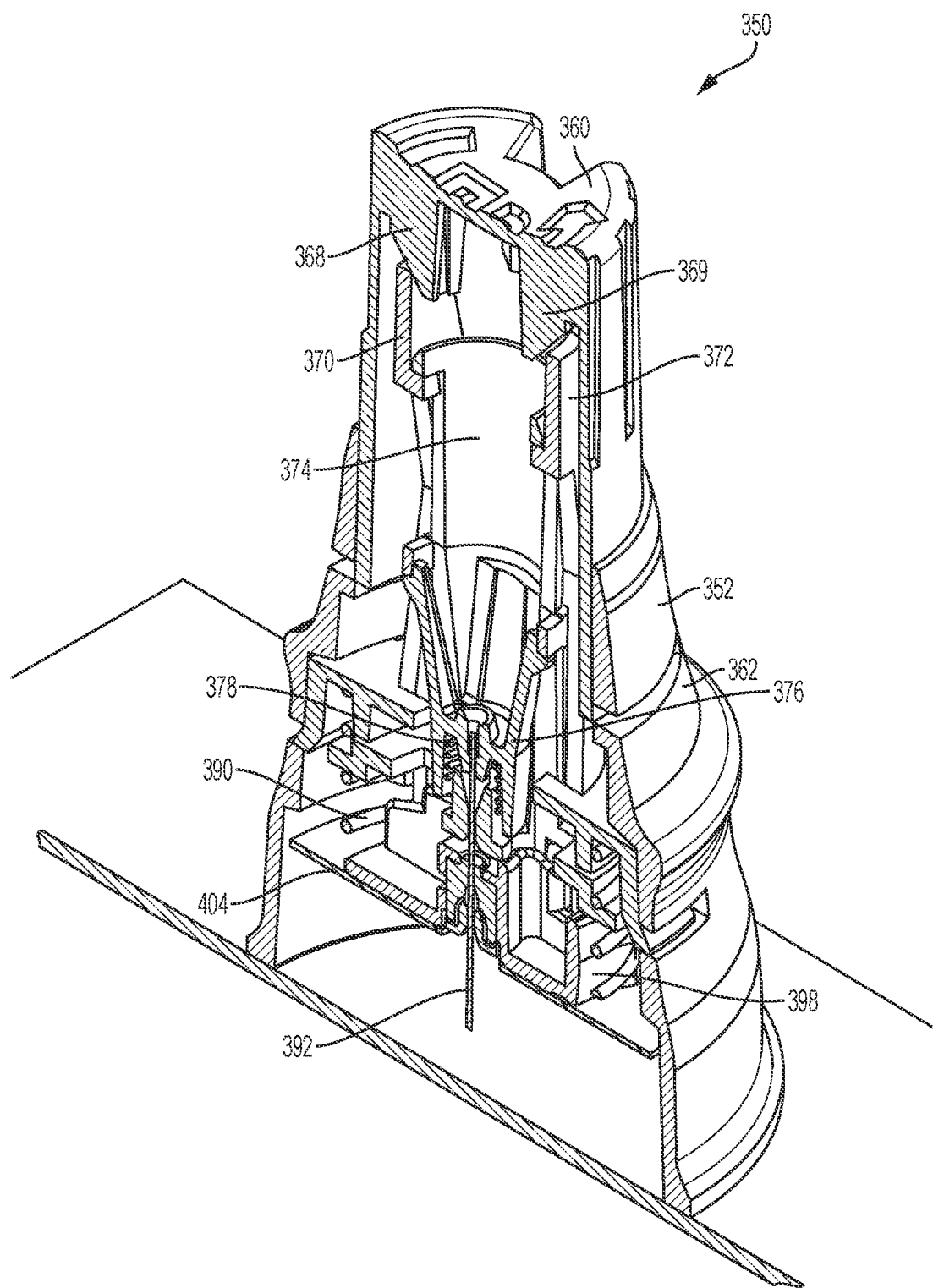
Figure 63:
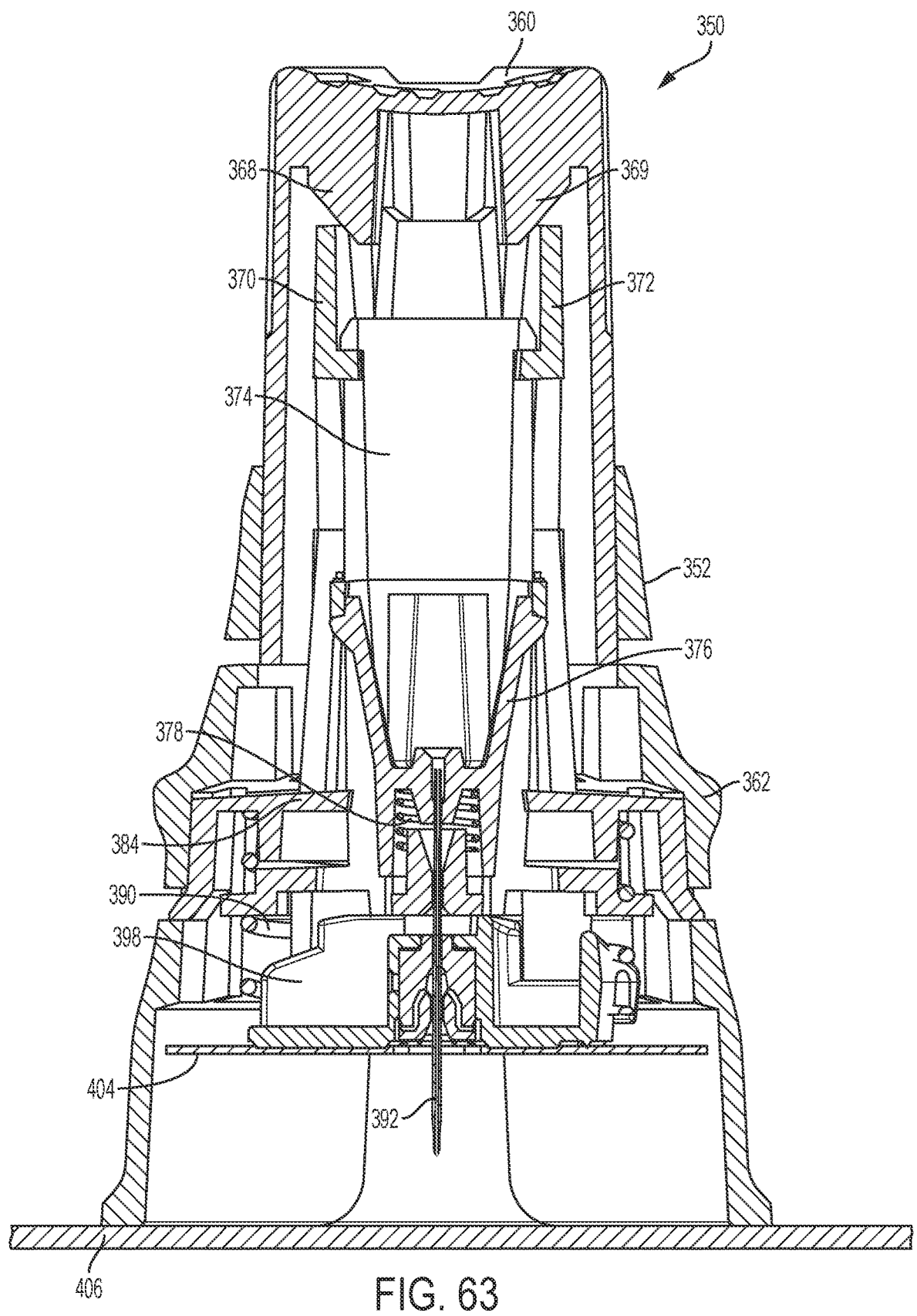
Figure 64:
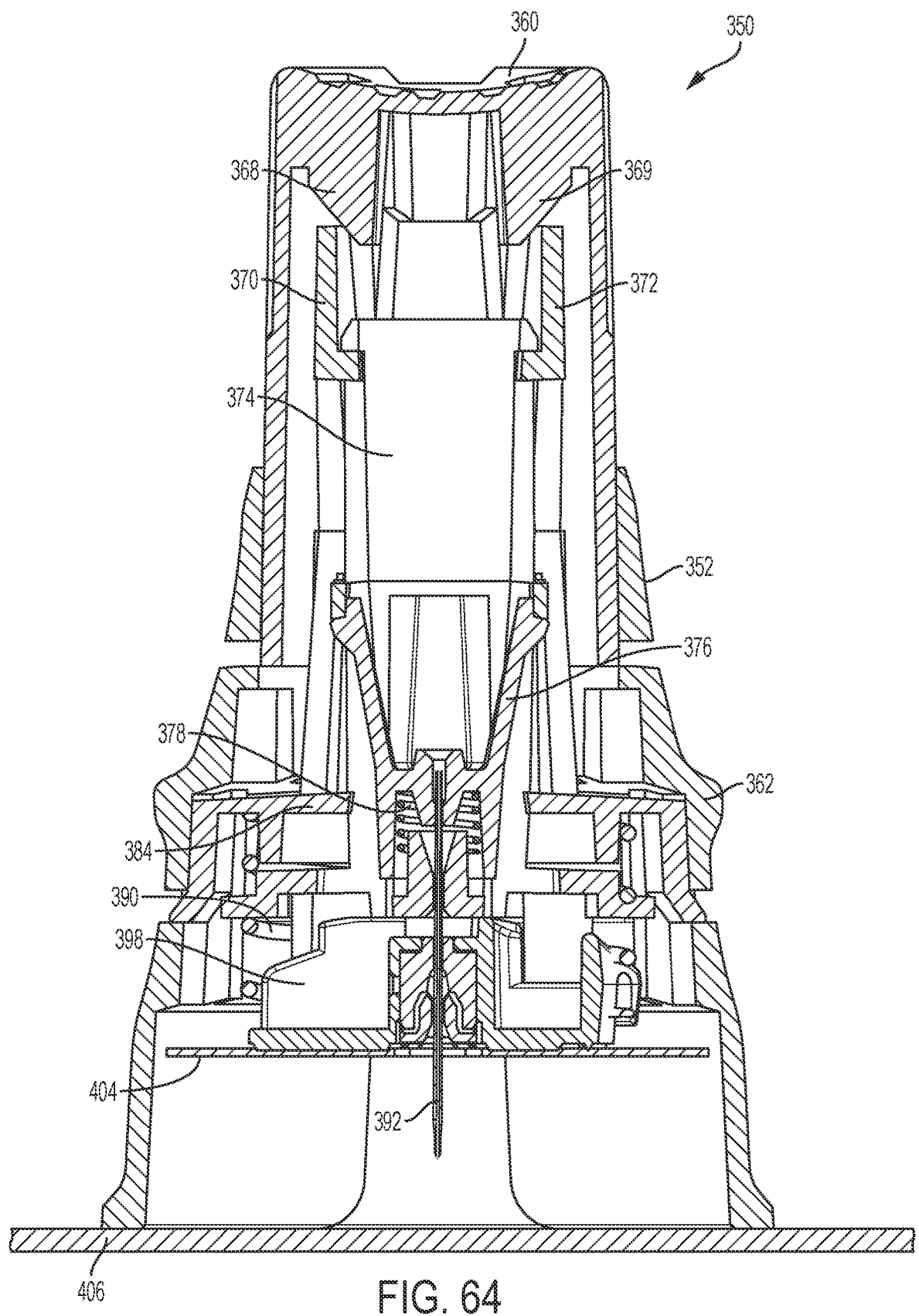
Figure 65:
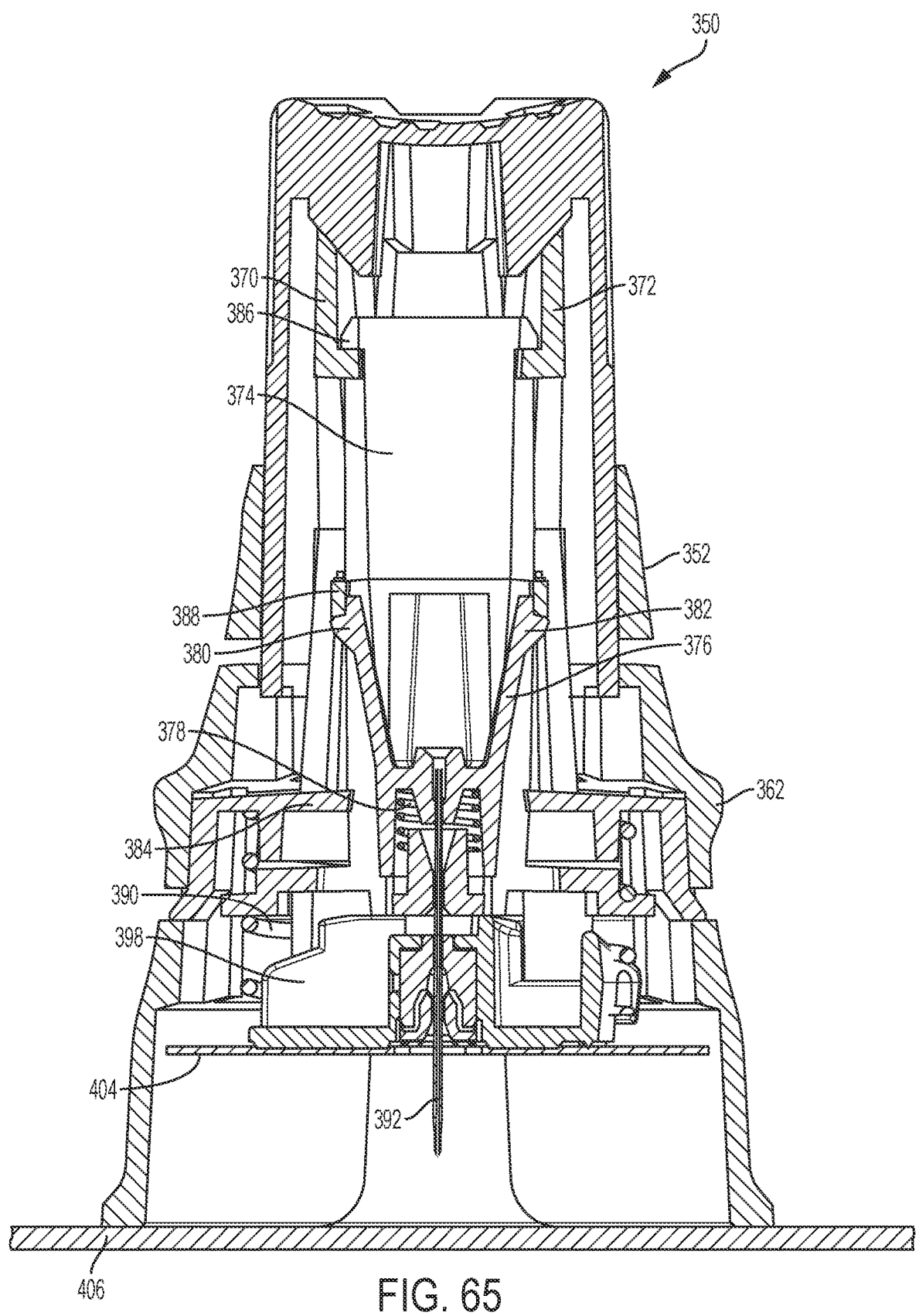

Referring now to FIGS. 60-71, one embodiment of an inserter assembly 350 is shown. The inserter assembly includes a housing portion 352 which includes a rotatable portion of housing 360 (which may also be referred to as a button assembly 360 or a rotatable button assembly 360) and a non-rotatable portion of housing 362. The inserter assembly 350 in some embodiments also includes a lock direction indicia 354 on the top of the rotatable portion of housing 360. In various embodiments the lock direction indicia includes a lock and/or unlock symbol and a one or more arrows indicating the direction to turn the rotatable portion of housing 360 to change the lock/unlock position. In FIG. 59 the inserter assembly 350 is shown in the locked position. The housing portion 352 in some embodiments also includes alignment features including a first alignment indicia 356 and a second alignment indicia 358 on the rotatable portion of housing 360 and the non-rotatable portion of housing 362 respectively. In practice, to change inserter assembly 350 from a locked position (as shown, for example, in FIG. 59) to an unlocked position (as shown, for example, in FIG. 61) the rotatable portion of housing 360 is rotated, with respect to the non-rotatable portion of housing 362, in the direction indicated by the lock direction indicia 354, until the first alignment indicia 356 is aligned with the second alignment indicia 358. In some embodiments, the first alignment indicia 356 and second alignment indicia 358 may be different form the ones shown in, for example, FIGS. 59-60. In various embodiments, the alignment indicia 356, 368 may be any shape and/or size and or may be any feature on the housing portion 352, including, but not limited to, a marking, indent/emboss, painted feature, written feature, and/or raised feature. Any of the alignment indicia 356, 358 may be any one or more of these types of features, or any other such features to indicate to a user/caregiver that the inserter assembly 350 is in the locked or unlocked position.

Still referring also to FIGS. 59-71, a button assembly 360 (which may also be referred to as the rotatable portion of housing) includes ramps 368, 369. In the locked position, the ramps 368, 369 do not interact with any other features of the inserter assembly. The button assembly 360 also includes tab indents 402 which, in the locked position, receives sliding component tabs 370, 372. Thus, in the locked position, the sliding component tabs 370, 372 are inside the tab indents 402 and this prevents force exerted in a downward motion (i.e., in the direction towards the infusion set 398) on the button assembly 360 from moving the button assembly 360, thus, the button assembly 360 is in a locked position. Thus until and unless the button assembly 360 (or rotatable portion of housing 360) is rotated to the unlocked position, the button assembly 360 cannot actuate the inserter assembly 350. This may be beneficial/desirable for many reasons, including but not limited to, prevention of mis-initiation or unintentional initiation of the inserter assembly.

When the button assembly 360/rotatable portion of housing 360 is rotated with respect to the non-rotatable portion of housing 362, the ramps 368, 369 also rotate and the sliding component tabs 370, 372 are removed from the tab indents 402 and now interact/touch the ramps 368, 369. The first alignment indicia 356 and second alignment indicia 358 are aligned. In this position the button assembly 360 may be actuated and thus initiate the inserter assembly two-step sequence.

Referring now also to FIGS. 62-71, the inserter sequence is shown and described. To initiate the inserter assembly 350, a user or caregiver exerts force/pressure on the button assembly 360 in the downward direction (i.e. in the direction of the infusion set 398). The sliding component tabs 370, 372 maintain the sliding component 374 in the starting position. As the button assembly 360 advances downward, the ramps 368, 369 push the sliding component tabs 370, 372 out of the way of the sliding component 374. The sliding component spring 390 is released and the sliding component 374 is pushed downwards, i.e., towards the infusion set 398 (see FIGS. 63-65). The sliding component 374 moving downward also pushes the needle carrier 376 downward. The needle component 376 is connected to the introduction needle 394 and at this stage, the cannula 396 is located around the introduction needle 394 forming a introduction needle/cannula assembly 392.

Figure 66:
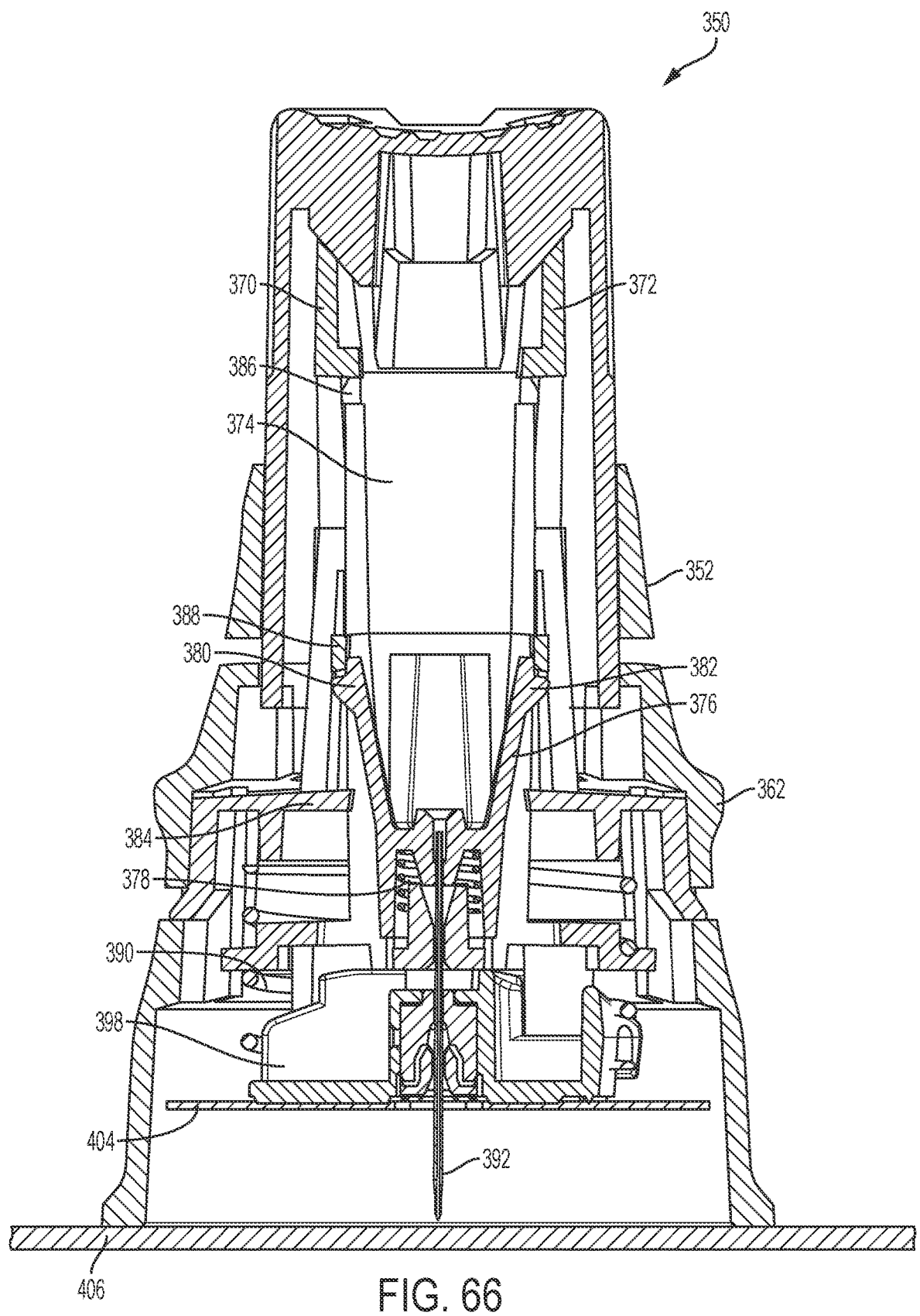
Figure 67:
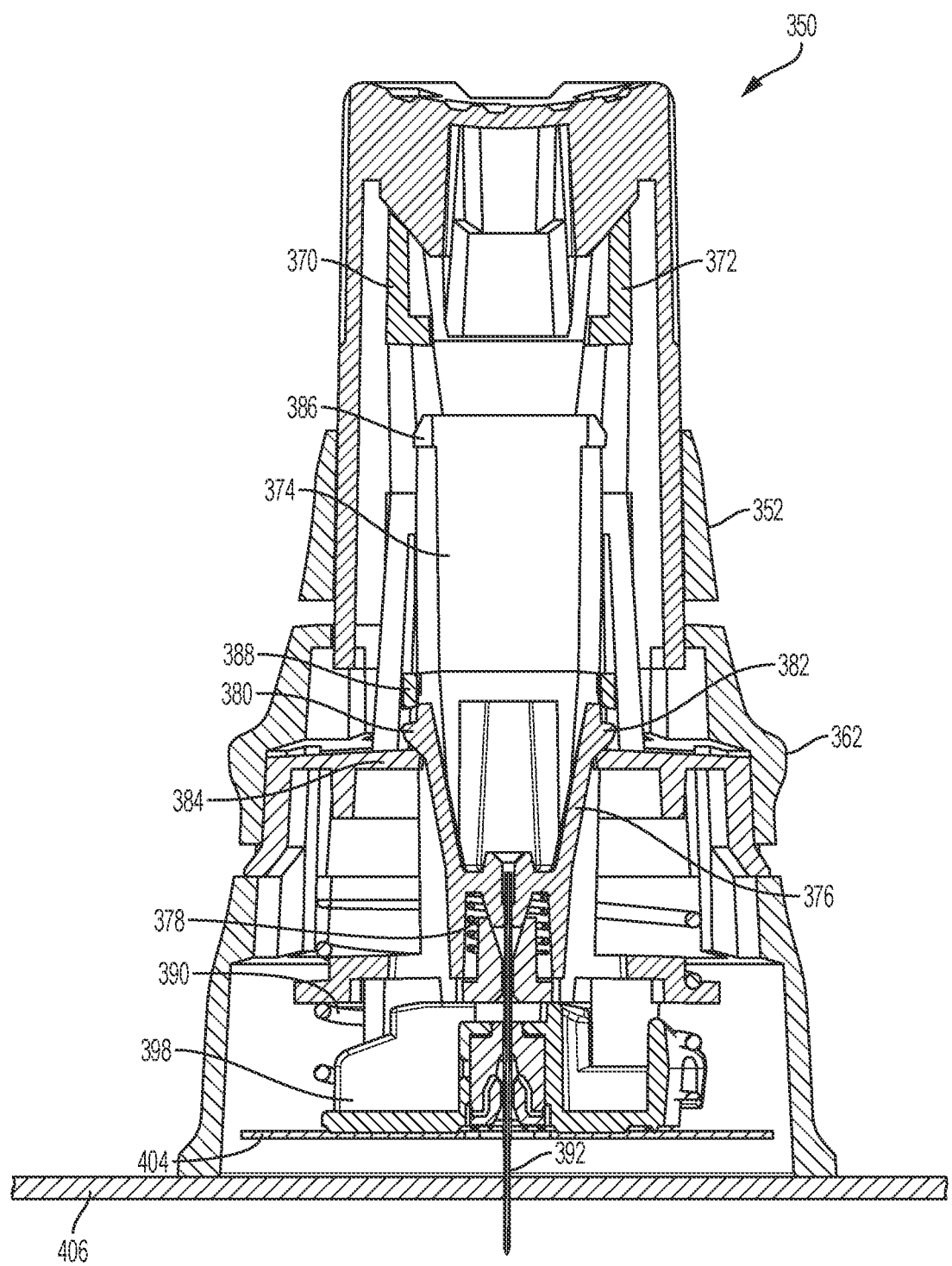
Figure 68:
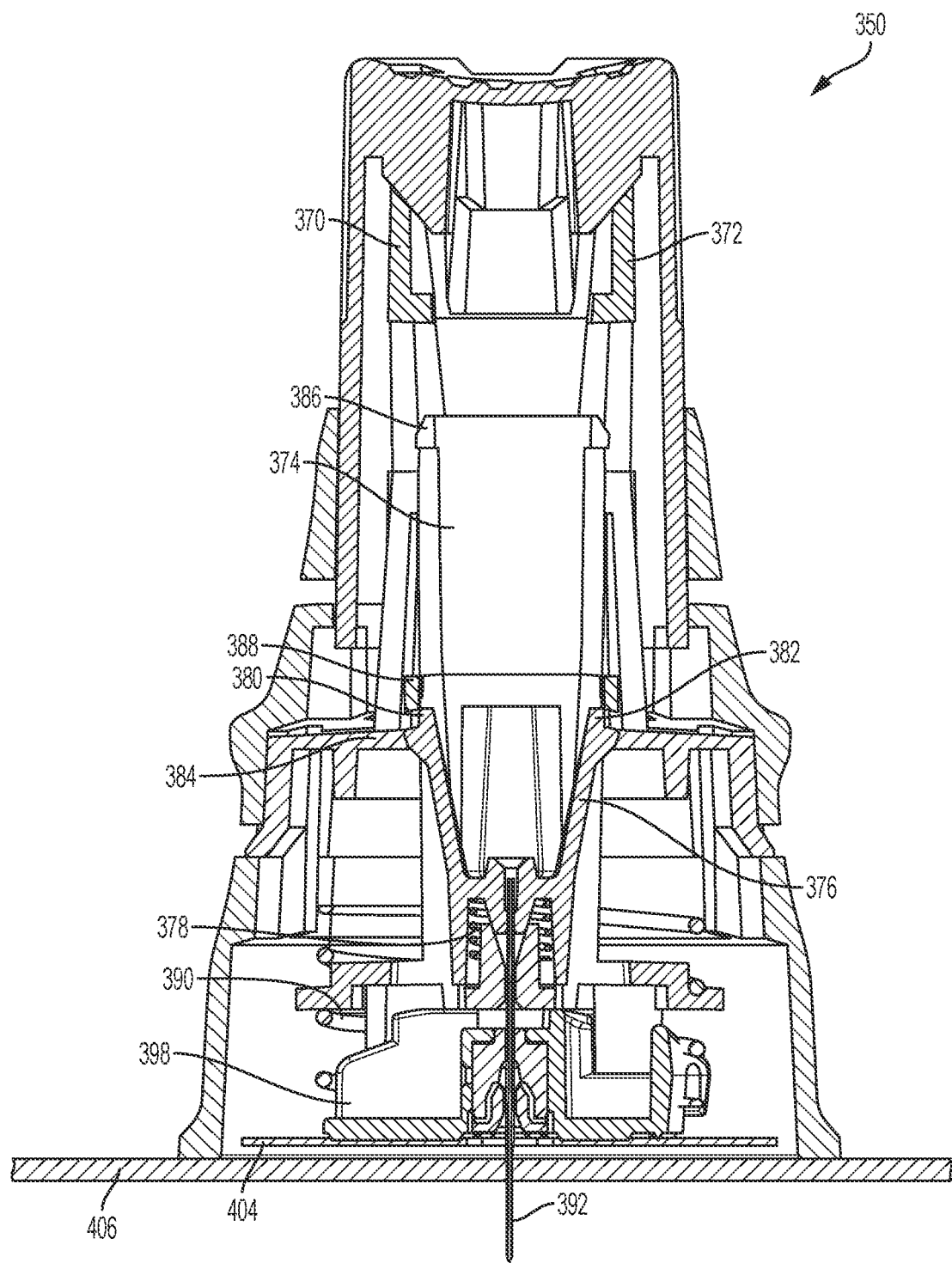
Figure 69:
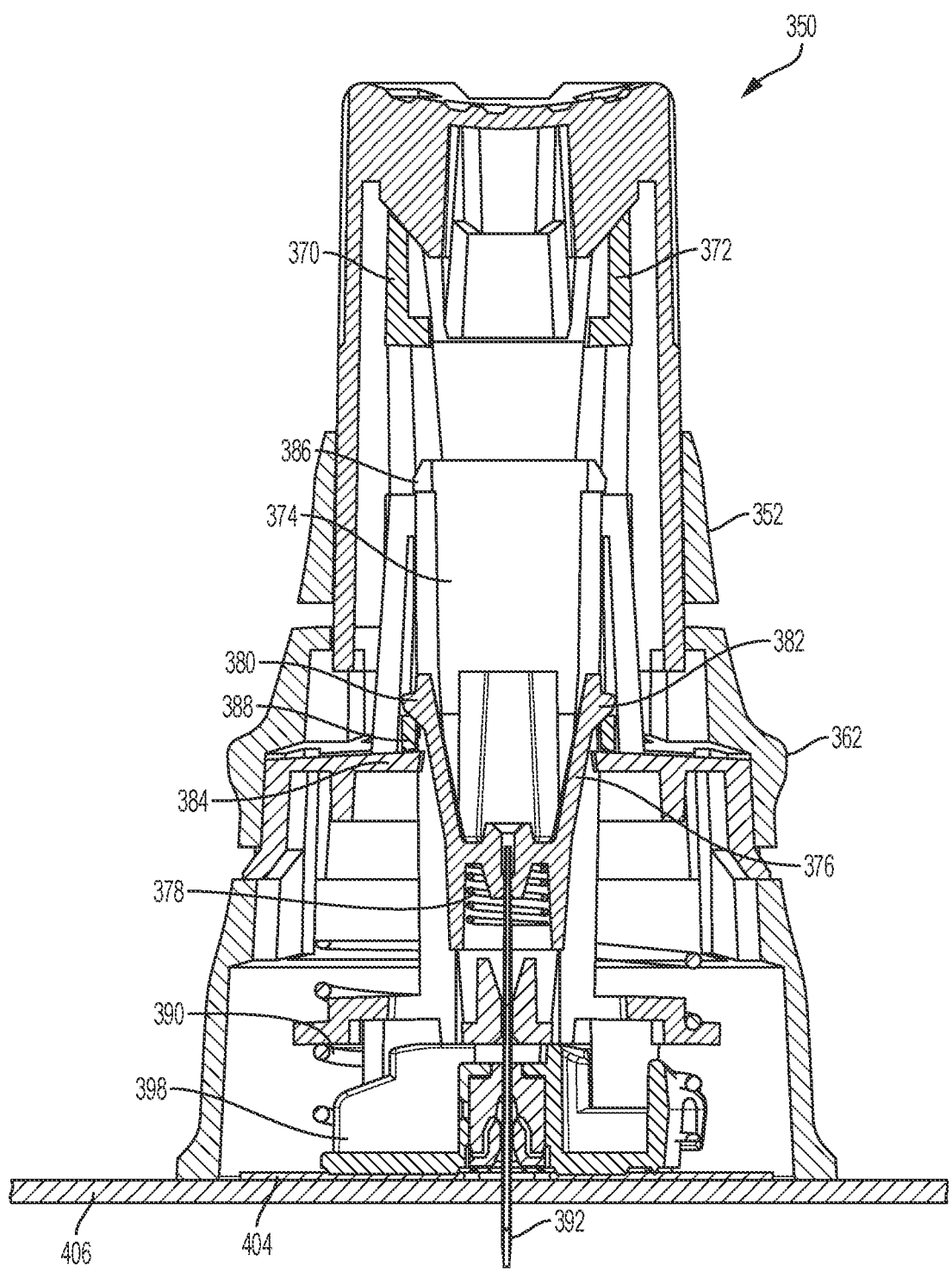

The needle carrier 376 and sliding component 374 continue moving downward (see FIGS. 66-67). This also pushes the insertion set 398 downward towards the user's skin 406. The sliding component 374 continues a downward path until the sliding component bottom tab 388 meets the slider stop 384 (see FIG. 69).

The needle carrier 376 continues a downward path even after the sliding component bottom tab 388 meets the slider stop 384. At that point the needle carrier spring fingers 380, 382 of the needle carrier 376 are pushed inward by the slider stop 384 and the needle carrier 376 continues downward and in following this path, the downward force of the needle carrier 376 injects the introduction needle/cannula assembly 392 into the user's skin 406 (see FIG. 68).

When the needle carrier 376 reaches the end of its travel path, the infusion set 398 is on the user's skin and the cannula 396 is inserted in the user. The needle carrier 376 is then released and the needle spring 378 forces the needle carrier 376 and the introduction needle 394, as the introduction needle 394 is attached to the needle carrier 376, upwards, towards the button assembly 360 (see FIG. 71). The upward movement of the needle carrier 376 continues until the spring fingers 380, 382 are caught on the sliding component top tab 386. At this point, the needle carrier 376 is locked into an end position and the introduction needle 394 is completely inside the housing portion 352. The infusion set 398 is attached to the user and the cannula 396, which is part of the infusion set, has been successfully inserted into the user.

Figure 70:
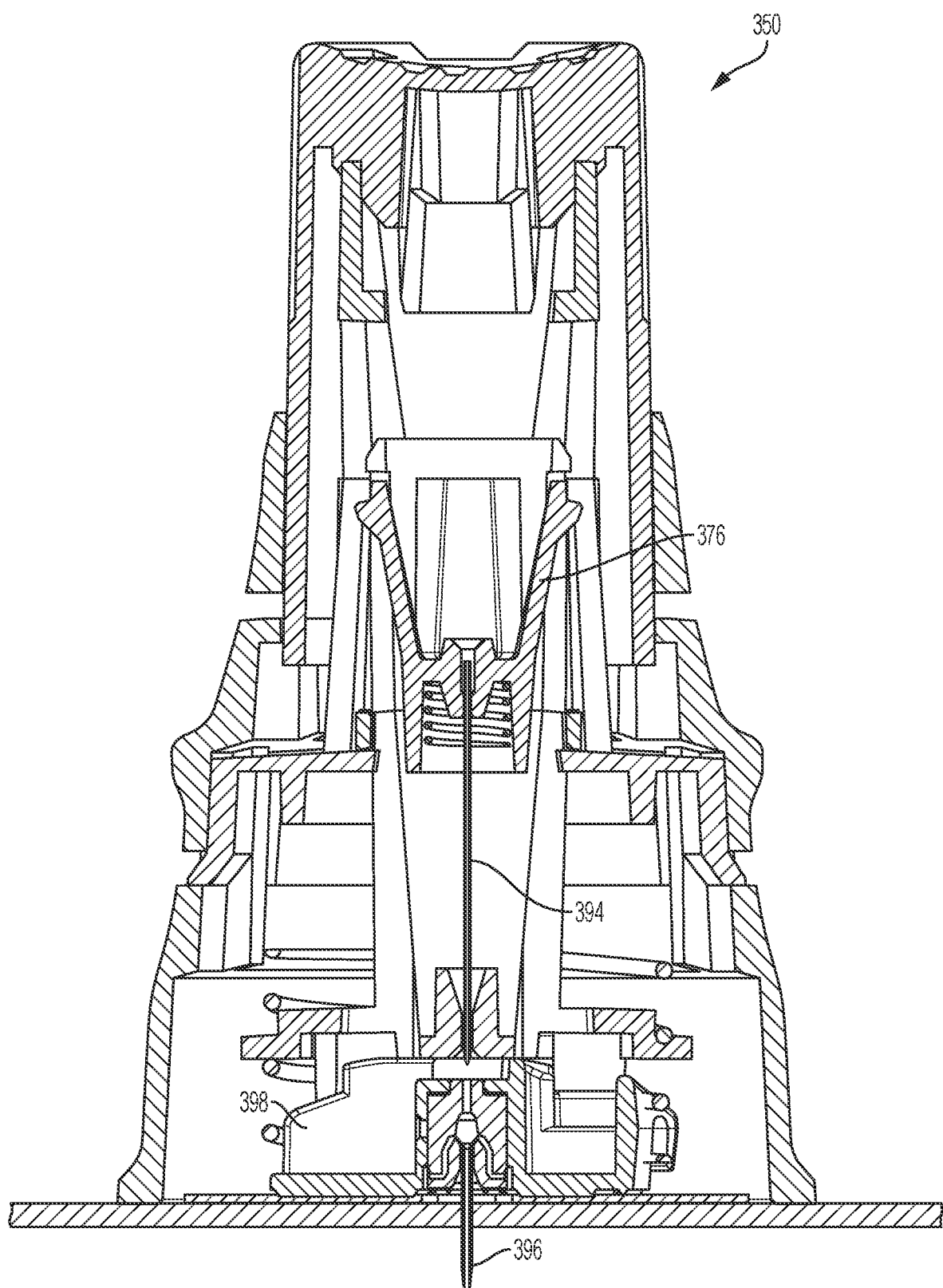
Figure 71:
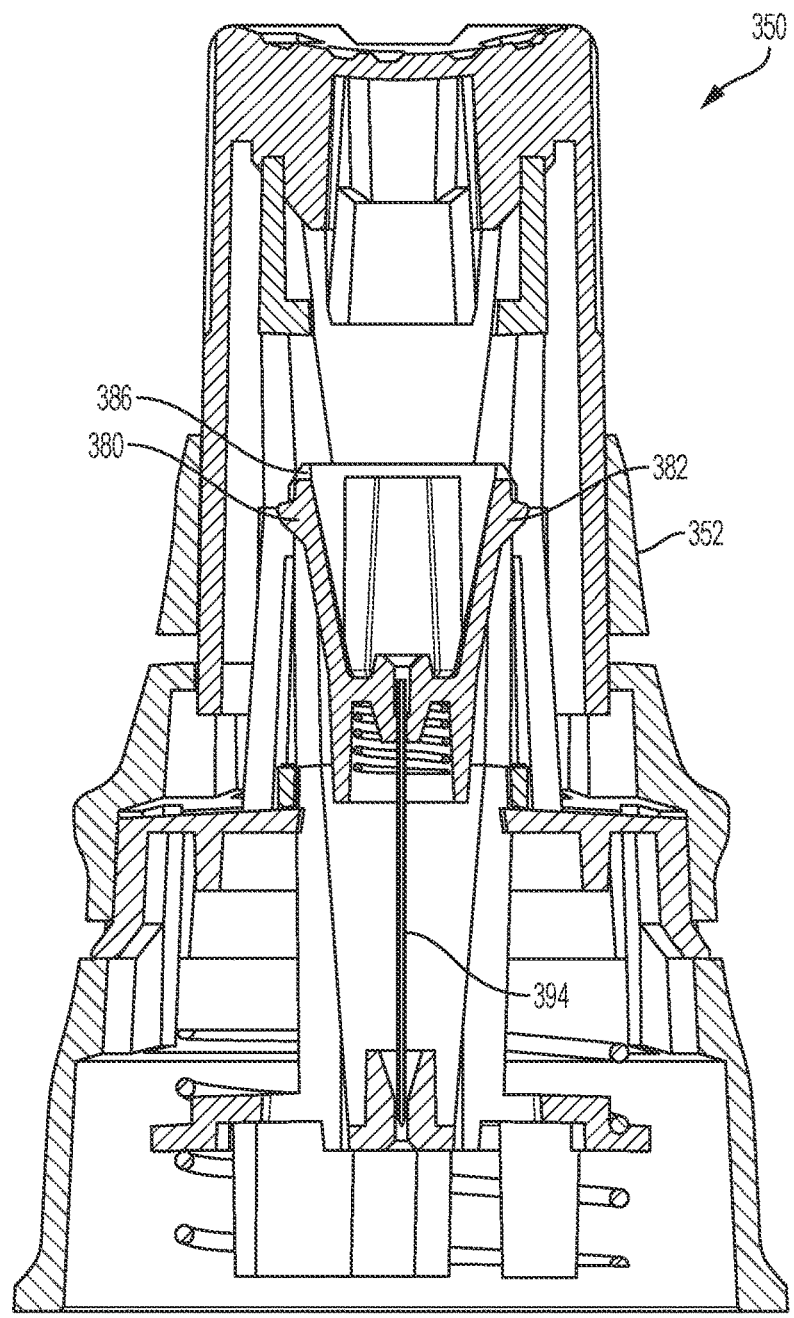
Figure 71:
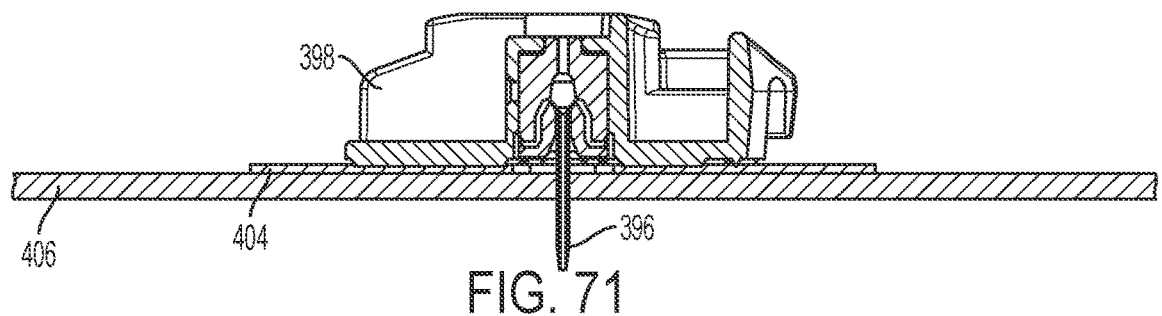

Thus, the needle carrier 376 is slidably moveable from a starting position (FIG. 63) to an injection position (FIG. 68) and then to an ending position (FIG. 70). The button assembly/rotatable portion of housing/rotatable button assembly 360 rotates from a locked position to an unlocked position. By exerting downward force onto the rotatable button assembly 360, the rotatable button assembly 360 moves downward, which forces the sliding component 374 downward (through interaction between the ramps 368, 369 and the sliding component tabs 370, 372), and the needle carrier 376, which is attached to the introduction needle 394, downward towards the user's skin. Once the needle carrier 376 reaches the injection position, the spring fingers 380, 382 are pushed inward and the needle spring 378 pushes/forces the needle carrier 376 to move upward, towards the rotatable button assembly 360, until it stops at the ending position.

In various embodiments, the infusion set 398 includes an adhesive layer 404. In some embodiments, the adhesive may be covered by a liner, for example, an adhesive liner 366. In some embodiments, before putting the inserter assembly 350 against the skin, the user/caregiver removes the adhesive liner. In some embodiments, no adhesive liner is included.

The various bases, connectors, inserters, and parts thereof, may be formed from any materials including, but not limited to, medical-grade plastic materials. The various needles described herein may be formed from any medical-grade materials. The cannula and tubing may be formed from any medical-grade materials. In various embodiments, the insertion set includes a base, connector, tubing and a luer connection or other connector configured to connect to a fluid source.

A number of embodiments have been described. Nevertheless, it will be understood that various modifications may be made. Accordingly, other embodiments are within the scope of the following claims.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. An infusion device comprising:
   a base portion comprising at least one tube routing organizer cutout configured to retain a portion of a length of tubing;
   a cannula;
   a septum retainer comprising a retainer cutout formed as a depression in central portion of a skin-facing face of the septum retainer; and
   a connector comprising a connector needle, the connector configured to be removably attached to the base portion, the length of tubing having a downstream terminal end which is attached to the connector and in fluid communication with the connector needle,
   wherein the cannula is located within the retainer cutout.

2. The infusion device of claim 1, wherein the connector comprises connector fingers comprising ribbing.

3. The infusion device of claim 1, wherein the connector comprises a connector needle protector located above the connector needle.

4. The infusion device of claim 1, wherein the retainer cutout contains a topically introduced ointment.

5. The infusion device of claim 1, wherein the base further comprises a finger grip area configured for finger grip stability while connecting the base and the connector.

6. The infusion device of claim 1, wherein the depression is an annular recess having a cross-sectional shape of a conical segment.

7. The infusion device of claim 1, wherein the infusion device further comprises a septum, the septum captured within the base at least partially via the septum retainer.

8. The infusion device of claim 1, wherein the septum retainer is coupled to the base via a press fit and the septum retainer includes at least one cantilevered coupling arm.

9. An infusion device comprising:
   a base portion comprising at least one cutout configured to retain a portion of a length of tubing;
   a cannula;
   a septum retainer comprising a retainer cutout; and
   a connector comprising a connector needle, the connector configured to be removably attached to the base portion, the length of tubing having a downstream terminal end which is attached to the connector and in fluid communication with the connector needle,
   wherein the cannula is surrounded by the retainer cutout.

10. The infusion device of claim 9, wherein the connector comprises ribbed connector fingers.

11. The infusion device of claim 9, wherein the connector comprises a connector needle protector finger located above the connector needle.

12. The infusion device of claim 9, wherein the retainer cutout contains a topical ointment.

13. The infusion device of claim 9, wherein the base further comprises a finger grip area configured for finger grip stability while connecting the base and the connector.

14. The infusion device of claim 9, wherein the retainer cutout is an annular recess having a cross-sectional shape of a conical segment.

15. The infusion device of claim 9, wherein the infusion device further comprises a septum, the septum captured within the base at least partially via the septum retainer.

16. The infusion device of claim 9, wherein the septum retainer is coupled to the base via a press fit and the septum retainer includes at least one cantilevered coupling arm.

17. An infusion device comprising:
- a base portion comprising at least one cutout configured to retain a portion of a length of tubing;
- a tubing connector comprising a connector needle, the connector configured to be removably attached to the base portion and coupled to the length of tubing;
- a cannula; and
- a septum retainer comprising a retainer cutout formed as a depression in central portion of a skin-facing face of the septum retainer, wherein the cannula is surrounded by the retainer cutout.

18. The infusion device of claim 17, wherein the cannula is configured to pivot within the retainer cutout with respect to the base.

19. The infusion device of claim 17, wherein the depression is annular and has a cross-sectional shape of a conical segment.

20. The infusion device of claim 17, wherein the connector comprises a connector needle protector finger located above the connector needle.

21. The infusion device of claim 17, wherein the connector comprises ribbed connector fingers.

\* \* \* \* \*